(12) United States Patent
Estrela Ariguel et al.

(10) Patent No.: US 11,179,348 B2
(45) Date of Patent: Nov. 23, 2021

(54) COMBINATION COMPRISING PTEROSTILBENE FOR THE TREATMENT OF CANCER

(71) Applicants: FUNDACIÓN UNIVERSIDAD CATÓLICA DE VALENCIA SAN VICENTE MÁRTIR, Valencia (ES); UNIVERSITAT DE VALÈNCIA-ESTUDI GENERAL, Valencia (ES); FUNDACIÓ INVESTIGACIÓ HOSPITAL GENERAL UNIVERSITARI DE VALÈNCIA PER A LA INVESTIGACIÓ BIOMÈDICA I CIÈNCIES DE LA SALUT, Valencia (ES); IDCQ HOSPITALES Y SANIDAD, S.L.U., Madrid (ES)

(72) Inventors: José María Estrela Ariguel, Valencia (ES); María Benlloch García, Valencia (ES); María Elena Plá Obrador, Valencia (ES); Lilian Soraya Vallés Martín, Valencia (ES); María Lucía Rodríguez Romero, Valencia (ES); Joan Antoni Sirerol Talens, Valencia (ES); Javier Luis Alcácer García, Valencia (ES); José Alfredo Pellicer Artés, Valencia (ES); Rosario Salvador Palmer, Valencia (ES); Guillermo María Sáez Tormo, Valencia (ES); Concepción Cerdá Micó, Valencia (ES)

(73) Assignees: FUNDACIÓN UNIVERSIDAD CATÓLICA DE VALENCIA SAN VICENTE MÁRTIR, Valencia (ES); UNIVERSITAT DE VALÈNCIA—ESTUDI GENERAL, Valencia (ES); FUNDACIÓ INVESTIGACIÓ HOSPITAL GENERAL UNIVERSITARI DE VALÈNCIA PER A LA INVESTIGACIÓ BIOMÈDICA I CIÈNCIES DE LA SALUT, Valencia (ES); IDCQ HOSPITALES Y SANIDAD, S.L.U., Madrid (ES)

( * ) Notice: Subject to any disclaimer, the term of this patent is extended or adjusted under 35 U.S.C. 154(b) by 202 days.

(21) Appl. No.: 15/746,311

(22) PCT Filed: Jun. 9, 2016

(86) PCT No.: PCT/EP2016/063195
§ 371 (c)(1),
(2) Date: Jan. 19, 2018

(87) PCT Pub. No.: WO2017/012774
PCT Pub. Date: Jan. 26, 2017

(65) Prior Publication Data
US 2018/0214390 A1    Aug. 2, 2018

(30) Foreign Application Priority Data
Jul. 21, 2015    (EP) ..................... 15382378

(51) Int. Cl.
*A61K 31/09* (2006.01)
*A61P 35/00* (2006.01)
(Continued)

(52) U.S. Cl.
CPC ............ *A61K 31/09* (2013.01); *A61K 31/225* (2013.01); *A61K 31/277* (2013.01); *A61K 31/42* (2013.01);
(Continued)

(58) Field of Classification Search
CPC .. A61K 31/09; A61K 2300/00; A61K 31/225; A61K 31/277; A61K 31/42;
(Continued)

(56) References Cited

FOREIGN PATENT DOCUMENTS

WO    WO 2011/042482 A1    4/2011

OTHER PUBLICATIONS

Schneider et al., Effects of pterostilbene on melanoma alone and in synergy with inositol hexaphosphate, 2009, The American Journal of Surgery, 198, pp. 670-684 (Year: 2009).*
(Continued)

*Primary Examiner* — Savitha M Rao
(74) *Attorney, Agent, or Firm* — James S. Keddie; Bozicevic, Field & Francis LLP

(57) ABSTRACT

The present invention relates to a combination comprising pterostilbeneor pterostilbene phosphate or a pharmaceuti-
(Continued)

cally acceptable salt thereof, a glutathione depleting agent and a cancer chemotherapeutic agent. The invention also relates to the medical use of this combination, in particular for the treatment and/or prevention of cancer.

11 Claims, 62 Drawing Sheets

Specification includes a Sequence Listing.

(51) Int. Cl.
$$\begin{array}{ll}
\text{A61K 31/225} & (2006.01) \\
\text{A61K 31/277} & (2006.01) \\
\text{A61K 31/42} & (2006.01) \\
\text{A61K 31/4412} & (2006.01) \\
\text{A61K 31/551} & (2006.01) \\
\text{A61K 31/635} & (2006.01)
\end{array}$$

(52) U.S. Cl.
CPC ........ *A61K 31/4412* (2013.01); *A61K 31/551* (2013.01); *A61K 31/635* (2013.01); *A61P 35/00* (2018.01)

(58) Field of Classification Search
CPC .............. A61K 31/4412; A61K 31/551; A61K 31/635; A61P 35/00
See application file for complete search history.

(56) References Cited

OTHER PUBLICATIONS

Segura et al., BRD4 Sustains Melanoma Proliferation and Represents a New Target for Epigenetic Therapy, 2013, Cancer Res., 73 (20), pp. 6264-6276 (Year: 2013).*
Wiernik et al., Taxol in malignant melanoma, 1993, J Natl Cancer Inst Monogr., 15, pp. 185-187, abs (Year: 1993).*
Priego et al., "Natural polyphenols facilitate elimination of HT-29 colorectal cancer xenografts by chemoradiotherapy: a Bcl-2- and superoxide dismutase 2-dependent mechanism", Mol Cancer Ther, 2008, 7(10): 3330-3342.
Mena et al., "Bcl-2 and Glutathione Depletion Sensitizes B16Melanoma to CombinationTherapy and EliminatesMetastatic Disease", Cin Cancer Res, 2007,13(9): 2658-2666.
Benlloch et al., "Bcl-2 and Mn-SOD Antisense Oligodeoxynucleotides and a Glutamine-enriched Diet Facilitate Elimination of Highly Resistant B16 Melanoma Cells by Tumor Necrosis Factor-α and Chemotherapy", The Journal of Biological Chemistry, 2006, 281(1): 69-79.
Ortega et al., "Glutathione in Cancer Cell Death", Cancers, 2011, 3: 1285-1310, doi:10.3390/cancers3011285.
Mena et al., "Glutathione and Bcl-2 targeting facilitates elimination by chemoradiotherapy of human A375 melanoma xenografts overexpressing bcl-xl, bcl-2, and mcl-1", Journal of Translational Medicine, 2012, 10:8, http://www.translational-medicine.com/content/10/1/8.
Yang et al., "Pterostilbene Exerts Antitumor Activity via the Notch1 Signaling Pathway in Human Lung Adenocarcinoma Cells", PLOS ONE, 2013, 8(5): e62652.
Zhang et al., "Involvement of the Nrf2 Pathway in the Regulation of Pterostilbene-Induced Apoptosis in HeLa Cells via ER Stress", Journal of Pharmacological Sciences, 2014, 126: 216-229.
Ferrer et al., "Association between Pterostilbene and Quercetin Inhibits Metastatic Activity of B16 Melanoma", Neoplasia, 2005, 7(1): 37-47.
Ferrer et al., "Nitric Oxide Mediates Natural Polyphenol-induced Bcl-2 Down-regulation and Activation of Cell Death in Metastatic B16 Melanoma", The Journal of Biological Chemistry, 2007, 282(5): 2880-2890.
Obrador et al., "Glucocorticoid Receptor Knockdown Decreases the Antioxidant Protection of B16 Melanoma Cells: An Endocrine System-Related Mechanism that Compromises Metastatic Cell Resistance to Vascular Endothelium-Induced Tumor Cytotoxicity", PLOS ONE, 2014, 9(5): e96466.
Benlloch et al., "Acceleration of Glutathione Efflux and Inhibition of γ-Glutamyltranspeptidase Sensitize Metastatic B16 Melanoma Cells to Endothelium-induced Cytotoxicity", The Journal of Biological Chemistry, 2005, 280(8): 6950-6959.
Valles et al., "Stress hormones promote growth of B16-F10 melanoma metastases: an interleukin 6- and glutathione-dependent mechanism", Journal of Translational Medicine, 2013, 11:72, http://www.translational-medicine. com/content/Nov. 1, 72.
Dbrador et al., "Intertissue Flow of Glutathione (GSH) as a Tumor Growth-promoting Mechanism", The Journal of Biological Chemistry, 2011, 286(18): 15716-15727.
Benlloch et al., "Pterostilbene Decreases the Antioxidant Defenses of Aggressive Cancer Cells In Vivo X Physiological Glucocorticoidsand- and Nrf2-Dependent Mechanism", ANTIOXIDANTS & Redox Signaling, 2016, 24(17): 974-990.

* cited by examiner

A

B

C

COMBINATION COMPRISING PTEROSTILBENE FOR THE TREATMENT OF CANCER

CROSS-REFERENCE TO RELATED APPLICATIONS

This application is a § 371 national phase of International Application No. PCT/EP2016/063195, filed on June 9, 2016, which claims the benefit of European Application No. 15382378.6, filed on Jul. 21, 2015, which applications are incorporated by reference herein.

FIELD OF THE INVENTION

The present invention relates to the field of cancer therapies, in particular to the treatment and prevention of cancer in general and melanoma in particular.

BACKGROUND OF THE INVENTION

Phytochemicals of polyphenolic structure, commonly named natural polyphenols (PFs), are secondary metabolites of plants involved in the defense against different types of stress, including ultraviolet radiation, aggression by pathogens, low soil fertility, high/low temperatures, severe drought, and grazing pressure. Their potential benefits for human health are numerous and include anticancer properties. Abundant information is now available on cellular mechanisms by which PFs may interfere with carcinogenesis, tumor growth and dissemination. However a main problem with PFs is their short half-life and low bioavailability under in vivo conditions. Indeed the main discrepancy between health claims versus clinical observations is the frequent use of non-physiologically relevant concentrations of these compounds in mechanistic studies. This discrepancy represents a fundamental question which is still unsolved.

Different PFs have been shown to inhibit cancer growth in vivo. Nevertheless it is unclear how potential underlying mechanisms can be correlated with bioavailable concentrations and biological half-life.

Recent studies have tested, both in vitro and in vivo, the antitumor effect of pterostilbene (trans-3,5-dimethoxy-4'-hydroxystilbene; Pter), a natural dimethoxylated analog of resveratrol but with higher biological half-life. However the use in vitro of unattainable in vivo concentrations and/or long-term exposure (24 h or more) seriously questions the relative importance of the proposed mechanisms, e.g. via metastases-associated protein 1 in prostate cancer, estrogen receptor-α36, or the PI3K/Akt and MAPKs signaling pathways in colon cancer. 20 µM Pter, incubated for 24 h under in vitro culture conditions, was observed to decreased tumor cell viability by approx. 30% in human A375 melanoma, 40% in A549 human lung cancer, 10% in HT-29 human colon cancer, and 25% in human breast cancer (Mena, S. et al., *PLoS One* 2012, 7, e44524). However, no significant decrease in cell viability was observed if the incubation time was <6 h. Thus questioning mechanisms claimed to explain the in vivo induced tumor growth inhibition elicited by pterostilbene (or other related molecules), at least under conditions where pterostilbene needs the blood circulation to reach the growing tumor.

Despite the efforts made to date, there still exists a long-felt and continuing need in the art for novel compounds and/or therapies useful in cancer treatment.

SUMMARY OF THE INVENTION

Figure 1:
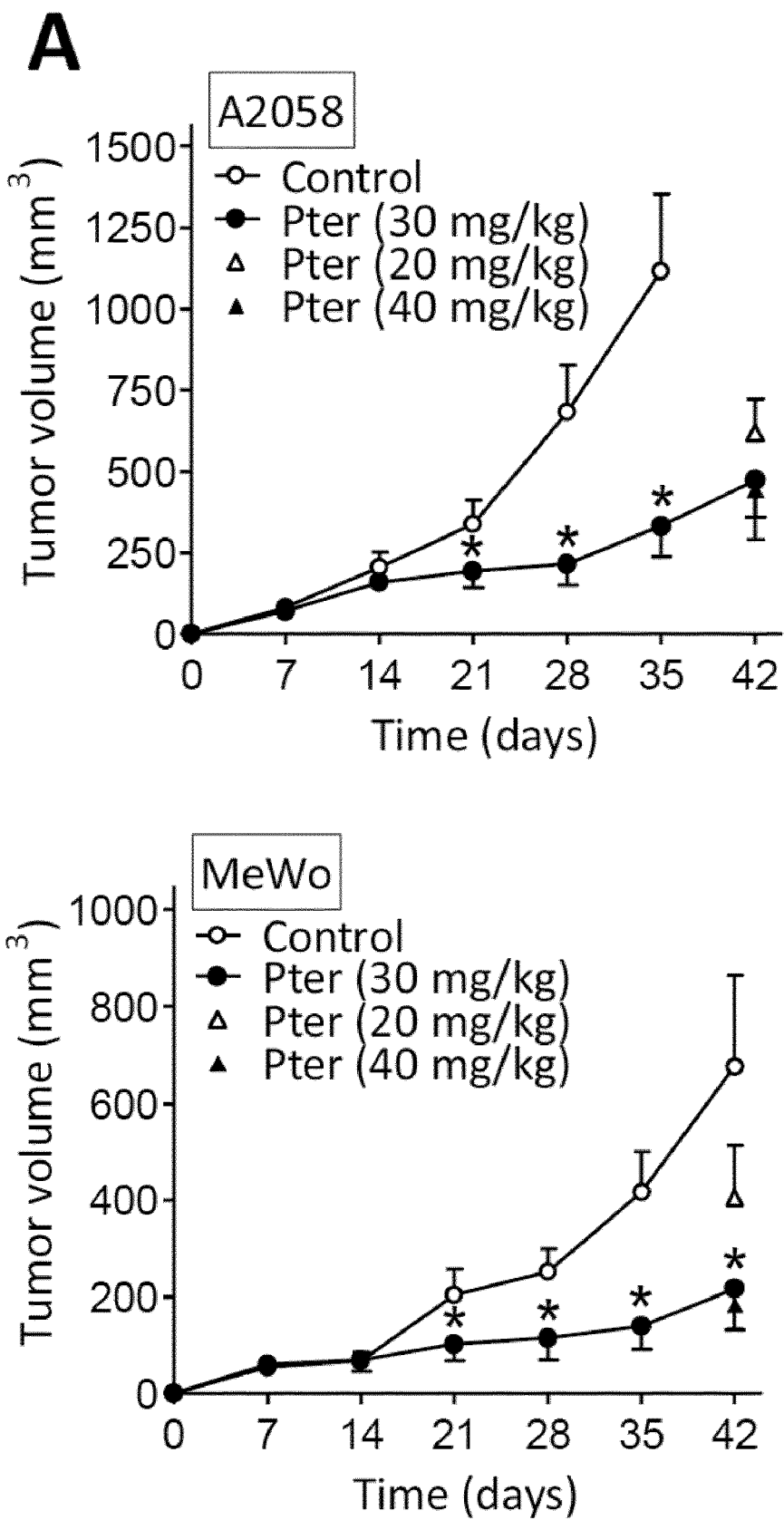
FIG. 1. In vivo and in vitro effect of pterostilbene on human melanoma growth and its relationship with bioavailable pterostilbene concentrations. (A) Effect of pterostilbene on melanoma growth in vivo. pterostilbene was administered i.v. every 48 h for a period of 5 weeks, starting 1 week after tumor cell inoculation. (B) Plasma vs tumor levels of pterostilbene after its i.v. administration (30 mg/kg). (C) Effect of pterostilbene on melanoma cell growth and viability in vitro (15 mM×60 min every 24 h starting 24 h after seeding). (D) Effect of pterostilbene on the rates of tumor cell proliferation and apoptotic death in vivo. For each experimental condition a representative picture is shown: immunohistochemical detection of melanoma cells using HMB45 monoclonal antibodies, cell proliferation detection using anti-Ki-67 monoclonal antibodies, and TUNEL staining showing melanoma cells with apoptotic nuclei. Proliferation and apoptotic indexes (expressed as % of Ki-67- and TUNEL-positive cells relative to controls, respectively) were calculated using ten 10×10-mm$^2$ sections per tumor, and randomly selecting four different areas per section. All data are mean values±SD of 9-10 different animals or experiments. *Significantly different $p<0.01$ comparing Pter-treated mice vs controls.
Figure 1:
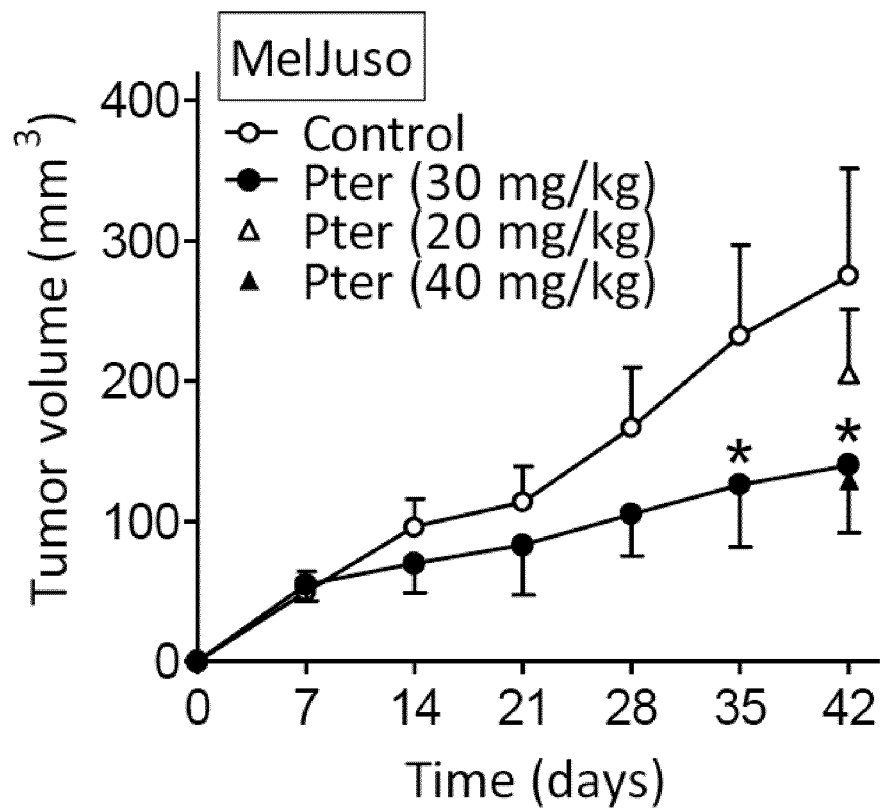
Figure 1:
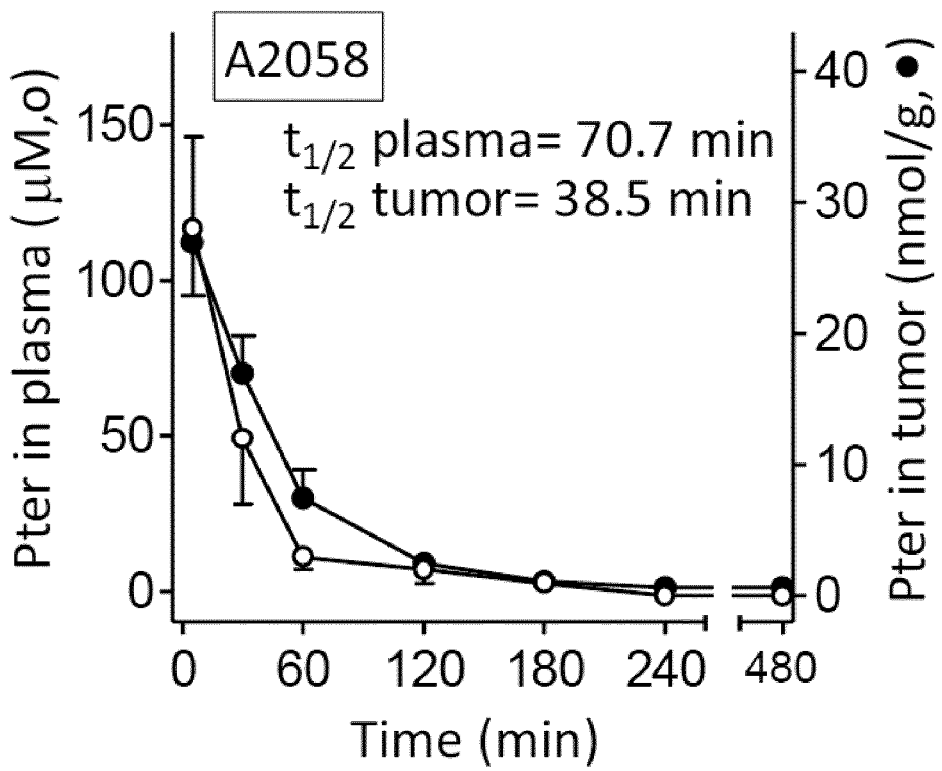
Figure 1:
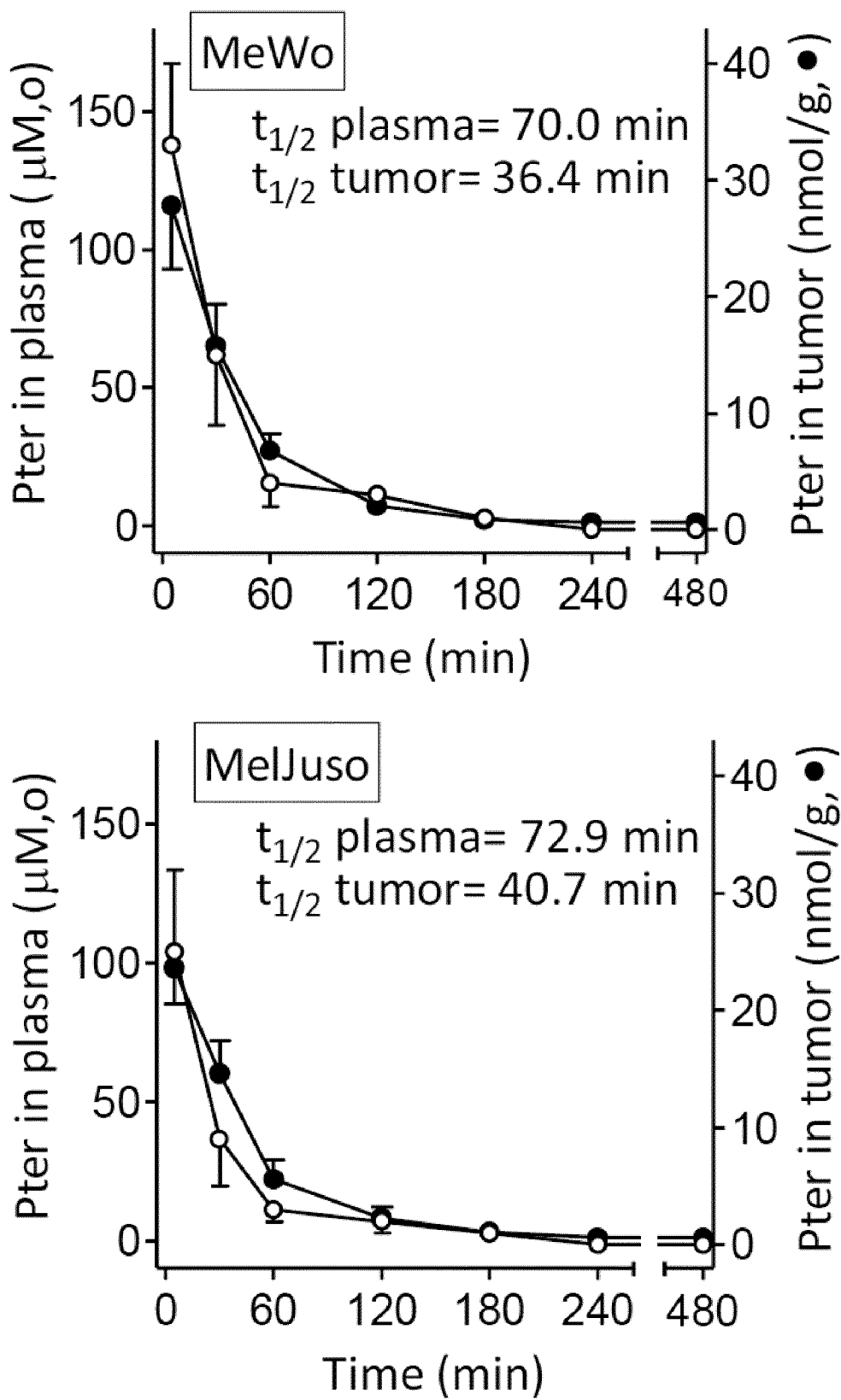
Figure 1:
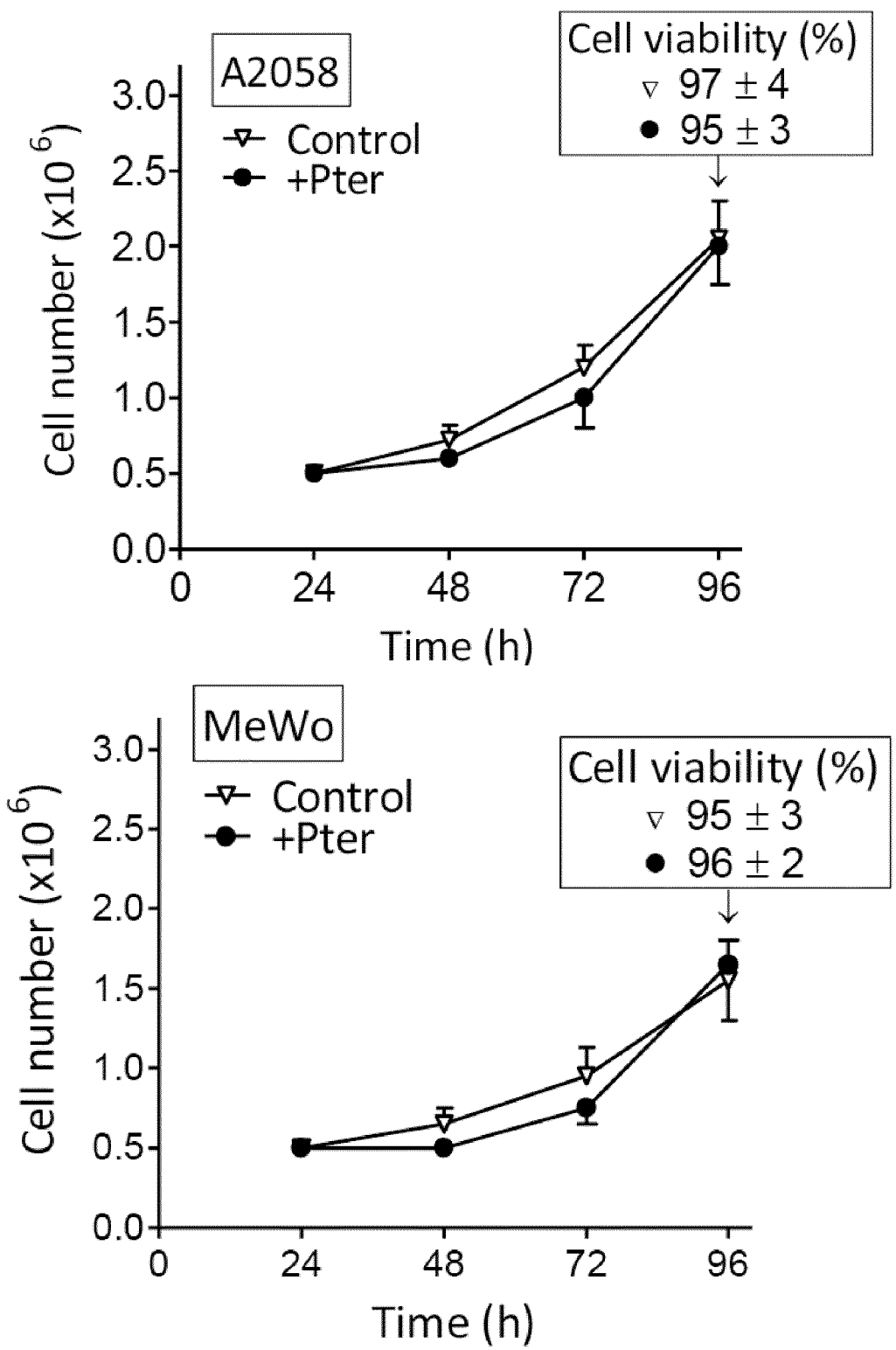
Figure 1:
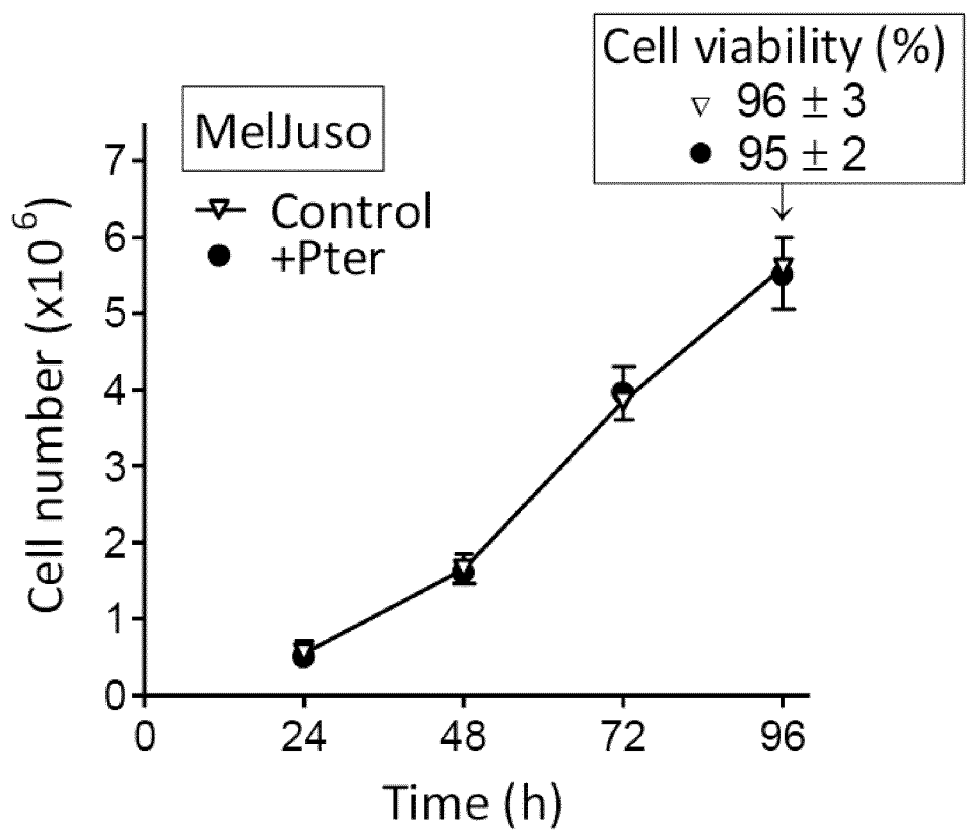
Figure 1:
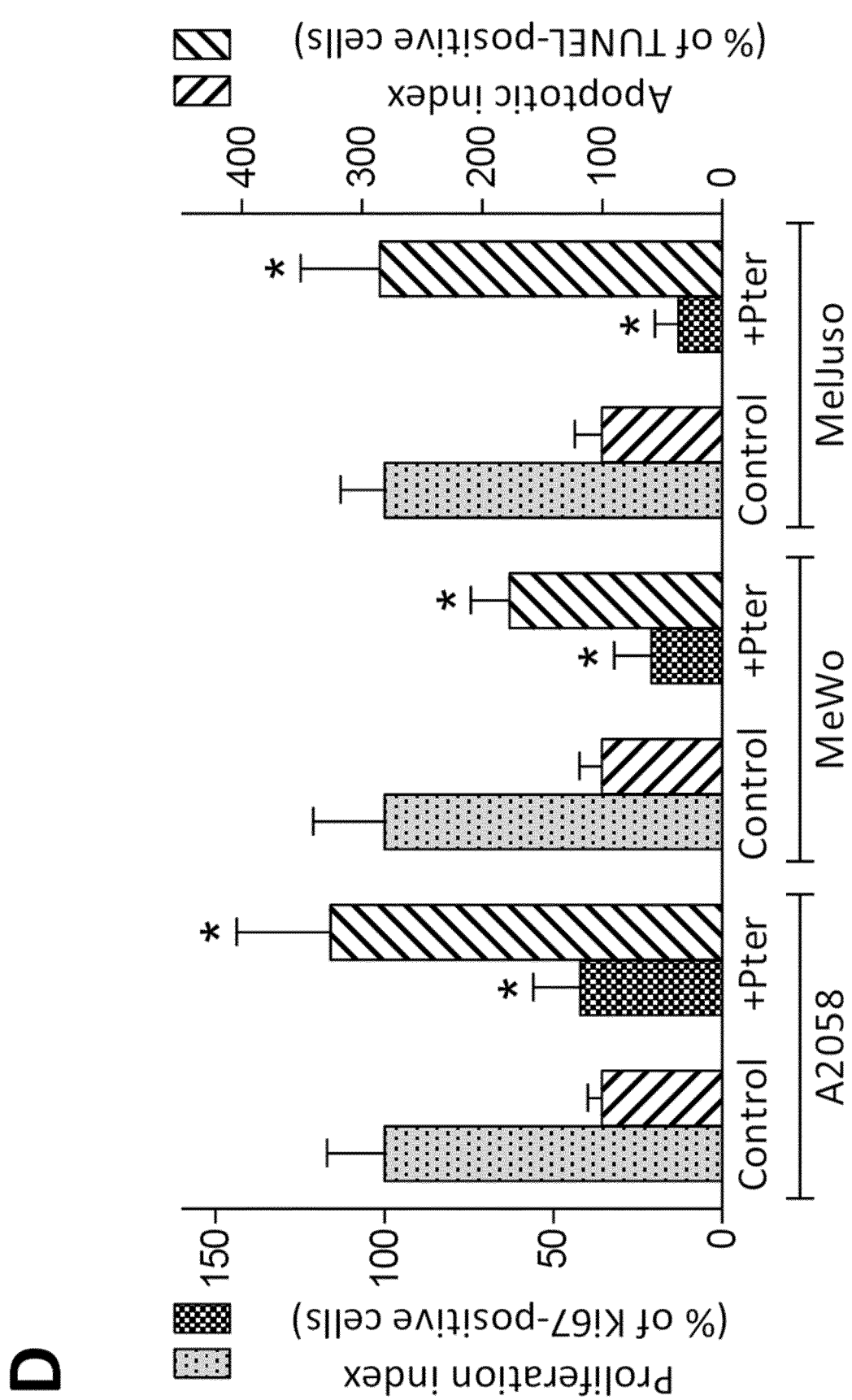

The inventors of the present invention have observed that, surprisingly, the administration of a combination therapy of a glutathione depleting agent, and a chemotherapeutic agent, such as, protein-bound paclitaxel (PAC.PBP) to cultured human cancer cell lines of various origins, such as melanoma cells, isolated from xenografts grown in mice treated with pterostilbene (Pter), lead to an almost complete elimination of the tumor cells, as shown by a decrease in both the cell number and cell viability, showing a clear improvement in the effect between the glutathione depleting agent and the chemotherapeutic agent as compared to the effect of each of these compounds alone (see FIG. 5, FIGS. 18 to 25). In addition, the effect between the glutathione-depleting agent and the chemotherapeutic agent was much less extensive in the absence of pretreatment with pterostilbene (Table 4).

Thus, in an aspect, the present invention refers to a combination comprising (i) pterostilbene, pterostilbene phosphate or a pharmaceutically acceptable salt thereof, (ii) a glutathione depleting agent and (iii) a cancer chemotherapeutic agent.

In another aspect, the invention refers to the combination of the invention for use in medicine. In a further aspect, the invention refers to the combination of the invention for use in the treatment and/or prevention of cancer, wherein pterostilbene, pterostilbene phosphate or a pharmaceutically acceptable salt thereof is administered before the administration of the glutathione depleting agent and the cancer chemotherapeutic agent, and wherein the administration of the glutathione depleting agent starts before the administration of the cancer chemotherapeutic agent.

DETAILED DESCRIPTION OF THE INVENTION

Combination of the Invention

In one aspect, the present invention refers to a combination comprising (i) pterostilbene, pterostilbene phosphate or a pharmaceutically acceptable salt thereof, (ii) a glutathione depleting agent and (iii) a cancer chemotherapeutic agent.

The term "combination", as used herein, refers to a material combination that comprises at least two components, as well as any product resulting, directly or indirectly, from the combination of the different components in any quantity thereof. In the context of the present invention, the term "combination" comprises the following three compounds: (i) pterostilbene, pterostilbene phosphate or a pharmaceutically acceptable salt thereof, (ii) a glutathione depleting agent and (iii) a cancer chemotherapeutic agent, wherein compound (i) is included in a separate formulation from compounds (ii) and (iii), and wherein compounds (ii) and (iii) may be included in the same or separate formulations. The formulations may be combined for joint use as a combined preparation. The combination may be a kit-of-parts wherein each of the components is individually formulated and packaged.

(i) Pterostilbene and Pterostilbene Phosphate

The term "pterostilbene" or "Pter" or "trans-3,5-dimethoxy-4'-hydroxystilbene" as used herein, refers to a compound of formula

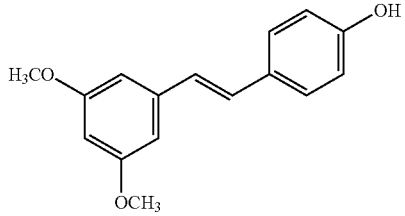 [SMILES: COc1cc(/C=C/c2ccc(O)cc2)cc(OC)c1]

The term "pterostilbene phosphate" refers to a compound of formula

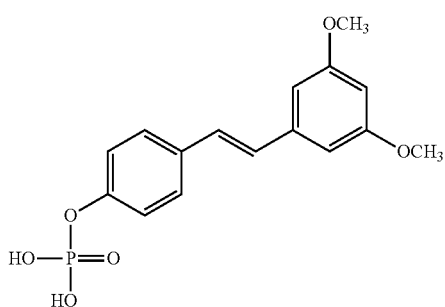 [SMILES: COc1cc(/C=C/c2ccc(OP(=O)(O)O)cc2)cc(OC)c1]

The term "pharmaceutically acceptable salt" refers to any salt of pterostilbene or pterostilbene phosphate which, upon administration to the recipient is capable of providing (directly or indirectly) a compound as described herein. Preferably, as used herein, the term "pharmaceutically acceptable salt" means approved by a regulatory agency of the Federal or a state government or listed in the U.S. Pharmacopeia or other generally recognized pharmacopeia for use in animals, and more particularly in humans. The preparation of salts can be carried out by methods known in the art.

Illustrative non-limitative examples of pharmaceutically acceptable salts include, but are not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate salts. The pharmaceutically acceptable salts of pterostilbene or pterostilbene phosphate are preferably prepared from a polyphenol compound having an acidic functional group, and an acceptable inorganic or organic base. Suitable bases include, but are not limited to, hydroxides of alkali metals such as sodium, potassium, and lithium; hydroxides of alkaline earth metals such as calcium and magnesium; hydroxides of other metals, such as aluminum and zinc; ammonia, and organic amines, such as unsubstituted or hydroxy-substituted mono-, di-, ortri-alkylamines, dicyclohexylamine; tributyl amine; pyridine; N-methyl, N-ethylamine; diethylamine; triethylamine; mono-, bis-, or tris-(2-hydroxy substituted lower alkylamines), such as mono-; bis-, or tris-(2-hydroxyethyl) amine, 2-hydroxy-tert-butylamine, or tris-(hydroxymethyl) methylamine, N,N-di-lower alkyl-N-(hydroxy lower alkyl)- amines, such as N,N-dimethyl-N-(2-hydroxyethyl)amine or tri-(2-hydroxyethyl)amine; N-methyl-0-glucamine; and amino acids such as arginine, lysine, and the like. The term "pharmaceutically acceptable salt" also includes a hydrate of a polyphenol compound. In a particular embodiment, the pharmaceutically acceptable salt is a disodium salt.

In a particular embodiment, the combination comprises pterostilbene phosphate, preferably a disodium salt of pterostilbene phosphate.

(ii) Glutathione Depleting Agent

The term "glutathione depleting agent", as used herein, refers to a substance that reduces or eliminates glutathione from a cell that has been contacted with that substance. The skilled person is able of determining if a particular molecule is a glutathione depleting agent, for example, by comparing the effect of the particular molecule with the effect of buthionine sulfoximine (BSO), a specific inhibitor of gamma-glutamyl-cysteinyl ligase, using the methodoly described for in vitro and in vivo conditions by Terradez P et al, Biochem J 1993, 292 (Pt 2): 477-83. In a particular embodiment, a particular molecule is a glutathione depleting agent if said molecule has at least a 10%, at least a 20%, at least a 30%, at least a 40%, at least a 50%, at least a 60%, at least a 70%, at least a 80%, at least a 90%, a 100% or more of the glutathione-depleting effect of buthionine sulfoximine. Illustrative non-limitative examples of glutathione depleting agents are:

a) A Bcl-2 antisense oligodeoxynucleotide, that is, an oligodeoxynucleotide which is complementary to the RNA sequence of the Bcl-2 gene, as described by Ortega, et al., Cancers (Basel) 2011, 3, 1285-1310. Non-limitative examples of Bcl-2 antisense oligodeoxynucleotides are described in U.S. Pat. No. 5,734,033, WO2003040182A1, U.S. Pat. No. 5,831,066A. Assays for determining if a particular compound is a Bcl-2 antisense oligodeoxynucleotide are, for example, those based on the effect of a compound on the mRNA levels of Bcl-2 or on the Bcl-2 protein levels, as described by Mena et al., Clinical Cancer Research 2007, 13 (9): 2658-66.

b) An inhibitor of multidrug resistance protein 1 (MRP1). As described by Ortega, et al., supra.

The term "MRP1 inhibitor", as used herein, refers to a compound inhibiting the activity of the MRP1. The term inhibitor includes, without limitation, antagonists of MRP1, antibodies against MRP1, compounds which prevent expression of MRP1 and compounds which lead to reduced mRNA or protein levels of the MRP1. Non-limitative examples of an inhibitor of MRP1 are verapamil and MK-571. An assay for determining if a particular compound is a MRP1 inhibitor is, for example, the methodology described in Olson D. P. et al., Cytometry 2001, 46 (2): 105-13.

c) An inhibitor of the gamma-glutamyl transpeptidase or gamma glutamyl transferase (GGTP or GGT), like those described by Silber et al., Anal Biochem 1986, 158 (1): 68-71.

The term "GGTP inhibitor", as used herein, refers to a compound inhibiting the activity of the GGTP, which is an enzyme which catalyzes the transfer of the gamma-glutamyl moiety of glutathione to an acceptor. The term inhibitor includes, without limitation, antagonists of GGTP, antibodies against GGTP, compounds which prevent expression of GGTP and compounds which lead to reduced mRNA or protein levels of the GGTP. GGTP inhibitors include both selective and non-selective (also affecting asparagine synthetase) inhibitors. Non-limitative examples of an inhibitor of GGTP are acividin and 2-amino-4-{[3-(carboxymethyl)phenyl](methyl)phosphono}butanoic acid (GGsTop™). Assays for determining if a particular compound is a GGTP inhibitor are, for example those described by Silver et al., Anal Biochem 1986, 158 (1): 68-71.

d) An inhibitor of cystine uptake, as described by Obrador, et al., *Hepatology* 2002, 35, 74-81.

The term "inhibitor of cystine uptake" refers to a compound inhibiting any of the systems by which extracellular cystine is transported inside the cell, including the sodium-independent $X_c^-$ system and the sodium-dependent XAG system (McBean G. J. and Flynn J., Biochem Soc Trans. 2001, 29 (Pt6): 712-22). The term inhibitor includes both competitive and non-competitive inhibitors. Non-limitative examples of inhibitors of cystine uptake are acivicin, L-glutamate, L-serine-o-sulphate, L-cysteine sulphinate, L-cysteine, L-trans-pyrrolidine-2,4-dicarboxylate and kainite. Assays for determining if a particular compound is an inhibitor of cysteine uptake are, for example, assays based on the determination of the uptake of $^{35}$S-labeled cysteine.

e) Glutathione disulfide (NOV-002), a compound having the formula

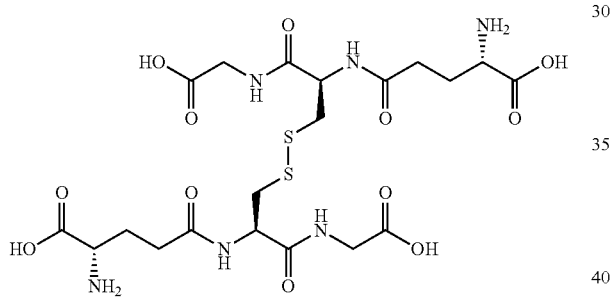

or its disodium salt disodium glutathione disulfide, as described by Gumireddy et al., *J Carcinog Mutagen* 2013 (2013).

f) Phenethyl isothiocyanate, a compound having the formula

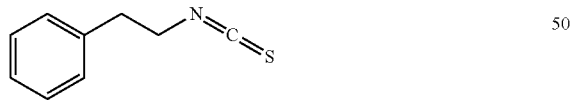

as described by Trachootham, et al., *Cancer Cell* 2006, 10: 241-252.

g) A glucocorticoid receptor antagonist, as described by Min, et al., *J Mol Med (Berl)* 2012, 90: 309-319.

The term "glucocorticoid receptor antagonist" refers to a compound that binds a glucocorticoid receptor and lacks any substantial ability to activate the receptor itself. The term "glucocorticoid receptor antagonist" includes both neutral antagonists and inverse antagonists. A "neutral antagonist" is a compound that blocks the action of the agonist but has no effect on intrinsic or spontaneous receptor activity. An "inverse antagonist" is able to both block the action of the agonist at the receptor and attenuate the constitutive activity of the receptor. The term "antagonist" also includes competitive antagonists, which are drugs that bind to the same site as the natural ligand; noncompetitive antagonists which bind to a different site on the receptor than the natural ligand; reversible antagonists which bind and unbind the receptor at rates determined by receptor-ligand kinetics; and irreversible antagonists which bind permanently to the receptor either by forming a covalent bond to the active site or just by binding so tightly that the rate of dissociation is effectively zero. Non-limitative examples of glucocorticoid receptor antagonists are RU-486 (mifepristone), RU-43044, octahydrophenanthrenes, spirocyclic dihydropyridines, triphenylmethanes and diaryl ethers, chromenes, dibenzyl anilines, dihydroisoquinolines, pyrimidinediones, azadecalins, aryl pyrazolo azadecalins, 11-monoaryl steroids, phenanthrenes, dibenzyl [2.2.2]cycloctanes and derivatives, dibenzoclycloheptanes and their derivatives, dibenzyl anilinesulfonamides and their derivatives, dihetero (aryl) pentanol, chromene derivatives, azadecalins, aryl quinolones, 11,21-bisaryl steroids and 11-aryl, and 16-hydroxy steroids and the dual antagonist-agonists beclomethasone, betamethasone, budesonide, ciclesonide, flunisolide, fluticasone, mometasone, and triamcinolone. Whether a particular compound is a glucocorticoid receptor antagonist can be determined, for example, by commercial kits, like the Glucocorticoid receptor pathway reporter kit (BPS BIOSCIENCE, SAN DIEGO, Calif., USA).

h) An anti-IL-6 agent, as described by Obrador et al. *J Biol Chem* 2011, 286: 15716-15727.

The term "anti-IL-6 agent" refers to a compound which is capable of decreasing the activity of IL-6 either by diminishing its levels, by totally or partially blocking the binding to its receptor or by totally or partially inhibiting its receptor activity. The term "anti-IL-6 agent" includes inhibitory antibodies against IL-6, i.e., antibodies that bind to IL-6 preventing IL-6 to bind to its receptor, like for example elsilimomab and siltuximab, and inhibitors of IL-6 receptor, like tocilizumab. Assays for determining if a particular compound is an anti-IL6 agent are, for example, an ELISA for determining IL6 levels, like the kit of Life Technologies, Carlsbad, Calif., USA, or an assay for determining the intracellular signaling derived from the binding of IL6 to its receptor, like the IL6/STAT3 Signaling Pathway Plus PCR Array de Quiagen (Valencia, Calif., USA).

i) Buthionine sulfoximine (BSO), which is a compound having the formula

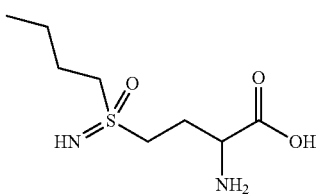

The glutathione depleting effect of BSO has been described by Terradez P. et al., Biochem J. 1993, 292: 477-483.

j) Diethylmaleate or DEM, which is a compound having the formula

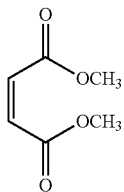

The glutathione depleting effect of DEM has been described by Estrela J. M. et al., Nat Med 1995, 1(1): 84-88.

k) NPD926, a compound having the formula

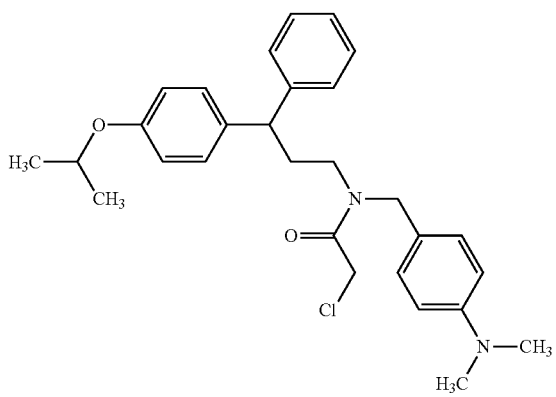 [SMILES: CC(C)Oc1ccc(C(CCN(Cc2ccc(N(C)C)cc2)C(=O)CCl)c2ccccc2)cc1]

The glutathione depleting effect of NPD926 has been described by Kawamura T et al., Biochem J 2014, 463: 53-63.

l) Parthenolide, a compound having the formula

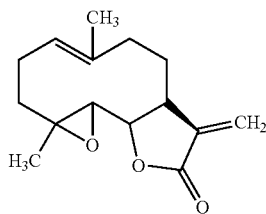

The glutathione depleting effect of parthenolide has been described by Pei S. et al., J Biol Chem 2013, 288 (47): 33542-58.

m) A compounds having the formula

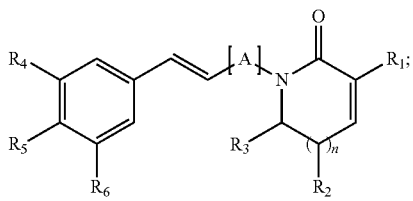

wherein A is C(O) or S(O)2; wherein n=0, 1, 2, or 3; wherein the ortho-carbon of the phenyl ring is unsubstituted or substituted with a halogen; wherein R1 is selected from the group consisting of hydrogen, halogen, C≡C-alkyl, C≡C-cycloalkyl, C≡C-cycloakyl halide, C≡C-aryl, C≡C-aryl halide, and an aryl group; wherein R2 is selected from the group consisting of hydrogen, alkyl, alkenyl, and an aryl group; wherein R3 is selected from the group consisting of hydrogen, alkyl, alkenyl, and an aryl group; and, wherein each of R4, R5, and R6 is independently selected from the group consisting of hydrogen, bromine, chlorine, fluorine, keto, hydroxyl, alkyl, alkenyl, alkoxy, methoxy, aminoalkyl, aminoalkenyl, and an aminoalkoxy group.

In particular, Piperlongumine, a compound having the formula

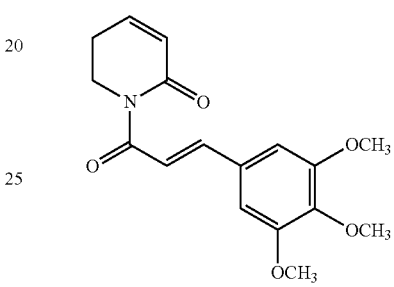

The glutathione depleting effect of piperlongumine has been described by Pei S. et al., supra.

n) An inhibitor of a protein from the bromodomain and extraterminal domain family as described by Shao Q. et al., Cancer Research 2014, 74 (23):7090-102. The term "inhibitor of a protein from the bromodomain and extraterminal (BET) domain family" or "BET inhibitor" refers to a compound which binds the bromodomain of bromodomain and extraterminal (BET) proteins BRD2, BRD3, BRD114 and BRDT preventing protein-protein interaction between BET proteins and acetylated histones and transcription factors. The term "BET inhibitor" includes inhibitors targeting any of BRD2, BRD3, BRD4 and BRDT. Non-limitative examples of BET inhibitors are JQ1, GSK525762A and OTX-015. Assays for determining if a particular compound is a BET inhibitor are, for example, the Homogeneous Proximity Assay from BioTek (Winooski, Vt., USA) for screening inhibitors of BRD4.

In a particular embodiment, the glutathione depleting agent of the combination of the invention is selected from the group consisting of: a) a Bcl-2 antisense oligodeoxynucleotide; b) an inhibitor of multidrug resistance protein 1; c) an inhibitor of the gamma-glutamyl transpeptidase; d) an inhibitor of cystine uptake; e) disodium glutathione disulfide; f) phenethyl isothiocyanate; g) a glucocorticoid receptor antagonist; h) an anti-IL-6 agent; i) buthionine sulfoximine; j) diethylmaleate; k) NPD926; l) parthenolide; m) piperlongumine and n) an inhibitor of a protein from the bromodomain and extraterminal domain family, in particular GSK525762A or I-BET762.

In a more particular embodiment the inhibitor of multidrug resistance protein 1 is verapamil, which is a compound having the formula

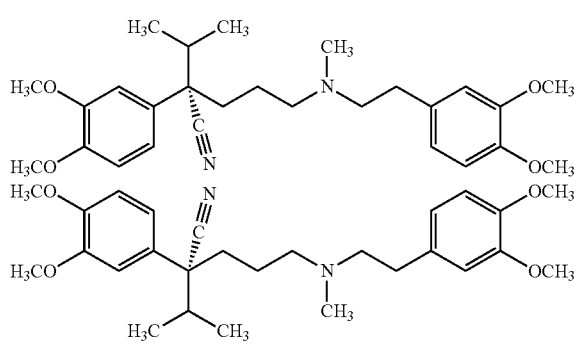

In a more particular embodiment, the inhibitor of gamma-glutamil transpeptidase is acivicin, which is a compound having the formula

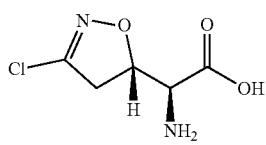 [SMILES: N[C@H](C(=O)O)[C@@H]1CC(Cl)=NO1]

In a more particular embodiment, the inhibitor of cystine uptake is sulfasalazine, which is a compound having the formula

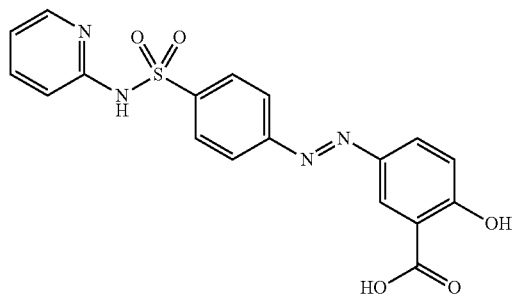 [SMILES: O=C(O)c1cc(/N=N/c2ccc(S(=O)(=O)Nc3ccccn3)cc2)ccc1O]

In a more particular embodiment, the glucocorticoid receptor antagonist is RU-486 or mifepristone, which is a compound having the formula

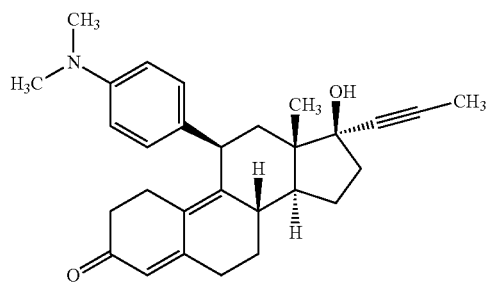

In a more particular embodiment, the anti-IL-6 agent is an inhibitory antibody against IL-6 or an inhibitor of the IL-6 receptor. In an even more particular embodiment, the anti-IL-6 agent is selected from the group consisting of tocilizumab, elsilimomab and siltuximab. The term "tocilizumab" refers to a humanized monoclonal antibody against the IL-6 receptor. The term "elsilimomab" refers to a mouse monoclonal antibody against IL-6. The term "siltuximab" or "CNTO 328" refers to a chimeric monoclonal antibody against IL-6.

In a more particular embodiment, the inhibitor of a protein from the bromodomain and extraterminal domain family is selected from the group consisting of JQ1, GSK525762A and OTX-015. The term "JQ1" refers to a compound of formula

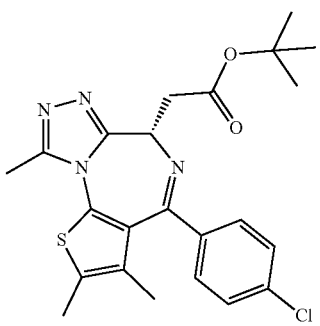 [SMILES: Cc1sc2c(c1C)C(c1ccc(Cl)cc1)=N[C@@H](CC(=O)OC(C)(C)C)c1nnc(C)n1-2]

The term "GSK525762A" refers to a compound of formula

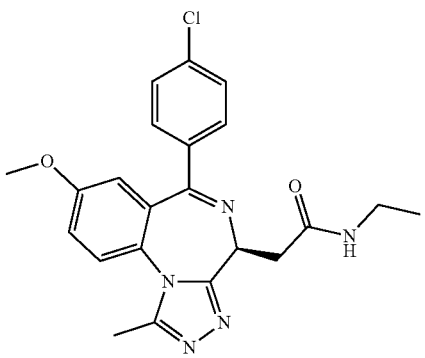 [SMILES: CCNC(=O)C[C@@H]1N=C(c2ccc(Cl)cc2)c2cc(OC)ccc2-n2c(C)nnc21]

The term "OTX-015" refers to a compound of formula

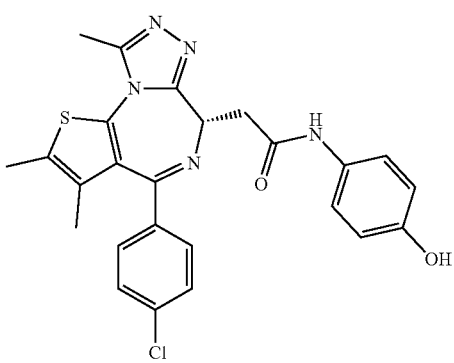 [SMILES: Cc1sc2c(c1C)C(c1ccc(Cl)cc1)=N[C@@H](CC(=O)Nc1ccc(O)cc1)c1nnc(C)n1-2]

The term "CPI-0610" refers to the compound of reference CAT#: 206117 markered by MedKoo Biosciencies Inc.

In a particular embodiment, the glutathione depleting agent is diethylmaleate, GSK525762A (I-BET762) or piperlongumine.

(iii) Cancer Chemotherapeutic Agent

The term "cancer chemotherapeutic agent", as used herein, refers to an agent that at least partially inhibits the development or progression of a cancer, including inhibiting in whole or in part symptoms associated with the cancer.

The term "cancer", a used herein, refers to a disease characterized by uncontrolled cell division (or by an increase of survival or apoptosis resistance) and by the ability of said cells to invade other neighbouring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis. As used herein, the term cancer includes, but is not limited to, the following types of cancer: breast cancer; biliary tract cancer; bladder cancer; brain cancer including glioblastomas, in particular glioblastoma multiforme, and medulloblastomas; cervical cancer; head and neck carcinoma; choriocarcinoma; colon cancer, colorectal cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer, hepatoma; lung cancer, pleural mesothelioma; lymphomas including Hodgkin's disease and lymphocytic lymphomas; neuroblastomas; oral cancer including squamous cell carcinoma; parotid gland cancer; ovarian cancer including those arising from epithelial cells, stromal cells, germ cells and mesenchymal cells; pancreatic cancer; prostate cancer; kidney cancer, suprarenal cancer; rectal cancer; sarcomas including leiomyosarcoma, rhabdomyo sarcoma, liposarcoma, fibrosarcoma, and osteosarcoma; skin cancer including melanoma, Merkel cell carcinoma, Kaposi's sarcoma, basal cell carcinoma, and squamous cell cancer; cervix cancer, endometrial cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill in the art.

In a particular embodiment of the invention, the cancer is melanoma, pancreas carcinoma or glioblastoma multiforme.

In a particular embodiment, the cancer is melanoma. The term "melanoma", as used herein, refers to a malignant skin tumour of melanocytes and includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, modular melanoma, lentigo malignant melanoma, acral lentiginous melanoma, invasive melanoma and familial atypical mole and melanoma (FAM-M) syndrome. Moreover, the term "melanoma" refers not only to primary melanomas but also to "melanoma metastasis" which, as used herein, refers to the spread of melanoma cells to regional lymph nodes and/or distant organs. This event is frequent, given that melanomas contain multiple cell populations characterized by diverse growth rates, karyotypes, cell-surface properties, antigenicity, immunogenicity, invasion, metastasis, and sensitivity to cytotoxic drugs or biologic agents. Melanoma shows frequent metastasis to brain, lungs, lymph nodes, and skin. Thus, the combinations of the invention are also useful for the treatment of melanoma metastasis.

In a particular embodiment, the cancer is pancreas carcinoma. The term "pancreas carcinoma", as used herein, refers to abnormal or un-regulated cell growth affecting the pancreas. The term "pancreatic carcinoma" includes exocrine carcinoma, endocrine carcinoma and neuroendocrine carcinoma. Illustrative non-limitative examples of pancreatic carcinoma are pancreatic adenocarcinoma, acinar cell carcinoma, cystadenocarcinomas and pancreatic mucinous cystic neoplasms.

In a particular embodiment the cancer is glioblastoma multiforme. The term "glioblastoma multiforme" or "GBM" as used, herein, refers to a type of primary brain tumor. GBM is an anaplastic, highly cellular tumor with poorly differentiated, round, or pleomorphic cells, occasional multinucleated cells, nuclear atypia, and anaplasia. Variants of the tumor include gliosarcoma, multifocal GBM, or gliomatosis cerebri (in which the entire brain may be infiltrated with tumor cells). GBM seldomly metastasizes to the spinal cord or outside the nervous system. GBM is graded by their microscopic and histological appearance. Generally, grade I (pilocytic astrocytomas) and grade II (benign astrocytomas) tumors grow slowly over many years while grade IV (GBM) grows rapidly, invading and altering brain function.

The term "cancer chemotherapeutic agent" includes standard chemotherapy drugs, which generally attack any quickly dividing cell, targeted therapy agents and immunomodulatory agents.

Illustrative non-limitative examples of cancer chemotherapeutic agents which may be in accordance to the present invention include: alkylating agents such as nitrogen mustards/oxazaphosphorines (e.g. cyclophosphamide, ifosfamide), nitrosoureas (e.g. carmustine), triazenes (e.g. temozolamide), and alkyl sulfonates (e.g. busulfan); antimetabolite drugs (for example 5-fluorouracil, capecitabine, 6-mercaptopurine, methotrexate, gemcitabine, cytarabine, fludarabine or pemetrexed); anthracycline antibiotics such as doxorubicin and daunorubicin, taxans such as Taxol™ and docetaxel, vinca alkaloids such as vincristin and vinblastine, 5-fluorouracil (5-FU), leucovorin, irinotecan, idarubicin, mitomycin C, oxaliplatin, raltitrexed, pemetrexed, tamoxifen, cisplatin, carboplatin, methotrexate, actinomycin D, mitoxantrone, blenoxane, mithramycin, paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, penicillamine, PTK787/ZK 222584, RPI.4610, squalamine lactate, SU5416, thalidomide, combretastatin, COL-3, neovastat, BMS-275291, SU6668, anti-VEGF antibodies, Medi-522 (Vitaxin II), CAI, Interleukin 12, IM862, amiloride, angiostatin, angiostatin K1-3, angiostatin K1-5, captopril, DL-alpha-difluoromethylornithine, DL-alpha-difluoromethylornithine HCl, endostatin, fumagillin, herbimycin A, 4-hydroxyphenylretinamide, juglone, laminin, laminin hexapeptide, laminin pentapeptide, lavendustin A, medroxyprogesterone, minocycline, placental ribonuclease inhibitor, suramin, thrombospondin, antibodies targeted against proangiogenic factors (for example, bevacizumab, cetuximab, panitumumab, trastuzumab); topoisomerase inhibitors; antimicrotubule agents; low molecular weight tyrosine kinases inhibitors of proangiogenic growth factors (for example erlotinib, sorafenib, sunitinib, gefitinib);

GTPase inhibitors; histone deacetylase inhibitors; AKT kinase or ATPase inhibitors; Wnt signaling inhibitors; inhibitors of the E2F transcription factor; mTOR inhibitors (for example temsirolimus); alpha, beta and gamma interferon, IL-12, matrix metalloproteinase inhibitors (for example, COL3, Marimastat, Batimastat); ZD6474, SU11248, vitaxin; PDGFR inhibitors (for example imatinib); NM3 and 2-ME2; cyclic peptides such as cilengitide. Other chemotherapy agents suitable are described in detail in The Merck Index in CD-ROM, 13$^{th}$ Edition. In a preferred embodiment of the invention, chemotherapeutic agents are selected from the group consisting of docetaxel (Taxotere®), cisplatin, pemetrexed, gemcitabine and irinotecan.

In a particular embodiment, the cancer chemotherapeutic agent is a taxane, preferably comprises or consists on paclitaxel. The term "paclitaxel", as used herein, refers to a compound with chemical name (2α,4α,5β,7β,10β,13α)-4, 10-Bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate and having the chemical formula

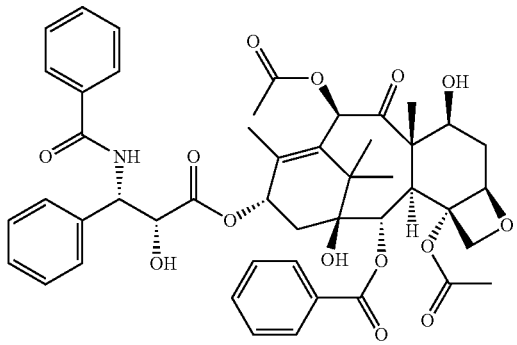 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

In a more particular embodiment, the paclitaxel is protein bound paclitaxel. The term "protein-bound paclitaxel" or "nab-paclitaxel" or "nanoparticle albumin-bound paclitaxel", as used herein, refers to a formulation in which paclitaxel is bound to albumin as a delivery vehicle.

The cancer chemotherapeutic agent will vary depending on the type of cancer that is going to be treated with the combination of the invention. The skilled person can determine which cancer chemotherapeutic agent is more suitable to treat a particular type of cancer. Therefore, in a particular embodiment the cancer chemotherapeutic agent is a melanoma chemotherapeutic agent. Illustrative non-limitative examples of melanoma chemotherapeutic agents are:
1. Targeted drugs: inhibitors of signal transduction.
    BRAF inhibitors: vemurafenib, dabrafenib, trametinib.
    C-kit inhibitors: imatinib, nilotinib.
    MEK inhibitors: trametinib.
2. Immunomodulatory agents
    PD-1 inhibitors: pembrolizumab and nivolumab
    CTLA-4 inhibitors: ipilimumab
    Cytokines: interferon alpha and IL-2
    Bacille Calmette-Guerin (BCG) vaccine
    Imiquimod
3. Standard chemotherapy drugs: Dacarbazine (also called DTIC), Temozolomide, Nab-paclitaxel, Paclitaxel, Carmustine (also known as BCNU), Cisplatin, Carboplatin, Vinblastine.

In a particular embodiment, the combination of the invention comprises pterostilbene, pterostilbene phosphate or a pharmaceutically acceptable salt thereof, diethylmaleate and paclitaxel, preferably protein bound paclitaxel.

Thus, in a particular embodiment, the combination of the invention does not comprise a glucocorticoid. The term "glucocorticoid", as used herein, refers to any steroid that can bind and activate the glucocorticoid receptor. In a more particular embodiment, the combination of the invention does not comprise corticosterone. The term "corticosterone", as used herein, refers to a compound of formula

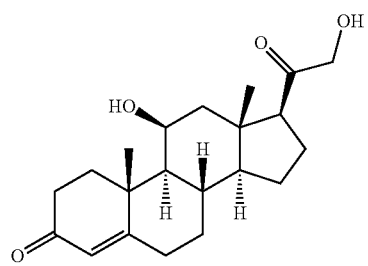

In a particular embodiment, the combination of the invention comprises pterostilbene, pterostilbene phosphate or a pharmaceutically acceptable salt thereof, a glutathione depleting agent and a cancer chemotherapeutic agent as sole therapeutic agents. The term "therapeutic agent", as used herein, refers to an agent useful in the treatment of a disease. A compound that has no effect on the prevention and/or treatment of cancer is not considered a therapeutic agent in the context of the present invention. In a particular embodiment, the combination of the invention comprises pterostilbene, a glutathione depleting agent and a cancer chemotherapeutic agent as sole cancer therapeutic agents.

According to the combination of the invention, pterostilbene, pterostilbene phosphate or a pharmaceutically acceptable salt thereof is included in a separate formulation from the glutathione depleting agent and the cancer chemotherapeutic agent. In a more particular embodiment, each one of pterostilbene, pterostilbene phosphate or a pharmaceutically acceptable salt thereof, the glutathione depleting agent and the cancer chemotherapeutic agent is included in separate independent formulations, i.e., pterostilbene, pterostilbene phosphate or a pharmaceutically acceptable salt thereof is included in one formulation, the glutathione depleting agent is included in other formulation and the cancer chemotherapeutic agent is included in other formulation.

Each of the formulations includes a pharmaceutically acceptable carrier. The terms "pharmaceutically acceptable carrier", or "pharmaceutically acceptable excipient," "pharmaceutically acceptable diluent,", or "pharmaceutically acceptable vehicle," used interchangeably herein, refer to a non-toxic solid, semisolid or liquid filler, diluent, encapsulating material or formulation auxiliary of any conventional type.

A pharmaceutically acceptable carrier is essentially non-toxic to recipients at the dosages and concentrations employed, and is compatible with other ingredients of the formulation. Suitable carriers include, but are not limited to water, dextrose, glycerol, saline, ethanol, and combinations thereof. The carrier can contain additional agents such as wetting or emulsifying agents, pH buffering agents.

Each of the components of the combination may be administered by a different route or by the same route.

In a particular embodiment, any of the formulations of pterostilbene, pterostilbene phosphate or a pharmaceutically acceptable salt thereof, the glutathione depleting agent and the cancer chemotherapeutic agent is a formulation for parenteral administration. Thus, said formulation suitable for parenteral injection, include physiologically acceptable sterile aqueous or non-aqueous solutions, dispersions, suspensions or emulsions, or may comprise sterile powders for reconstitution into sterile injectable solutions or dispersions. Examples of suitable aqueous or non-aqueous excipients or carriers, diluents, solvents or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. In a more particular embodiment, any of the formulations of pterostilbene, pterostilbene phosphate or a pharmaceutically acceptable salt thereof, the glutathione depleting agent and the cancer chemotherapeutic agent is a formulation for intravenous, intraperitoneal, intramuscular or subcutaneous administration. Typically, formulations for intravenous, intraperitoneal, intramuscular or subcutaneous administration are solutions in sterile isotonic aqueous buffer. If necessary, the formulation also includes a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachet indicating the quantity of active ingredient. Where the formulation is to be administered by infusion, it can be dispensed with an infusion bottle containing sterile pharmaceutical grade water or saline. Where the formulation is administered by injection, an ampule of sterile water for injection or saline can be provided so that the ingredients may be mixed prior to administration. In an even more particular embodiment, the formulation of the invention is a formulation for intravenous or intraperitoneal administration.

In another particular embodiment, any of the formulations of pterostilbene, pterostilbene phosphate or a pharmaceutically acceptable salt thereof, the glutathione depleting agent and the cancer chemotherapeutic agent is a formulation for oral administration.

Solid dosage forms for oral administration include conventional capsules, sustained release capsules, conventional tablets, sustained-release tablets, chewable tablets, sublingual tablets, effervescent tablets, pills, suspensions, powders, granules and gels. In the solid dosage forms, the active ingredients (i.e., pterostilbene, pterostilbene phosphate or a pharmaceutically acceptable salt thereof, the glutathione depleting agent and the cancer chemotherapeutic agent) are admixed with at least one suitable excipient or carrier, such as sodium citrate or dicalcium phosphate or (a) fillers or extenders, such as for example, starches, lactose, sucrose, mannitol, or silicic acid; (b) binders, such as for example, carboxymethylcellulose, alginates, gelatin, polyvinylpyrrolidone, sucrose, or acacia; (c) humectants, such as for example, glycerol; (d) disintegrating agents, such as for example, agar-agar, calcium carbonate, potato or tapioca starch, alginic acid, certain complex silicates, or sodium carbonate; (e) solution retarding agents, such as for example, paraffin; (f) absorption accelerators, such as for example, quaternary ammonium compounds; (g) wetting agents, such as for example, cetyl alcohol or glycerol monostearate; (h) adsorbents, such as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents. Solid formulations of a similar type may also be used as fillers in soft or hard filled gelatin capsules using excipients such as lactose or milk sugar, as well as high molecular weight polyethylene glycols, and the like. Solid dosage forms such as coated tablets, capsules and granules can be prepared with coatings or shells, such as enteric coatings and others known in the art. They may also contain opacifying agents, and can be formulated such that they release the active ingredient or ingredients in a delayed manner. Examples of embedding formulations that can be used are polymeric substances and waxes. The active ingredients can also be in micro-encapsulated form, if appropriate, with one or more of the aforementioned excipients.

Liquid dosage forms for oral administration include pharmaceutically acceptable emulsions, solutions, suspensions, syrups and elixirs containing suitable excipients or carriers used in the art. In addition to the active ingredients (i.e., pterostilbene, pterostilbene phosphate or a pharmaceutically acceptable salt thereof, the glutathione depleting agent and the cancer chemotherapeutic agent), the liquid dosage form may contain one or more excipients or carriers commonly used in the art, such as water or other solvents, solubilizing agents and emulsifiers, such as for example, ethyl alcohol, isopropyl alcohol, ethyl carbonate, ethyl acetate, benzyl alcohol, benzyl benzoate, propylene glycol, 1,3-butylene glycol, dimethylformamide, oils, particular cottonseed oil, groundnut oil, corn germ oil, olive oil, castor oil, sesame seed oil, Miglyol®, glycerol, tetrahydrofurfuryl alcohol, polyethylene glycols, fatty acid esters of sorbitan, or mixtures of these substances, and the like. In addition to said inert diluents, the formulation can also include adjuvants, such as wetting agents, emulsifying and suspending agents, sweetening agents, flavoring agents and perfuming agents. Suspensions, in addition to the active ingredient or ingredients, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Sustainable-release forms and appropriate materials and methods for their preparation are described in the art. In a particular embodiment, the orally administrable form of the formulation is in a sustained release form that further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of them. Enteric coatings may be applied using conventional processes known to experts in the art.

Therapeutic Uses of the Invention

In another aspect, the invention relates to the combination of the invention for use in medicine. Alternatively, the invention relates to the use of the combination of the invention for the manufacture of a medicament.

In another aspect, the invention relates to the combination of the invention for use in the treatment and/or prevention of cancer, wherein the administration of pterostilbene, pterostilbene phosphate or a pharmaceutically acceptable salt thereof starts before the administration of the glutathione depleting agent and the cancer chemotherapeutic agent. Alternatively, the invention relates to the use of the combination of the invention for the manufacture of a medicament for the treatment and/or prevention of cancer, wherein the administration of pterostilbene, pterostilbene phosphate or a pharmaceutically acceptable salt thereof starts before the administration of the glutathione depleting agent and the cancer chemotherapeutic agent. Still alternatively, the invention relates to a method of treatment and/or prevention of cancer in a subject comprising administering to said subject a therapeutically effective amount of the combination of the invention, wherein the administration of pterostilbene, pterostilbene phosphate or a pharmaceutically acceptable salt thereof starts before the administration of the glutathione depleting agent and the cancer chemotherapeutic agent and wherein the administration of the glutathione depleting agent starts before the administration of the cancer chemotherapeutic agent.

In a further particular embodiment, the invention relates to the combination of the invention for use in the treatment and/or prevention of cancer, according to the previous paragraph, wherein the cancer is selected from the list consisting of melanoma, lung, pancreatic, hepatic, ovarian, prostate, colorectal and breast cancer.

The term "therapeutically effective amount", as used herein in relation to the combination of the invention, relates to the sufficient amount of said combination to provide the desired effect, i.e. to achieve an appreciable prevention, cure, delay, reduction of severity or amelioration of one or more symptoms derived from a cancer, and will generally be determined by, among other causes, the characteristics of the agent itself and the therapeutic effect to be achieved. It will also depend on the subject to be treated, the severity of the disease suffered by said subject, the chosen dosage form, etc. For this reason, the doses mentioned in this invention must be considered only as guides for the person skilled in the art, who must adjust the doses depending on the aforementioned variables. In an embodiment, the effective amount produces the amelioration of one or more symptoms of the disease that is being treated.

In a particular and preferred embodiment, the administration of pterostilbene, pterostilbene phosphate or a pharmaceutically acceptable salt thereof starts first and, after a period of time and once the administration of pterostilbene, pterostilbene phosphate or a pharmaceutically acceptable salt thereof has finished, the administration of glutathione and/or the cancer chemotherapeutic agent starts, preferably the administration of the glutathione depleting agent starts before the administration of the cancer chemotherapeutic agent. In an alternative particular embodiment, the administration of pterostilbene, pterostilbene phosphate or a pharmaceutically acceptable salt thereof overlaps in time with the administration of the glutathione depleting agent. In this particular embodiment, the administration of pterostilbene, pterostilbene phosphate or a pharmaceutically acceptable salt thereof starts first and, after a period of time, the administration of the glutathione depleting agent begins while the administration of pterostilbene, pterostilbene phosphate or a pharmaceutically acceptable salt thereof goes on. In a further alternative particular embodiment, the administration of pterostilbene, pterostilbene phosphate or a pharmaceutically acceptable salt thereof overlaps in time with the administration of the glutathione depleting agent and the cancer chemotherapeutic agent. In this further particular embodiment, the administration of pterostilbene, pterostilbene phosphate or a pharmaceutically acceptable salt thereof starts first and, after a period of time, the administration of the glutathione depleting agent and the cancer chemotherapeutic agent begins while the administration of pterostilbene, pterostilbene phosphate or a pharmaceutically acceptable salt thereof goes on.

In a particular embodiment, the glutathione depleting agent is administered in one dose or more doses at intervals of at least, 1 hour, at least 2 hours, at least 4 hours, at least 6 hours, at least 12, at least 24 hours, at least 48 hours, at least 72 hours or more.

In a particular embodiment, the glutathione depleting agent is administered at least 12 hours, at least 24 hours, at least 30 hours, at least 36 hours, at least 2 days, at least 4 days, at least 6 days, at least 1 week, at least 2 weeks, at least 3 weeks, at least 4 weeks, at least 5 weeks, at least 6 weeks . . . after the administration of pterostilbene, pterostilbene phosphate or a pharmaceutically acceptable salt thereof starts.

In a particular embodiment, the cancer chemotherapeutic agent, preferably paclitaxel, more preferably protein bound paclitaxel, is administered at least 1 hour, at least 2 hours, at least 3 hours, at least 6 hours, at least 12 hours, at least 24 hours, at least 48 hours, at least 3 days, at least 4 days, at least 6 days, at least 1 week, at least 2 weeks, at least 3 weeks, at least 4 weeks, at least 5 weeks, at least 6 weeks or more after the administration of the pterostilbene, pterostilbene phosphate or a pharmaceutically acceptable salt thereof starts. In a more particular embodiment, the cancer chemotherapeutic agent is administered 24 hours after the administration of pterostilbene, pterostilbene phosphate or a pharmaceutically acceptable salt thereof starts.

In a particular embodiment, the glutathione depleting agent, is administered at least 1 hour, at least 2 hours, at least 3 hours, at least 4 hours, at least 6 hours, at least 12 hours, at least 1 day, at least 2 days or more after the administration of the cancer chemotherapeutic agent, preferably paclitaxel, even more preferable protein bound paclitaxel, starts. In a more particular embodiment, the glutathione depleting agent is administered 6 hours after the administration of the cancer chemotherapeutic agent, preferably paclitaxel, even more preferable protein bound paclitaxel starts.

In a particular embodiment, the cancer chemotherapeutic agent, preferably paclitaxel, even more preferable protein bound paclitaxel, is administered at least 1 hour, at least 2 hours, at least 3 hours, at least 4 hours, at least 6 hours, at least 12 hours, at least 1 day after the administration of the glutathione depleting agent, preferably diethylmaleate, GSK525762A (I-BET762) or piperlongumine starts.

In a further particular embodiment, administration of the glutathione depleting agent starts at least 12 hours, at least 24 hours, at least 30 hours, at least 36 hours, at least 2 days, at least 4 days, at least 6 days, at least 1 week, at least 2 weeks, at least 3 weeks, at least 4 weeks, at least 5 weeks, at least 6 weeks . . . after the administration of pterostilbene, pterostilbene phosphate or a pharmaceutically acceptable salt thereof starts. In this particular embodiment, the administration of the glutathione depleting agent starts before the administration of the cancer chemotherapeutic agent, preferably at least 1 hour, at least 2 hours, at least 3 hours, at least 4 hours, at least 6 hours, at least 12 hours, at least 1 day, at least 2 days, 3 days, 4 days, 1 week, 2 weeks, 3 weeks, 4 weeks . . . before the administration of the chemotherapeutic agent. It is noted that in this particular embodiment, the administration of pterostilbene, pterostilbene phosphate or a pharmaceutically acceptable salt thereof can overlap in time with the administration of the glutathione depleting agent and can overlap in time with the administration of the glutathione depleting agent and the cancer chemotherapeutic agent. It is further noted, that the administration of the glutathione depleting agent can overlap in time with the administration of the cancer chemotherapeutic agent.

As used herein, the term "treatment" refers to therapeutic measures and prophylactic or preventive measures, wherein the object is to prevent or slow down (lessen) an undesired physiological change or disorder, such as cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the terms "prevent", "prevention" and "preventing" refer to the reduction in the risk of acquiring or developing a given disease or disorder, e.g., cancer, or the reduction or inhibition of the recurrence or a disease or disorder, e.g., cancer.

The term "subject" or "patient", as used herein, refers to any animal, preferably a mammal and includes, but is not limited to, domestic and farm animals, primates, and humans, for example, human beings, non-human primates, cows, horses, pigs, sheep, goats, dogs, cats, or rodents like rats and mice. In a preferred embodiment, the subject is a human being of any age or race. In a particular embodiment, the subject suffers from cancer. In a more particular embodiment, the subject suffers from melanoma.

The term "cancer" has been defined previously in the context of the combination of the invention. In a particular embodiment of the invention, the cancer is melanoma, pancreas carcinoma or glioblastoma multiforme; more preferably is melanoma.

According to the combination for use in the treatment and/or prevention of cancer of the invention, the administration of pterostilbene, pterostilbene phosphate or a pharmaceutically acceptable salt thereof starts before the administration of the glutathione depleting agent and the cancer chemotherapeutic agent, wherein the glutathione depleting agent and the cancer chemotherapeutic agent can be administered either separately or simultaneously. When the glutathione depleting agent and the cancer chemotherapeutic agent are administered separately, the glutathione depleting agent and the cancer chemotherapeutic agent can be administered in any order. Thus, in a particular embodiment, the administration of the glutathione depleting agent starts before the administration of the cancer chemotherapeutic agent. In another particular embodiment, the administration of the cancer chemotherapeutic agent starts before the administration of the glutathione depleting agent. Anyhow, it is much preferred that the administration of the glutathione depleting agent starts before the administration of the cancer chemotherapeutic agent.

The combination of the invention can be administered by any suitable administration route, such as, but not limited to, parenteral, oral, topical, nasal, rectal route. In a particular embodiment, the combination is administered for parenteral route, preferably by intravenous route. Parenteral administration includes, for example, intravenous, intramuscular, intraarterial, intraperitoneal, intranasal, intravaginal, intravesical (e.g., to the bladder), intradermal, transdermal, topical, or subcutaneous administration. The different components of the combination can be administered by different routes, for example, pterostilbene, pterostilbene phosphate or a pharmaceutically acceptable salt can be administered by a first route, and the glutathione depleting agent and the cancer chemotherapeutic agent by a second different route.

In addition, the glutathione depleting agent and the cancer chemotherapeutic agent can also be administered by different administration routes.

Compositions for oral formulations useful for delivering any or all of the components of the combination of the invention are known in the art. In this sense, any of these components can be orally administered, for example, with an inert diluents or with an assimilable edible carrier, or it can be enclosed in hard or soft shell gelatin capsules, or it can be compressed into tablets, or it can be incorporated directly with the food of the diet. For oral administration, such components may be incorporated with an excipient and used in the form of ingestible tablets, buccal tablets, troches, capsules, elixirs, suspensions, syrups, wafers, and the like. The tablets, troches, pills, capsules, and the like can also contain the following: a binder such as gum tragacanth, acacia, corn starch, or gelatin; excipients such as dicalcium phosphate; a disintegrating agent such as corn starch, potato starch, alginic acid, and the like; a lubricant such as magnesium stearate; and a sweetening agent such as sucrose, lactose, or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the active compound, sucrose as a sweetening agent, methyl and propylparabens as preservatives, a dye, and flavoring such as cherry or orange flavor. Oil-in-water emulsions may be better suited for oral use in infants or children because these are water-miscible, and thus their oiliness is masked. Such emulsions are well known in the pharmaceutical sciences.

The term "therapeutically effective amount" has been previously defined. As mentioned before, the doses mentioned herein must be considered only as guides for the person skilled in the art, who must adjust the doses depending on the desired effect, characteristics of the agents included in the combination, subject to be treated, severity of the disease suffered by the subject, chosen dosage form, etc.

Doses of active ingredients may be expressed either in mg of active ingredient per kg of body weight or in mg of active ingredient per square meter of body surface. The article from Reagan-Shaw S. "Dose translation from animal to human studies revisited". FASEB J 2007, 22:659-661 provides the standard conversion factors used to convert mg/kg to mg/m².

$$\text{Dose(mg/kg)} \times K_m = \text{Dose(mg/m}^2\text{)}$$

This conversion is the basis for converting dose in a first animal species to dose in a second animal species (allometric dose translation). Thus, animal dose (AD) in mg/kg can be converted to human equivalent dose (HED) in mg/kg using the following formula:

$$HED \text{ (mg/kg)} = AD \text{ (mg/kg)} \times \frac{\text{Animal } K_m}{\text{Human } K_m}$$

wherein the $K_m$ for each species is shown in Table 1.

TABLE 1

K_m factor for conversion of AD to HED

| Specie | | $K_m$ factor |
|---|---|---|
| Human | Adult | 37 |
|  | Child | 25 |
| Baboon | | 20 |
| Dog | | 20 |
| Monkey | | 12 |
| Rabbit | | 12 |
| Guinea pig | | 8 |
| Rat | | 6 |
| Hamster | | 5 |
| Mouse | | 3 |

In particular, the doses mentioned herein can be adapted for any mammal according to the guidelines of the FDA for conversion of doses based on body surface area (Guidance for Industry, Estimating the Maximum Safe Starting Dose in Initial Clinical Trials for Therapeutics in Adult Healthy Volunteers, U.S. Department of Health and Human Services, Food and Drug Administration, Center for Drug Evaluation and Research (CDER), July 2005, see Table 1).

In a particular embodiment of the combination, pterostilbene, pterostilbene phosphate or a pharmaceutically acceptable salt thereof is administered at a dose of 30 mg/m$^2$/48 h to 150 mg/m$^2$/48 h, preferably from 50 mg/m$^2$/48 h to 125 mg/m$^2$/48 h, preferably from 60 mg/m$^2$/48 h to 120 mg/m$^2$/48 h, more preferably from 75 mg/m$^2$/48 h to 100 mg/m$^2$/48 h, even more preferably at a dose of 90 mg/m$^2$/48 h.

In a particular embodiment of the combination for use according to the invention, pterostilbene, pterostilbene phosphate or a pharmaceutically acceptable salt thereof is administered every 48 hours. In a particular embodiment, pterostilbene, pterostilbene phosphate or a pharmaceutically acceptable salt thereof is administered for at least 1 week, at least 2 weeks, at least 3 weeks, at least 4 weeks, at least 5 weeks, at least 6 weeks, at least 7 weeks, at least 8 weeks, at least 9 weeks, at least 10 weeks or more. More preferably, is administered for five weeks.

In a particular embodiment of the combination for use according to the invention, pterostilbene, pterostilbene phosphate or a pharmaceutically acceptable salt thereof is administered every 48 hours for 3-5 weeks.

In a particular embodiment of the combination for use according to the invention, the glutathione depleting agent is administered every 48 hours for at least 1 week, at least 2 weeks, at least 3 weeks, at least 4 weeks, at least 5 weeks, at least 6 weeks, at least 7 weeks, at least 8 weeks, at least 9 weeks, at least 10 weeks or more.

In a particular embodiment of the combination for use according to the invention, the cancer chemotherapeutic agent, preferably paclitaxel, more preferably protein bound paclitaxel, is administered once a week for at least 1 week, at least 2 weeks, at least 3 weeks, at least 4 weeks, at least 5 weeks, at least 6 weeks, at least 7 weeks, at least 8 weeks, at least 9 weeks, at least 10 weeks or more. In another particular embodiment is administered once every two weeks, once every three weeks, once every four weeks, once every five weeks, preferably, once every three weeks.

In a particular embodiment, the cancer chemotherapeutic agent is administered following the guidelines established for the treatment of a particular cancer, which are known by the skilled person, usually in cycles of several days separated by periods of several weeks. The glutathione depleting agent can be administered during said periods between the cycles of administration of the cancer chemotherapeutic agent.

In a particular embodiment, when the cancer chemotherapeutic agent is paclitaxel, preferably protein bound paclitaxel, it is administered at a dose of 100 mg/m$^2$/week to 150 mg/m$^2$/week, preferably 110 mg/m$^2$/week to 140 mg/m$^2$/week, more preferably 120 mg/m$^2$/week to 130 mg/m$^2$/week. In a more particular embodiment, when the cancer chemotherapeutic agent is paclitaxel, preferably protein bound paclitaxel, it is administered at a dose of 260 mg/m$^2$/3 weeks.

Pterostilbene, pterostilbene phosphate or a pharmaceutically acceptable salt thereof, the glutathione depleting agent and the cancer chemotherapeutic agent may be administered using a 1:1:1 ratio of pterostilbene, pterostilbene phosphate (or pharmaceutically acceptable salt thereof): glutathione depleting agent:chemotherapeutic agent or different w/w ratios, ranging for example from 1-100:100-1:1, preferably from 1-50:50-1:1, more preferably from 1-20:20-1:1, even more preferably from 1-10:10-1:1; from 1:1-100:100-1, preferably from 1:1-50:50-1, more preferably from 1:1-20:20-1, even more preferably from 1:1-10:10-1; from 1-100:1:100-1, preferably from 1-50:1:50-1, more preferably from 1-20:1:20-1, even more preferably from 1-10:1:10-1. These ranges include all intermediate ratios. In a particular embodiment, the ratio pterostilbene, pterostilbene phosphate (or pharmaceutically acceptable salt thereof): cancer chemotherapeutic agent is 1-5:9-1, preferably 1-5:8,7-1,7. In another particular embodiment the ratio pterostilbene, pterostilbene phosphate (or pharmaceutically acceptable salt thereof): glutathione depleting agent:chemotherapeutic agent is 30-40:140-150:1, preferably 38:144:1.

Lastly, as used herein the chemotherapeutic agent may be replace by other known therapies for cancer such as biocides or radiotherapy.

Further Aspects of the Present Invention

1. A combination comprising (i) pterostilbene, pterostilbene phosphate or a pharmaceutically acceptable salt thereof, (ii) a glutathione depleting agent and (iii) a cancer chemotherapeutic agent.
2. The combination according to aspect 1, comprising a disodium salt of pterostilbene phosphate.
3. The combination according to any of aspects 1 or 2, wherein the glutathione depleting agent is selected from the group consisting of: a) a Bcl-2 antisense oligodeoxynucleotide; b) an inhibitor of multidrug resistance protein 1; c) an inhibitor of the gamma-glutamyl transpeptidase; d) an inhibitor of cystine uptake; e) disodium glutathione disulfide; f) phenethyl isothiocyanate; g) a glucocorticoid receptor antagonist; h) an anti-IL-6 agent; i) buthionine sulfoximine; j) diethylmaleate; k) NPD926; l) parthenolide; m) piperlongumine and n) an inhibitor of a protein from the bromodomain and extraterminal domain family.
4. The combination according to aspect 3, wherein the inhibitor of multidrug resistance protein 1 is verapamil.
5. The combination according to aspect 3, wherein the inhibitor of the gamma-glutamyl transpeptidase is acivicin.
6. The combination according to aspect 3, wherein the inhibitor of cystine uptake is sulphasalazine.
7. The combination according to aspect 3, wherein the glucocorticoid receptor antagonist is RU-486.
8. The combination according to aspect 3, wherein the anti-IL-6 agent is an inhibitory antibody against IL-6 or an inhibitor of the IL-6 receptor.

9. The combination according to aspect 8, wherein the anti-IL-6 agent is selected from the group consisting of tocilizumab, elsilimomab and siltuximab.

10. The combination according to aspect 3, wherein the inhibitor of a protein from the bromodomain and extra-terminal domain family is selected from the group consisting of JQ1, GSK525762A and OTX-015 and CPI-0610.

11. The combination according to aspect 3, wherein the glutathione depleting agent is diethylmaleate.

12. The combination according to any of aspects 1 to 11, wherein the cancer chemotherapeutic agent comprises paclitaxel.

13. The combination according to aspect 12, wherein the cancer chemotherapeutic agent comprising paclitaxel is protein-bound paclitaxel.

14. The combination according to any of aspects 1 to 13, wherein said combination does not comprise a glucocorticoid.

15. The combination according to aspect 14, wherein the glucocorticoid is corticosterone.

16. The combination according to any of aspects 1 to 15, wherein the combination comprises pterostilbene, pterostilbene phosphate or a pharmaceutically acceptable salt, a glutathione depleting agent and a cancer chemotherapeutic agent as sole therapeutic agents.

17. A combination according to any of aspects 1 to 16 for use in medicine.

18. A combination according to any of aspects 1 to 16 for use in the treatment and/or prevention of cancer, wherein the administration of pterostilbene, pterostilbene phosphate or a pharmaceutically acceptable salt thereof starts before the administration of the glutathione depleting agent and the cancer chemotherapeutic agent.

19. The combination for use according to aspect 18, wherein the cancer is melanoma.

20. The combination for use according to any of aspects 18 or 19, wherein the administration of pterostilbene, pterostilbene phosphate or a pharmaceutically acceptable salt thereof and the administration of the glutathione depleting agent and/or the cancer chemotherapeutic agent overlaps in time.

21. The combination for use according to any of aspects 18 to 20, wherein the administration of the glutathione depleting agent starts before the administration of the cancer chemotherapeutic agent.

22. The combination for use according to any of aspects 18 to 20, wherein the administration of the cancer chemotherapeutic agent starts before the administration of the glutathione depleting agent.

23. The combination for use according to any of aspects 17 to 22, wherein said combination is administered by intravenous or intraperitoneal route.

24. The combination for use according to any of aspects 17 to 23, wherein pterostilbene, pterostilbene phosphate or a pharmaceutically acceptable salt thereof is administered at a dose of 30 mg/m$^2$/48 h to 150 mg/m$^2$/48 h.

25. The combination for use according to aspect 24, wherein pterostilbene, pterostilbene phosphate or a pharmaceutically acceptable salt thereof is administered at a dose of 90 mg/m$^2$/48 h.

26. The combination for use according to aspect 25, wherein pterostilbene, pterostilbene phosphate or a pharmaceutically acceptable salt thereof is administered every 24-48 hours for 3-5 weeks.

27. The combination for use according to any of aspects 17 to 26, wherein the cancer chemotherapeutic agent is protein bound paclitaxel and is administered at a dose of 100 mg/m$^2$/week to 150 mg/m$^2$/week.

28. The combination for use according to any of aspects 17 to 26, wherein protein bound paclitaxel is administered at a dose of 260 mg/m$^2$/3 weeks.

Example

Methods

Cell Culture.

Human A2058, MeWo and MelJuso melanoma cells, and mouse AtT-20 pituitary corticotroph tumor cells were from the American Type Culture Collection (ATCC). Human HEMa-LP epidermal melanocytes were from Life Technologies (Grand Island, N.Y.). Human MDA-MB-231 (triple negative: ER−, PR−, HER2−) and MCF-7 (ER+, PR+, HER2−) breast adenocarcinoma, A549 lung adenocarcinoma (NSCLC), HepG2 hepatocellular carcinoma, LNCaP (AR+) and PC-3 (AR−) prostate adenocarcinoma, SK-OV-3 epithelial ovarian carcinoma, and HT-29 and Caco-2 colorectal carcinoma cells were from the American Type Culture Collection. Cells were grown in Dulbecco's modified Eagle's medium (DMEM) (Invitrogen, San Diego, Calif.), pH 7.4, supplemented with 10% heat-inactivated FCS (Biochrom KG, Berlin, Germany), 100 units/ml penicillin and 100 µg/ml streptomycin. Cells were plated, at a density of 20,000 cells/cm2, and cultured at 37° C. in a humidified atmosphere with 5% CO2. Cells were harvested by incubation for 5 min with 0.05% (w/v) trypsin (Sigma, St. Louis, Mo.) in PBS (10 mM sodium phosphate, 4 mM KCl, 137 mM NaCl), pH 7.4, containing 0.3 mM EDTA, followed by the addition of 10% FCS to inactivate the trypsin. Cell numbers were determined using a Coulter Counter (Coulter Electronic Inc., Miami, Fla.). Cells were allowed to attach for 12 h before any treatment addition. Cellular viability was assessed as previously reported (Mena, S. et al. Clin Cancer Res 13, 2658-2666 (2007)), by measuring trypan blue exclusion and leakage of lactate dehydrogenase activity.

Animals, Tumor Growth, and In Vivo Administration of Pter.

Female nu/nu nude mice (6-8 weeks; Charles Rivers Laboratories, Wilmington, Mass.) were fed ad libitum on a standard diet (Harlan Teklad Animal Diets & Bedding, Madison, Wis.). Mice were kept on a 12-h-light/12-h-dark cycle with the room temperature at 22° C. Procedures involving animals were in compliance with international laws and policies (EEC Directive 86/609, OJ L 358. 1, Dec. 12, 1987; and NIH Guide for the Care and Use of Laboratory Animals, NIH Publ. No. 85-23, 1985). For cancer xenograft experiments, mice were inoculated s.c. with 10×10$^6$ cancer cells per mouse. Tumor volume was calculated based on two dimensions, measured using calipers, and was expressed in mm$^3$ according to V=0.5a×b$^2$, where a and b are the long and the short diameters of the tumor, respectively. For histological analysis xenograft samples were first fixed in 4% formaldehyde, paraffin embedded, and stained as indicated below. Mice were monitored after inoculation, and tumor measurements were taken every 2 days. For pharmacokinetic and treatment studies Pterostilbene (Green Molecular S. L., Paterna, Spain) [dissolved in DMSO:ethanol (2:1), 50 mg Pter/ml] was administered i.v. through the jugular vein (where, previously, a permanent catheter was surgically fixed). Administration was slowly performed during 1-2 min.

Determination of Pter and its Metabolites by High-Pressure Liquid Chromatography and Mass Spectrometry (LC-MS/MS).

LC-MS/MS was carried out, as previously described (Ferrer, P. et al. *Neoplasia* 7, 37-47 (2005); Azzolini, M. et al. *Mol Nutr Food Res* 58, 2122-2132 (2014)) in detail, using a TSQ Vantage™ Triple Quadrupole Mass Spectrometer (Thermo Scientific, Waltham, Mass.) equipped with a Shimadzu LC-10ADvp. pump and a SLC-10Avp. controller system with a SIL-10ADvp. autoinjector.

Immunohistochemistry.

Monoclonal mouse anti-human HMB45 antibodies (Abcam, Cambridge, UK) were used for immunohistochemical detection of melanoma cells. For that purpose, the tumors were fixed and paraffin embedded as described above. Immunohistochemical analysis was applied to tissue slices (5 µm thick) following the standard methodology recommended by Abcam. A horseradish peroxidase-conjugated goat anti-mouse polyclonal (Abcam) was used as secondary antibody.

Monoclonal mouse anti-human Ki-67 (Dako, Sant Cugat del Vallés, Spain) were used for immunohistochemical detection of the tumor growing fraction. Immunohistochemical analysis was applied to tissue slices (5 µm thick) following the standard methodology recommended by Dako. A biotin-conjugated goat anti-rabbit polyclonal (Dako) was used as secondary antibody.

DNA strand breaks in apoptotic cells were assayed by using a direct TUNEL labeling assay (Boehringer, Mannheim, Germany) and fluorescence microscopy following manufacturer's methodology.

CRH Expression in the Brain (In Situ Hybridization).

Sections of 10 µm of the PVN were cut according to a mouse brain atlas (Allen Institute for brain science, http://www.brain-map.org) on a cryostat, mounted on polysine microscope slides (Menzel-Glazer, Braunschweig, Germany), and stored at −80° C. for 24 h. Then sections were fixed in 4% paraformaldehyde, further permeabilized by proteinase K treatment, acetylated twice with 0.25% acetic anhydride in 0.1 M triethanolamine, and dehydrated in a graded ethanol series. Hybridization, carried out as described before (Lachize, S. et al. *Proc Natl Acad Sci USA* 106, 8038-8042 (2009)), was performed using specific 48-mer, $^{35}$S-labeled oligonucleotide probes for murine CRH mRNA (5'-GGC CCG CGG CGC TCC AGA GAC GGA TCC CCT GCT CAG CAG GGC CCT GCA-3') (SEQ ID NO: 1). Hybridized slices were exposed to BioMax MR film (Kodak, Rochester, N.Y.). The mRNA expression of CRH in the PVN was quantified as gray density minus background in digitized images using the NIH ImageJ 1.6 program (http://rsb.info.nih.gov/ij). Bilateral measures were taken from two to four PVN sections for each mouse, which were pooled to provide individual means per mouse. For tissue background, the optical density of a nonhybridized region outside the PVN was measured.

Measurement of ACTH, Corticosterone, and NORA Levels.

Plasma levels of ACTH (Calbiotech, Inc., Spring Valley, Calif.), corticosterone (Kamiyama Biomedical Co., Seattle, Wash.), and NORA (IBL, Hamburg, Germany) were quantified by ELISA according to the instructions of the suppliers.

Measurement of the GR Content of Cancer Cell Lines by [$^3$H]-Labeled Ligand Binding Assay.

The GR content was measured by a whole-cell binding assay as previously described with some modifications (Harmon, J. M. & Thompson, E. B. *Mol Cell Biol* 1, 512-521 (1981)). Briefly 72 h-cultured melanoma cells were harvested, as indicated above, and resuspended in culture medium to a density of 5×10$^6$ cells/mL. Then cells were exposed to various concentrations of [$^3$H]-dexamethasone (GE Healthcare Life Sciences, Buckinghamshire, UK) from 1 to 100 nmol/L in the presence or absence of 10 µmol/L unlabeled dexamethasone, followed by incubation for 1 h at 37° C., and harvested by centrifugation at 1,200 r/min×1 min. Cells were then washed thrice in 5.0 mL of Hank's balanced salt solution and finally suspended in 1.5 mL of the same solution. A 0.2-mL aliquot of this suspension was used for the determination of cell number, and 1.0 mL was assayed for radioactivity by a liquid scintillation counter. The presence of at least 200-fold excess of unlabeled dexamethasone effectively competed out all of the binding of [$^3$H]-dexamethasone to specific GR. The binding of [$^3$H]-dexamethasone to specific GR was represented as the difference in disintegrations per minute per cell between those samples incubated with [$^3$H]-dexamethasone alone and those with at least 200-fold excess of unlabeled dexamethasone. Using the specific activity of [$^3$H]-dexamethasone, the number of receptors per cell was calculated, assuming that each receptor binds to one dexamethasone molecule.

Transfection of the Red Fluorescence Protein.

First the pDsRed-2 vector (Clontech Laboratories Inc., Palo Alto, Calif.) was used, as previously described for A375 melanoma cells (Mena, S. et al. *J Transl Med* 10, 8 (2012)), to engineer A2058, MeWo and MelJuso melanoma clones stably expressing the RFP. Isolation of A2058-RFP, MeWo-RFP or MelJuso-RFP cells from the growing xenografts was performed by laser microdissection and high-performance cell sorting as previously described in detail (Mena, S. et al. *J Transl Med* 10, 8 (2012)).

RT-PCR and Detection of mRNA.

Total RNA was isolated using the TRIzol kit from Invitrogen following the manufacturer's instructions. cDNA was obtained using a random hexamer primer and a MultiScribe Reverse Transcriptase kit as recommended by the manufacturer (TaqMan RT Reagents, Applied Biosystems, Foster City, Calif.). PCR master mix and AmpliTaq Gold DNA polymerase (Applied Biosystems) were added to the specific primers previously reported (Dobos, J. et al., *Pathol Oncol Res* 17, 729-734 (2011).) for the GCLC (catalytic subunit), GSH synthase (GSS), GPX2, GSR, GGT, SOD1, SOD2, CAT, NOX1 and glyceraldehyde-3P-dehydrogenase (GAPDH) (Sigma-Genosys). Other primer sequences (5' to 3') used were: GSH transferase A1 (GSTA1), sense TTCCTTACTGGTCCTCACATCTC (SEQ ID NO: 2) and antisense TCACCGGATCATGGCCAGCA (SEQ ID NO: 3); thioredoxin reductase 1 (TXNRD1), sense GTGTTGTGGGCTTTCACGTA (SEQ ID NO: 4) and antisense CAGCCTGGAGGATGCTTG (SEQ ID NO: 5); malic enzyme 1 (ME1), sense AGTGCCTACCTGTGATGTTG (SEQ ID NO: 6) and antisense GGCTTGACCTCTGATTCTCT (SEQ ID NO: 7); isocitrate dehydrogenase 1 (IDH1), sense ACCAAATGGCACCATACGA (SEQ ID NO: 8) and antisense TTCATACCTTGCTTAATGGGTGT (SEQ ID NO: 9) (Sigma-Genosys). The primer sequences (5' to 3') used for POMC were: sense AGTGTCGTCAGAAAGAACGAACGGC (SEQ ID NO: 10) and antisense CTCAACTGGTGTCGTGGAGTC (SEQ ID NO: 11). Real-time quantification of mRNA relative to GAPDH was performed with a SYBR Green I assay and an iCycler detection system (Biorad, Hercules, Calif.). Target cDNA was amplified using the following conditions: 10 min at 95° C. followed by 40 cycles of denaturation at 95° C. for 30 sec and annealing and extension at 60° C. for 1 min. Changes in fluorescence were measured in real time during the extension step. The threshold cycle (CT) was determined and the relative gene expression expressed as fold change=$2^{-\Delta(\Delta C_T)}$, where $\Delta C_T = C_T\text{target} - C_T\text{GAPDH}$, and $\Delta(\Delta C_T) = \Delta C_T\text{treated} - \Delta C_T\text{control}$.

Enzyme Assays.

To measure enzyme activity, isolated tumor cells were homogenized in 0.1 M phosphate buffer (pH 7.2) at 4° C. GCL and GSS activities were measured as described previously (Obrador, E. et al. *Hepatology* 35, 74-81 (2002)). GPX (selenium dependent) activity was measured as described by Flohé and Gunzler (Flohe, L. & Gunzler, W. A. *Methods Enzymol* 105, 114-121 (1984)) using $H_2O_2$ as a substrate. GSR activity was determined as described by Akerboom and Sies (Akerboom, T. P. et al, *Bull Eur Physiopathol Respir* 17 Suppl, 221-227 (1981)). GGT activity was measured as described previously (Obrador, E. et al. *Hepatology* 35, 74-81 (2002)). GST activity was measured using an assay kit from Sigma. TXNRD activity, defined by the concentration of sodium-lipoate (disulfide) reduced to dehydrolipoate (dithiol) per milligram protein, was measured as previously described (Javvadi, P. et al. *Cancer Res* 70, 1941-1950 (2010)). SOD activity was measured as described by Flohé and Otting (Flohe, L. & Otting, F. *Methods Enzymol* 105, 93-104 (1984).) using 2 mM cyanide in the assay medium to distinguish mangano-type enzyme (SOD2) from the cuprozinc type (SOD1). CAT activity was analyzed as described by Aebi (Aebi, H. *Methods Enzymol* 105, 121-126 (1984)). NOX activity was measured by chemiluminescence following the methodology of Wind et al. (Wind, S. et al. Comparative pharmacology of chemically distinct NADPH oxidase inhibitors. *Br J Pharmacol* 161, 885-898 (2010)). Protein concentration was determined with the Pierce BCA protein assay (Fisher Scientific, Waltham, Mass.).

Measurement of $H_2O_2$ and $O_2^{\cdot-}$.

Quantitative measurement of $H_2O_2$ and flow cytometry determination of $O_2^{\cdot-}$ generation were performed as previously described (Benlloch, M. et al. *J Biol Chem* 281, 69-79 (2006)).

GSH, GSSG, $NADP^+$ and NADPH Determination.

GSH and GSSG were determined, following procedures previously described (Obrador, E. et al. *PLoS One* 9, e96466 (2014)), by LC/MS using the same equipment described above for pterostilbene determination. Cell processing was performed according to published methodology, where rapid N-ethylmaleimide derivatization was used to prevent GSH auto-oxidation (Asensi, M. et al. *Anal Biochem* 217, 323-328 (1994)). $NADP^+$ and NADPH were quantitated using an assay kit from Sigma (St. Louis, Mo.).

Nrf2 Gene Transfer and Measurement.

The Tet-Off Advanced Inducible Gene Expression System (Clontech, Palo Alto, Calif.) was used to insert the human Nrf2 gene and for transfection into melanoma cells following manufacturer's instructions. Tet-off cells stably expressed Tet-regulated pTRE-Tight-Nrf2 giving up to an increased Nrf2 gene expression (Tet-Nrf2 cells). To suppress Nrf2 protein levels Tet-Nrf2 cells were cultured in the presence of 2 mg tetracycline (Sigma)/$10^6$ cells. The NE-PER extraction kit from Thermo Scientific (Rockford, Ill.) was used for nuclear protein extraction according to the manufacturer's instructions. The protein content was determined by the Pierce BCA protein assay. The antibodies (mouse monoclonal primary antibodies) against Nrf2 were purchased from Abcam. A total of 50 mg of protein was boiled in Laemmli buffer and resolved by 12.0% SDS-PAGE. Proteins were transferred to a nitrocellulose membrane (Hybond C-extra, GE Healthcare Europe GmbH, Barcelona, Spain) and subjected to Western blotting. The blotted membrane was blocked for 1 h at room temperature in Tris-buffered saline (TBS) containing 5% (w/v) membrane-blocking reagent (non-fat dried milk). All antibody incubations were carried out at room temperature in TBS containing 1% membrane-blocking reagent. The incubation steps were followed by three washing steps of 5 min using TBS containing 0.1% Tween 20. The blots were developed using horseradish peroxidase-conjugated secondary antibody and enhanced chemiluminescence (ECL system, GE Healthcare). Protein bands were quantified using laser densitometry. Equal protein loading on membranes and complete transfer was confirmed by staining the gels and membranes with Coomassie Blue. To make the pooling of data from different immunoblots possible, the relative density of each band was normalized against the internal standard analyzed on each blot.

Pomc Analysis.

RT-PCR and detection of mRNA was performed as described above. For Western blotting (see also above) POMC mouse monoclonal antibody (clone 2B2) from Origen (Rockville, Md.) were used.

Antisense Oligodeoxynucleotides.

Fully phosphorothioate-modified chimeric 20-mer human sod1 antisense oligonucleotides composed of five 2'-O-(2-methoxy)ethyl modifications on both the 5' and 3' ends and 10 oligodeoxynucleotides in the center to support RNase H activity (McKay, R. A. et al. *J Biol Chem* 274, 1715-1722 (1999)) (sequence: 5'-GTCGCCCTTCAGCACGCACA-3') (SEQ ID NO: 12) were obtained from Sigma-Genosys. As a control, an equivalent but reversed phosphorthioated 20-mer sequence was purchased from the same source. Inhibition of SOD1 expression was verified by measuring the SOD1 activity and Western blot analysis with anti-human SOD2 monoclonal antibody (Sigma).

Isolation of Tumor Cells from Mouse Xenografts Using Enzymatic Digestion and a double Ficoll gradient.

To maximize the amount of isolated cells, avoiding the use of RFP-transfected cells and subsequent laser microdissection, an alternative methodology was set up. To maximize cell yield and viability the following combination of enzymes was used: collagenase III (200 U/ml; Sigma-Aldrich), DNase I (200 U/ml; Sigma-Aldrich) and trypsin (5 mg/ml; Invitrogen), and a non-enzymatic dissociation buffer (NEDB, Invitrogen). Briefly, mice were killed, and tumors were removed (avoiding skin, muscle and fat) into cold culture media and processed immediately. The tumors were minced into 1-3 mm fragments, which were then incubated with the dissociation solution (see above) for 30 min at 37° C. The tumor fragments were mixed up and down every 10 min using a 1000 ml micropipette with a tip cut to a diameter adapted to tissue fragment size. After each incubation period, the fragments were filtered through a 40 mm nylon mesh cell strainer (BD Biosciences, San Diego, Calif., USA). The released cells were centrifuged at 1200 r.p.m. for 2 min and stored in cold CO2-independent medium with 30% FCS at 41 C. Fresh dissociation solution was added to the remaining tissue fragments for 30 min. Dissociation was stopped when no additional cells were released. The fragments were pushed through a sieve and all cells from all incubation periods were pooled and counted.

The dissociated cells were layered onto a double Ficoll gradient (Histopaque; Sigma-Aldrich; densities 1.077 and 1.119) and spun at 700 g for 30 min at room temperature. Cells removed from both interfaces were pooled and washed two times in CO2-independent medium and stored at 4° C.

Debris and red blood cell elimination was improved with the dual-density gradient. Overnight storage did not significantly alter cell viability. In vitro growing rates of all the different cancer cells used, isolated from xenografts by this methodology and as compared to the laser microdissection technique, were similar.

Piperlongumine (PL) Levels Determination by LC/MS-MS.

PL was analyzed by liquid chromatography/mass spectrometry. The LC/MS-MS system consisted of TSQ Vantage™ Triple Quadrupole Mass Spectrometer (Thermo Scientific) equipped with a Shimadzu LC-10ADvp. Pump and an SLC-10Avp. controller system with an SIL-10ADvp. autoinjector Chromatographic separation was carried out using Agilent Bio SCX NP1 (with 1.7 µm particle size; 50×4.6 mm) column at a temperature of 40° C. The elution of the drug and internal standard (piperlonguminine) was carried out by a gradient method using solvents (A) water (0.01% formic acid) and (B) acetonitrile (0.01% formic acid) with a flow rate of 0.25 mL/min. Elusion started with 20% solvent B, which was increased to 60% over a period of 3.0 mins. At 3.1 minutes, mobile phase was switched to 90% solvent B which was kept constant till 5 minutes after which it was returned to initial mobile phase. The total elution time was 5 minutes and the total run time was 9 minutes. However, mass spectrometer data was recorded from 1-4 minutes. For every run, 1 µL of sample was injected into the column. The analytes were detected by multiple reaction-monitoring (MRM) using a positive ion mode. The ion transition of PL used for analysis was parent ion m/z 318.0 to daughter ion m/z 221.3 and 190.3 and that for internal standard was parent ion m/z 274 to daughter ion m/z 201. The analytes were extracted from plasma by liquid-liquid extraction using 4 volumes of ethyl acetate followed by protein precipitation using 4 volumes of ice cold methanol. The samples were centrifuged at 15,000 g for 15 mins after which the supernatant was dried using an Eppendorf Vacufuge Plus at 35° C. and reconstituted in 100 µL, of 1:1 ratio of water and acetonitrile. The standards were prepared by spiking PL ranging from a final concentration of 0.05 µM to 50 µM. The concentration of internal standard used was 10 µM and was kept constant.

Expression of Results and Statistical Analysis.

Data are presented as the means±S.D. for the indicated number of different experiments. Statistical analyses were performed using Student's t test, and p<0.05 was considered significant.

Results

Effect of Pterostilbene on Melanoma Growth.

Three different human melanoma cell lines (see Table 2 for their genetic background) were used to investigate the effect of Pter. As shown in FIG. 1A, i.v. administration of 30 mg Pter/kg (every 48 h) caused a significant inhibition of tumor growth (approx. 70% in A2058 on day 35, 65% in Mewo on day 42, and 49% in MelJuso melanoma-bearing mice on day 42) as compared to controls. It is noteworthy to indicate that the rate of control growth also differs among the models (see FIG. 1A). At a lower dose (20 mg/kg) pterostilbene was less effective, whereas a higher dose (40 mg/kg) caused no further inhibition (FIG. 1A).

TABLE 2

Genetic background of the human melanoma cell lines used in this study

| | Melanoma cell line | | |
|---|---|---|---|
| | A2058 | MeWo | MelJuso |
| BRAF (V600E) | mutant | w | w |
| NRAS (exon 3) | w | w | Q61L |
| TP53 | V274F | Q317 | w |
| Apaf-1 | +/− | − | + |
| PTEN | +/− | +/− | +/− |
| Casp8 | + | − | + |
| Bcl-2 | +/− | + | +/− |
| Bcl-xL | − | − | − |
| Mcl-1 | + | +/− | + |

BRAF and NRAS mutational status was determined by direct sequencing of PCR-amplified genomic fragments of exons 15 and 3, respectively. p53 mutational status was determined by direct sequencing of exons 2-10 by RT-PCR. w, wild-type. Apaf-1, PTEN, Casp-8, Bcl-2, Bcl-xL, and Mcl-1 levels were determined by immunoblotting and normalized to control melanocytes. (−, +/− and + indicates a decrease, no variation or an increase, respectively, as compared to human melanocytes).

In order to correlate tumor growth inhibition and bioavailable pterostilbene concentrations, pterostilbene levels in plasma and in the tumor were investigated. As shown in FIG. 1B, after i.v. administration of 30 mg Pter/kg, its highest concentration in plasma (112±17, 116±23 and 98±13 µM in A2058, MeWo and MelJuso melanoma-bearing mice, respectively, 5 min after administration) decreased rapidly to reach the lowest concentration (approx. 1 µM) at 240-480 min. After that last time point pterostilbene levels in plasma were undetectable (not shown). Pterostilbene levels in tumors were measured in parallel and also reached the highest concentration (28±7, 33±7 and 25±7 µM in A2058, MeWo and MelJuso melanoma-bearing mice, respectively) 5 min after administration; whereas the lowest concentration (approx. 1 µM) was measured at 180 min. From the data in FIG. 1b a half-life of pterostilbene in circulating plasma of melanoma-bearing mice of 70-73 min was calculated (not significantly different from that calculated in non-tumor bearing mice where the same dose of pterostilbene was administered i.v., not shown), and of 36-40 min in the melanoma tumors.

Figure 6:
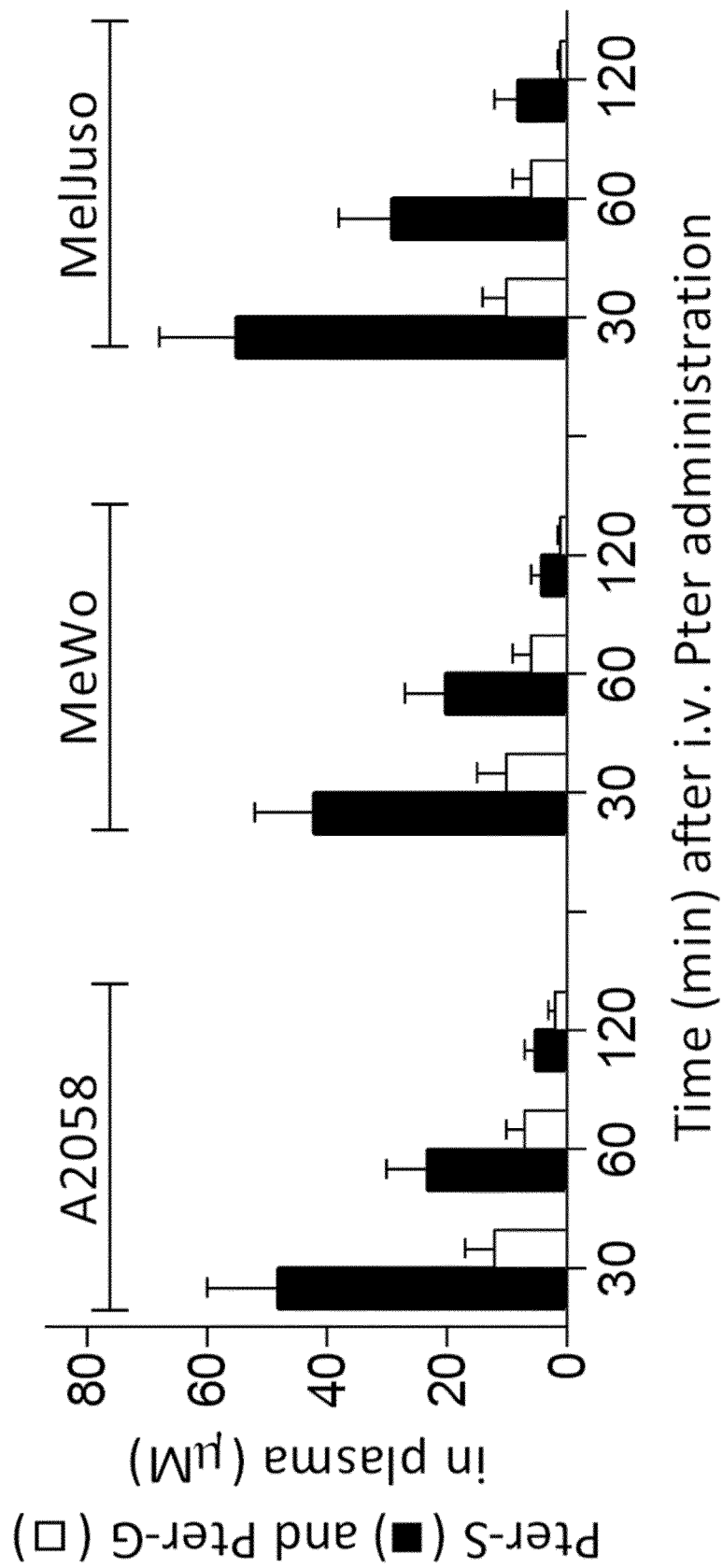
FIG. 6. Plasma levels of pterostilbene metabolites. Main Pter-derived metabolites were measured by high-pressure liquid chromatography and mass spectrometry (LC-MS/MS), after i.v. administration of 30 mg Pter/kg. LC-MS/MS was carried out, as previously described[9,10], using a TSQ Vantage™ Triple Quadrupole Mass Spectrometer (Thermo Scientific, Waltham, Mass.) equipped with a Shimadzu LC-10ADvp. pump and a SLC-10Avp. controller system with a SIL-10ADvp. autoinjector. Pterostilbene-4'-sulfate was chemically synthesized (as described by Azzolini et al.)[10] and used as an analytical standard. Pterostilbene 4'-O-D-glucuronide was synthesized as follows: molecular sieves (55 mg) and silver carbonate (138 mg, 0.5 mmol) were added to a solution of methyl (tri-O-acetyl-a-D-glucopyranosyl bromide)-uronate (198 mg, 0.5 mmol) and pterostilbene (64 mg, 0.5 mmol). The suspension was stirred at 4° C. for 12 h, then at 45° C. for 6 h. The resulting suspension, containing the glycosylated derivative and unreacted Pter, was filtered through a celite pad and washed with tetrahydrofuran (2×5 mL). The filtrate was evaporated and the residue was dissolved in dry methanol (5 mL), and then sodium methoxide was added to catalyze the de-O-acetylation. The mixture was stirred at 20° C. for 4 h and then condensed to 1 mL. To the solution was added 1 N NaOH (2 mL) and the resulting mixture was stirred at 20° C. for 2 h to hydrolyze the methyl ester. The solution was adjusted to pH 3.0 by adding Dowex® 50WX8 hydrogen form (Sigma-Aldrich) and, after filtration and evaporation, the residue was subjected to preparative HPLC to render pterostilbene 4'-O-D-glucuronide (used as an analytical standard). All data are mean values±SD of 7-8 different animals per melanoma cell line.

Measurement of the main pterostilbene metabolites in plasma (FIG. 6) confirmed previous observations, which showed that pterostilbene-4'-sulfate (Pter-S) is the main Pter-derived metabolite generated under in vivo conditions.

Based on the pterostilbene levels measured in the tumors (FIG. 1B), the next step forward was to assay the effect of this stilbene on melanoma cell proliferation and viability under controlled in vitro conditions. To mimic in vivo conditions after i.v. administration, melanoma cells were incubated in the presence of pterostilbene (15 µM) for a limited period (60 min) (this represents an approximate mean value of the concentrations of pterostilbene measured within the tumor during the first hour after i.v. administration of 30 mg Pter/kg) (FIG. 1C). Pterostilbene was added to the incubation medium each 24 hours and, as indicated, was present only for 60 min. After addition to the culture medium pterostilbene levels remained unchanged during the incubation time (data not shown), which suggests that human melanoma cells do not metabolize Pter. As shown in FIG. 1C nor tumor cell proliferation neither viability were significantly affected by pterostilbene [similar results were obtained in the presence of Pter-S and Pter-glucuronide (Pter-G), see Table 3]. However histopathological studies of tumors, obtained from melanoma-bearing mice treated with pterostilbene (as in FIG. 1B), revealed that pterostilbene administration causes a decrease in melanoma cell proliferation (Ki-67 staining) and an increase in apoptotic cell death (TUNEL) (FIG. 1D). Therefore it appears obvious that Pter-induced inhibition of melanoma growth, under in vivo conditions, must involve other factor(s) and is not the consequence of a direct anti-tumor effect elicited by pterostilbene at the levels measured within the tumors.

TABLE 3

Effect of pterostilbene metabolites on melanoma cell growth and viability in vitro

| | Melanoma cell number (×10$^6$) | | | | | |
|---|---|---|---|---|---|---|
| | A2058 | | MeWo | | MelJuso | |
| Culture time (h) | — | +Pter metabolites | — | +Pter metabolites | — | +Pter metabolites |
| 48 | 0.65 ± 0.21 | 0.59 ± 0.17 | 0.57 ± 0.25 | 0.66 ± 0.18 | 145 ± 0.36 | 1.33 ± 0.27 |
| 72 | 1.37 ± 0.39 | 1.46 ± 0.44 | 1.03 ± 0.33 | 0.95 ± 0.24 | 3.46 ± 0.86 | 3.69 ± 0.75 |

Melanoma cells were cultured as in FIG. 1. To mimic in vivo conditions Pter-S and Pter-G (synthesized as described under Methods) were incubated together at 23 and 7 µM, respectively (approx. mean values measured in plasma of Pter-treated mice, see FIG. 6, for 120 min every 24 h starting 24 h after seeding. Tumor cell viability was in all cell types and conditions >95%. Data are mean values ± SD of 5-6 different experiments.

Based on this idea, hypothetically, pterostilbene could promote microenvironment (tissue specific?)-related and/or systemic anti-tumor mechanisms. Regarding the second option it has been reported that chronic curcumin administration (5 or 10 mg/kg, p.o.) reverses some effects linked to chronic stress such as an abnormal adrenal gland weight to body weight ratio and increased thickness of the adrenal cortex, as well as elevated serum corticosterone levels and reduced glucocorticoid receptor (GR) mRNA expression. Another report showed that (−)-epigallocatechin gallate can attenuate acute stress responses through GABAergic system in the brain. Moreover dietary quercetin attenuates the hypothalamic-pituitary-adrenal (HPA) axis activation by the suppression of the corticotropin-releasing hormone (CRH) mRNA expression. These primary observations are examples of particular interest since stress has been suggested as a promoter of tumor growth and angiogenesis in different in vivo models. Thus we decided to explore first possible links between pterostilbene administration and the HPA-dependent stress response in melanoma-bearing mice.

Effect of Pterostilbene on Stress Hormones in Melanoma-Bearing Mice.

Figure 2:
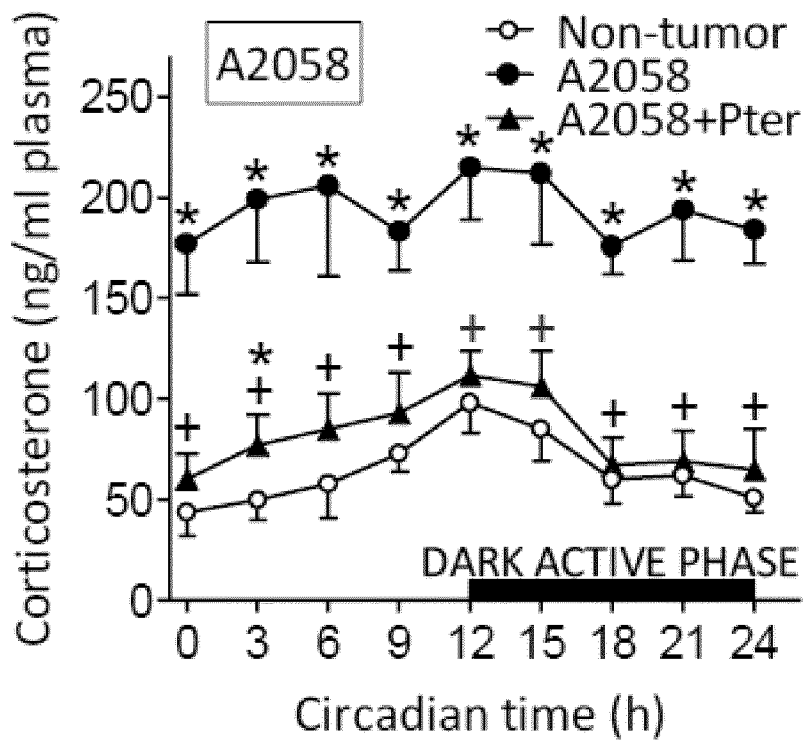
FIG. 2. Effect of pterostilbene treatment on corticosterone, ACTH and NORA levels, and CRH expression in melanoma-bearing mice. Corticosterone (A), ACTH (B), and NORA (D) levels in circulating plasma, and CRH expression (C) in the hypothalamic PVN (optical density arbitrary units, a.u.) were measured as indicated under Methods. Blood was collected from the tail vein during a 24-h period (tumors were allowed to grow for 35 days; see FIG. 1). All groups were treated as in FIG. 1. Data are mean values±SD of 7-8 different animals. *Significantly different $p<0.01$ comparing melanoma-bearing mice (untreated or treated with Pter) vs non-tumor-bearing mice; +Significantly different $p<0.01$ comparing both melanoma-bearing mice groups. Data obtained in melanoma-bearing mice treated with vehicle were not significantly different from those calculated for the untreated group (not shown).
Figure 2:
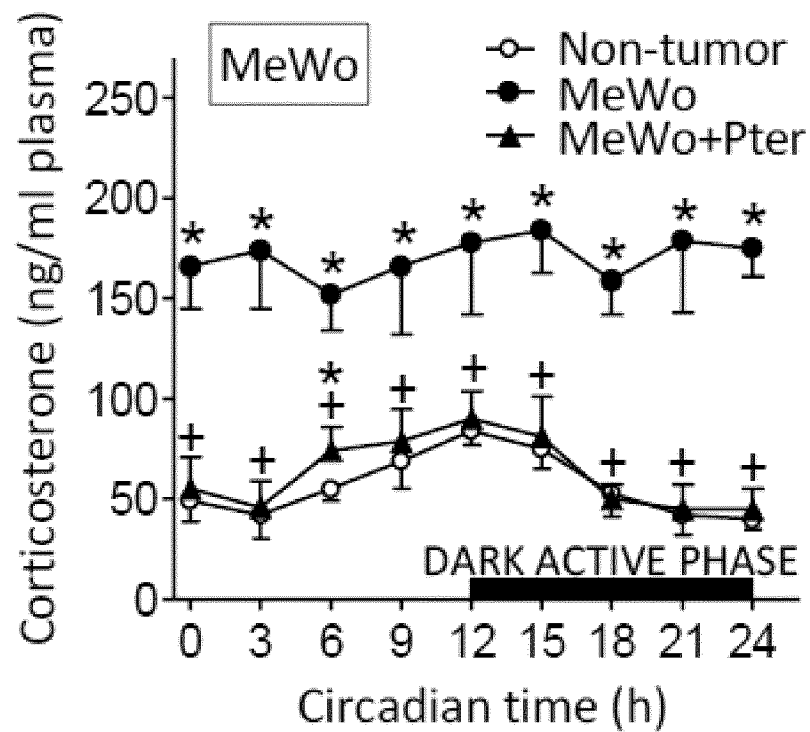
Figure 2:
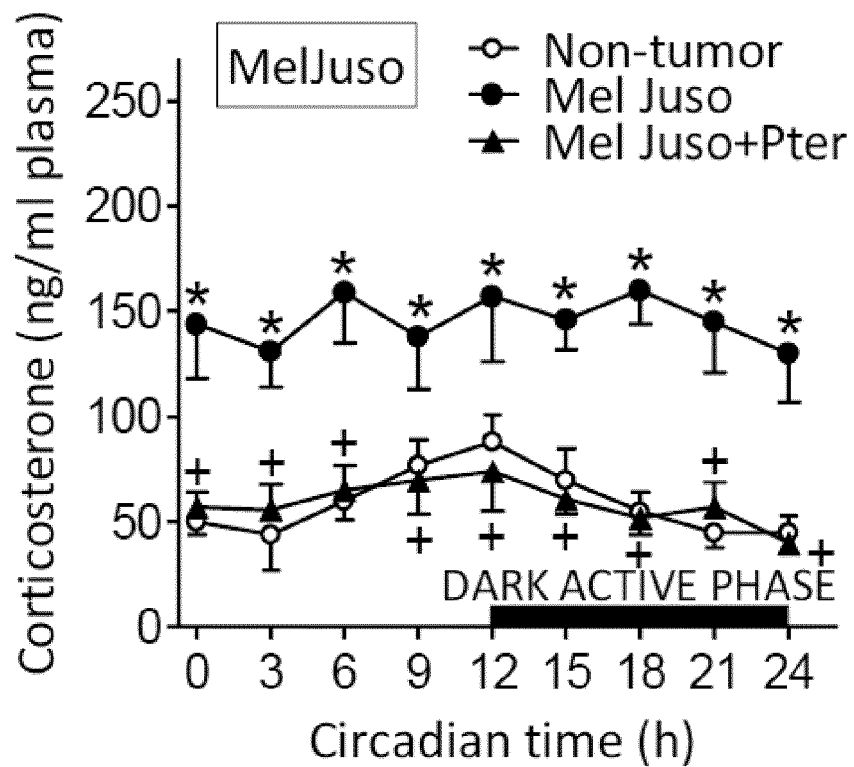
Figure 2:
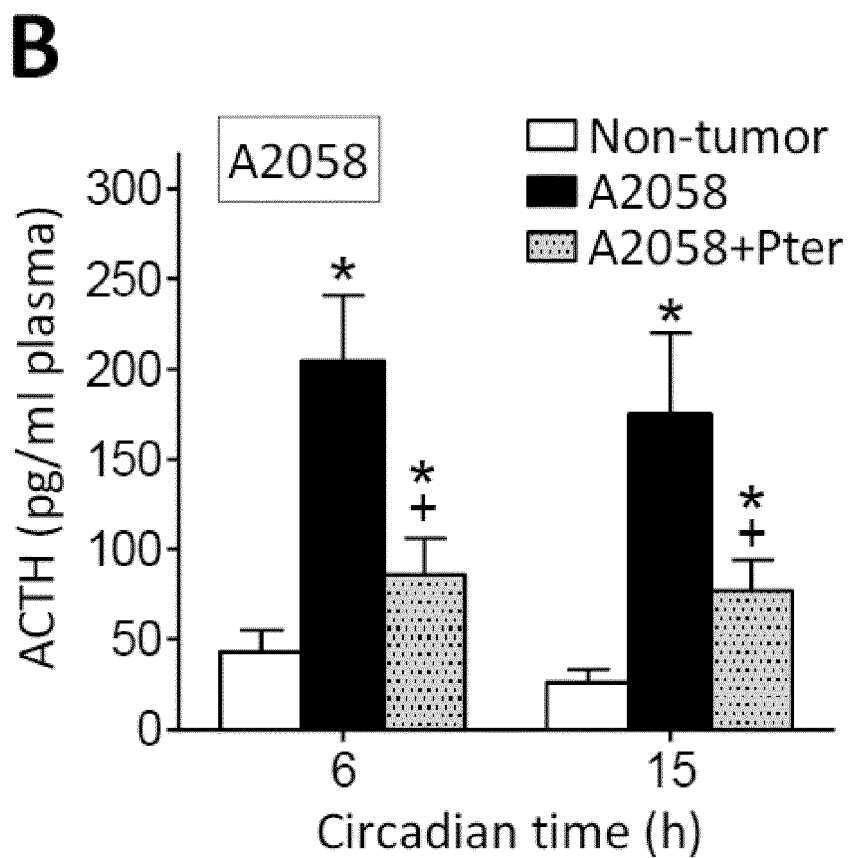
Figure 2:
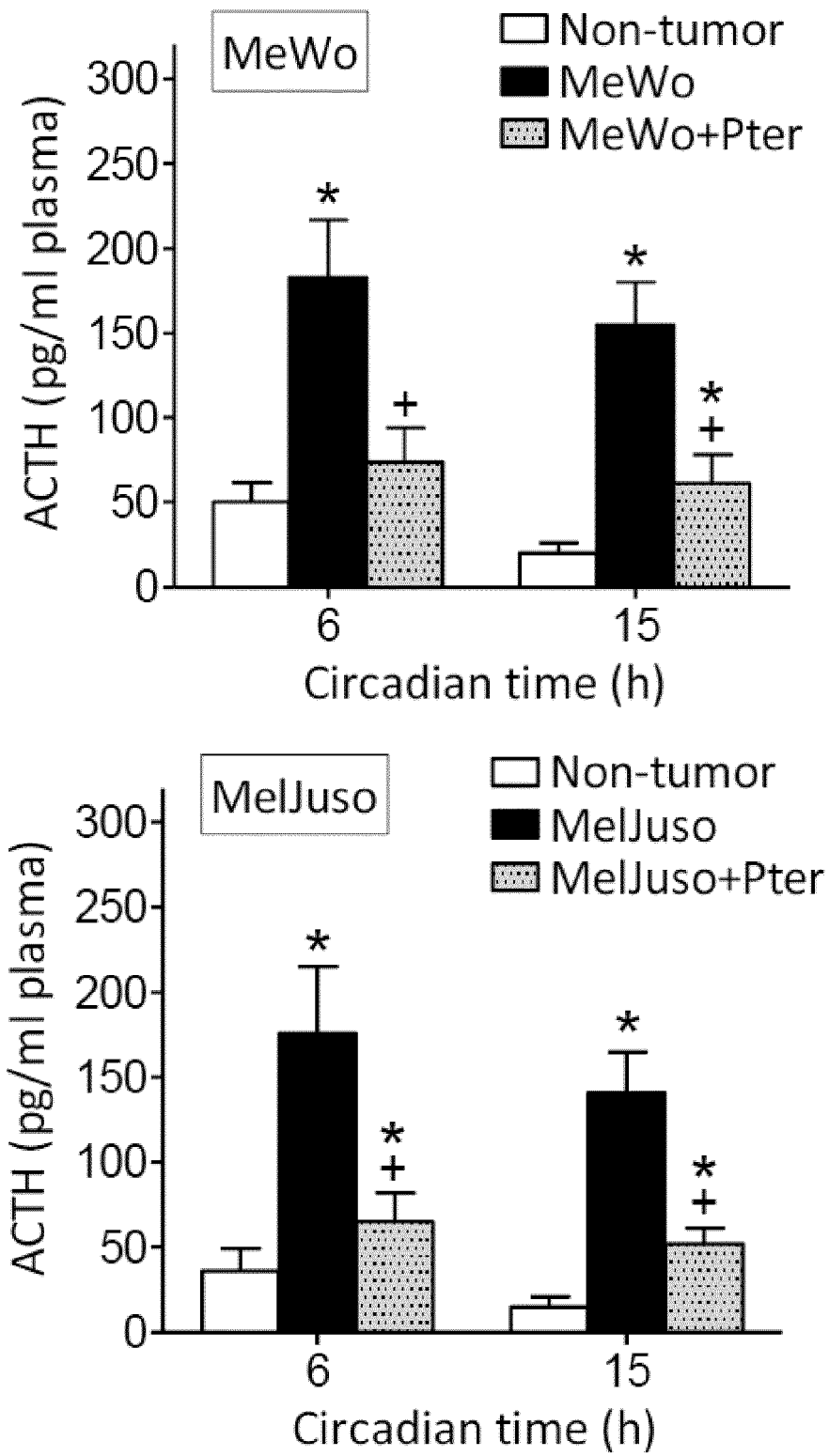
Figure 2:
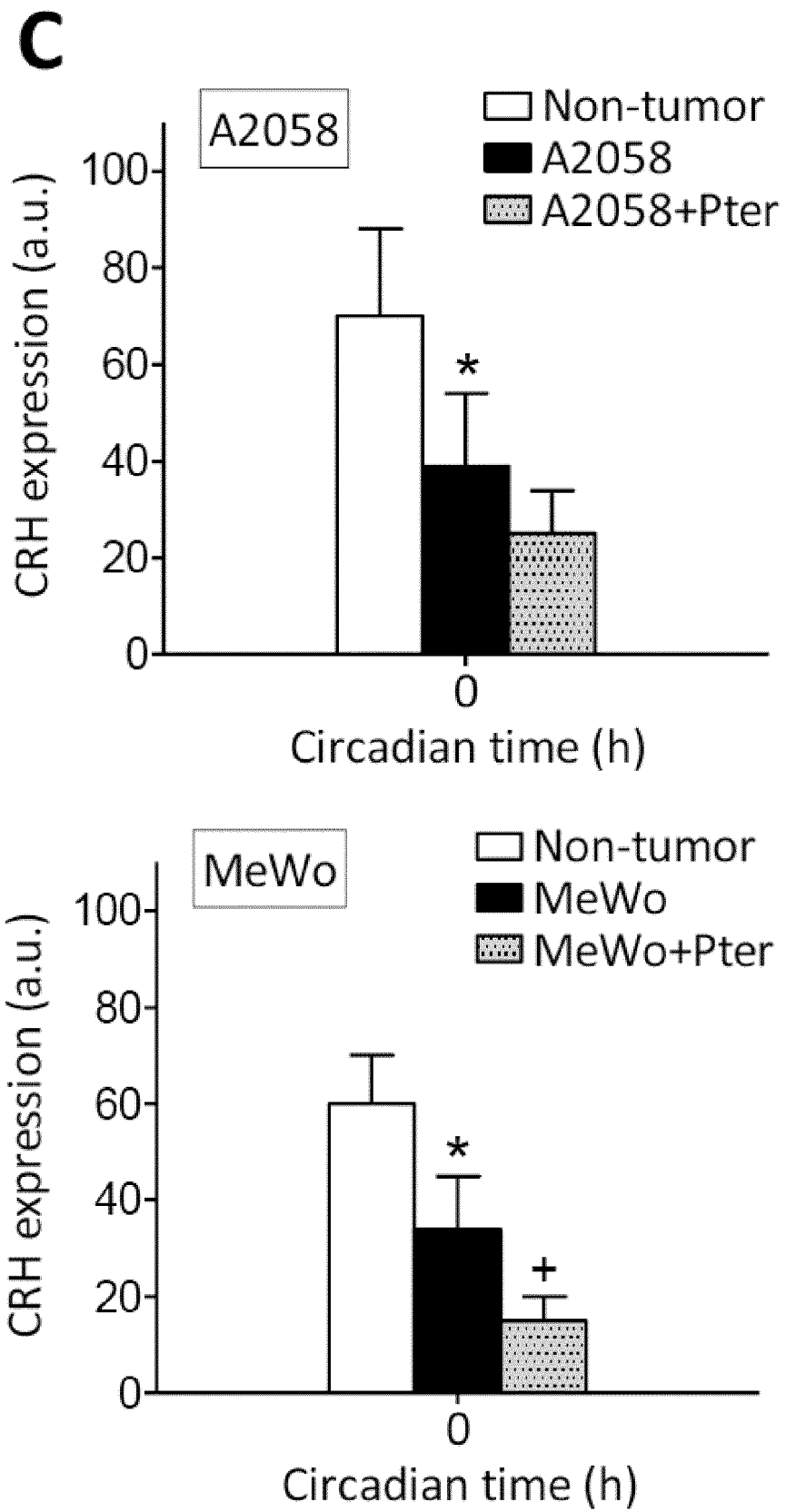
Figure 2:
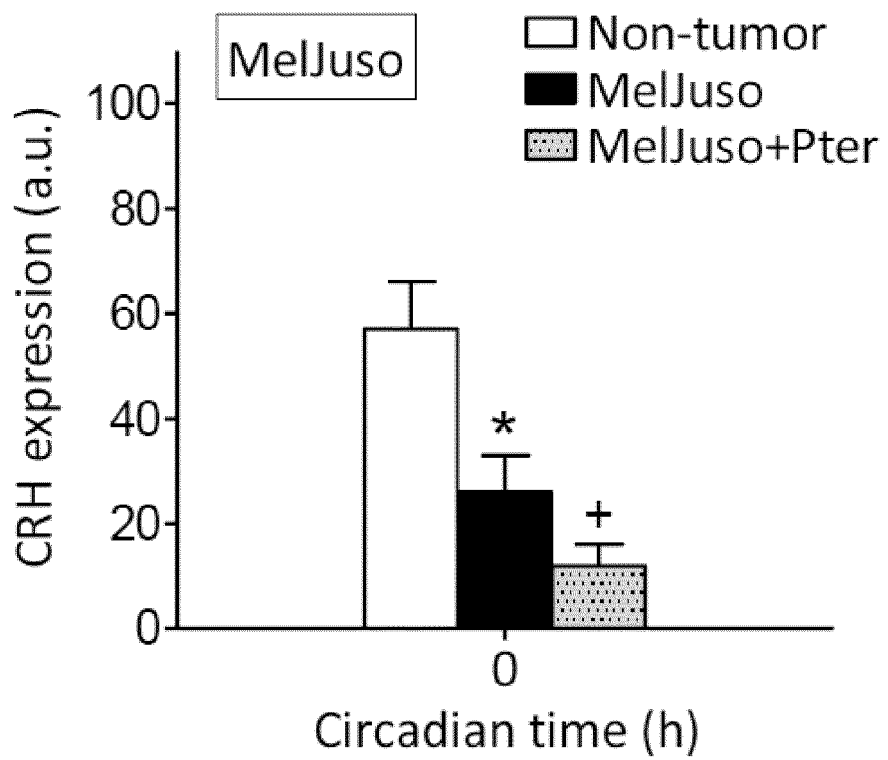
Figure 2:
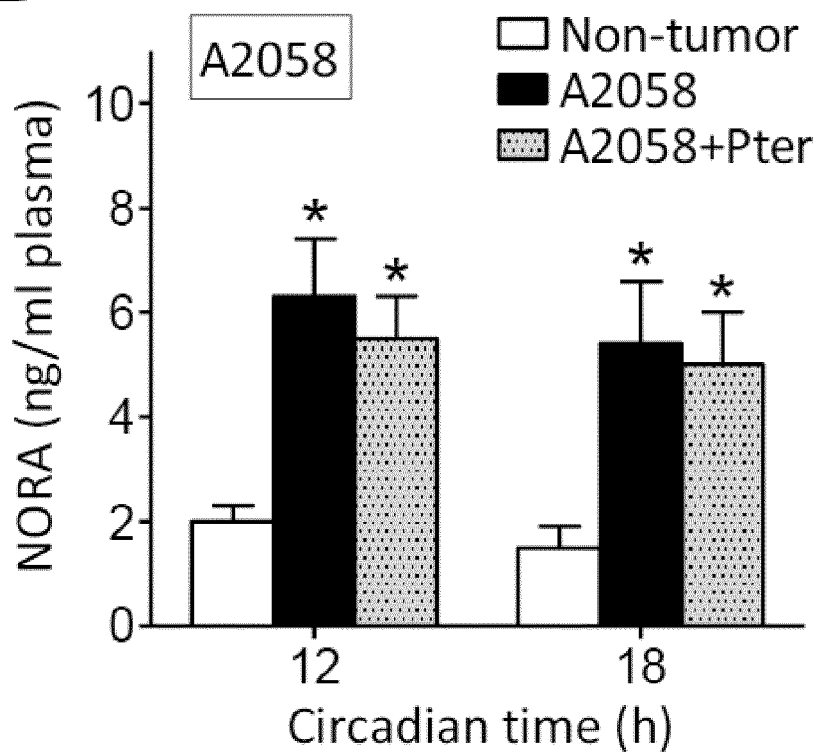
Figure 2:
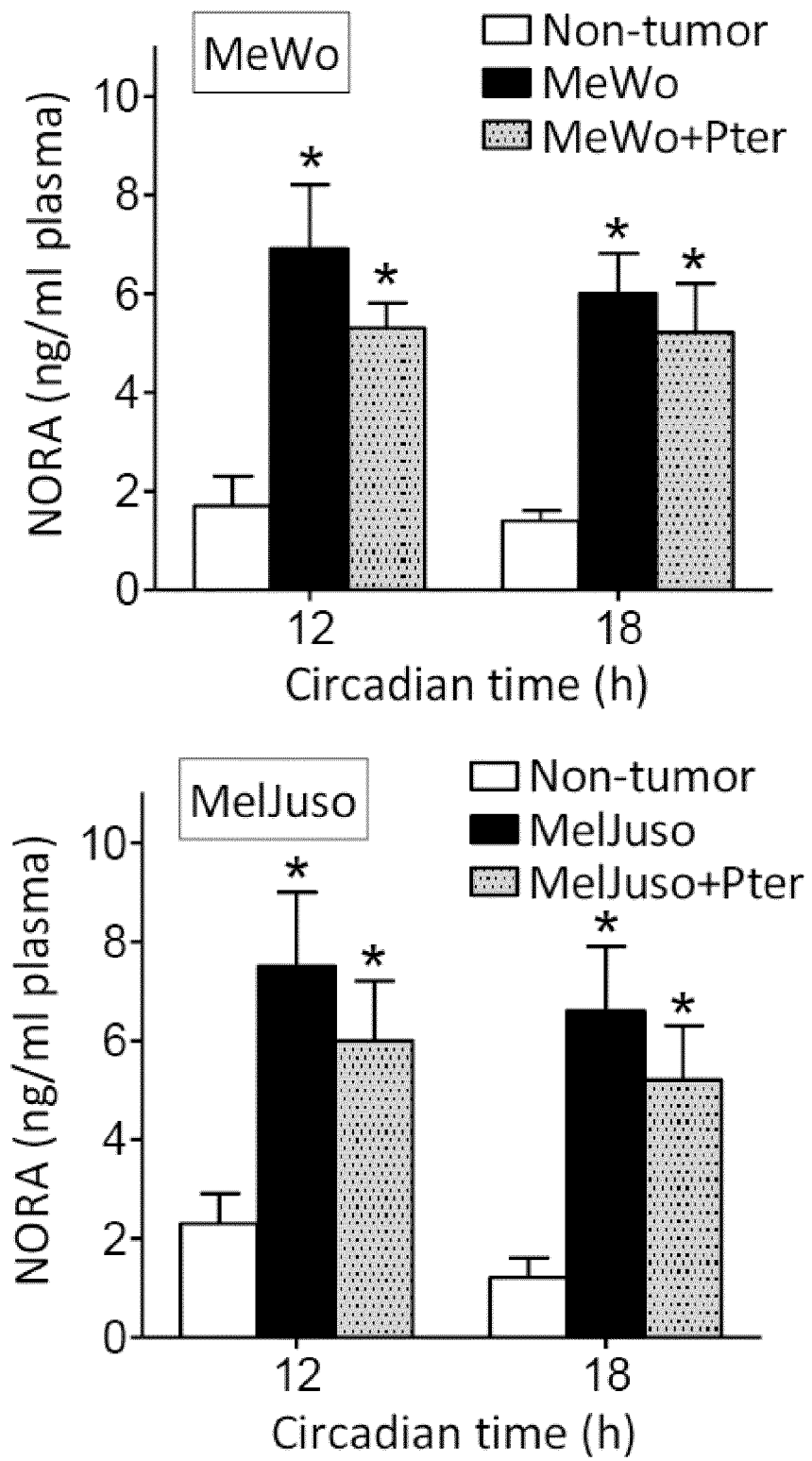

Stress-relative responses in rodents under stressful conditions can be evaluated by measuring plasma levels of corticosterone and noradrenaline (NORA) (main circulating glucocorticoid and catecholamine, respectively). As shown in FIG. 2A, corticosterone levels in plasma of control non-tumor-bearing mice peak at 12 h, just before the begin of the dark active phase in mice. However, in melanoma-bearing mice corticosterone levels were higher than in controls, and remained rather constant along the 24 h-period (FIG. 2A). Treatment with pterostilbene (30 mg/kg every 48 h, as in FIG. 1A) induced a decrease of corticosterone in plasma of melanoma-bearing mice to practically control values (FIG. 2A). Adrenocorticotropin hormone (ACTH) levels also followed a circadian pattern in control non-tumor-bearing mice ACTH was higher before corticosterone levels peaked, and lower during the dark active phase) (FIG. 2B). ACTH levels were also higher in melanoma-bearing mice than in controls, and were also decreased by pterostilbene treatment (FIG. 2B) [-pterostilbene can cross the blood-brain barrier]. Therefore changes in plasma corticosterone levels follow those of ACTH, which stimulates synthesis and release of glucocorticoids from the adrenal glands. However, CRH mRNA expression in the hypothalamic paraventricular nucleus (PVN) was lower in melanoma-bearing mice (FIG. 2C) (in agreement with a similar finding in mice bearing highly metastatic B16-F10 melanoma). This apparent biological paradox (a decrease in CRH associated with an increase in ACTH) can be explained e.g. by a direct activation of pituitary ACTH production elicited by melanoma-released IL-6. However pterostilbene treatment caused a further decrease in CRH expression, which was statistically significant in MeWo- and MelJuso-bearing mice (FIG. 2C). A fact in agreement with recent reports showing that natural hesperidin (a polyphenolic flavanone glycoside) or quercetin (a polyphenolic flavonol), also decrease mRNA CRH expression in rat models of chronic or acute stress, respectively. Hence, since CRH expression is lower in melanoma-bearing mice than in non-tumor-bearing mice, whereas ACTH increases, the Pter-induced decrease in corticosterone generation appears mainly due to a Pter-induced inhibition of pituitary ACTH production.

NORA levels in plasma were also higher in melanoma-bearing mice than in control non-tumor-bearing mice (FIG. 2D). However, NORA levels were not significantly different when melanoma-bearing mice, treated or not treated with Pter, were compared (FIG. 2D).

Pterostilbene Inhibits ACTH Production in AtT-20 Cells.

In order to assay if pterostilbene directly affects ACTH production AtT-20, an ACTH secreting cell line cloned from cultures established after alternate passage of mouse pituitary tumor cells as tumors in animals and in cell culture (see www.lgcstandards-atcc.org) was used as a model. As shown in FIG. 3A, pterostilbene levels in mouse whole brain peak 5 min after its i.v. administration (30 mg/kg), and then rapidly decrease to approx. 1 nmol/g at 60 min and to non-detectable levels at 120 min. To assay if these levels may reflect pharmacokinetics within the pituitary gland a parapharyngeal approach, modified by Hof et al. (Hoff, J. B. et al, K. *J Am Assoc Lab Anim Sci* 45, 57-62 (2006)) from previously published surgical techniques was used to rapidly perform hypophysectomy in Pter-treated mice. As shown in FIG. 3A, pterostilbene levels in the hypophysis follow a similar pattern, as compared with the whole brain, but were found significantly higher. Hypothetically this may reflect the fact that the pituitary gland is the most irrigated region of the body (blood flow: 0.8 ml/g×min).

The effect of pterostilbene on ACTH production was measured in cultured AtT-20 cells. As shown in FIG. 3B, pterostilbene (15 µM, an approx. mean value of the pterostilbene levels measured in the hypophysis 10-30 min after i.v. administration of 30 mg/kg, see the caption), indeed decreases ACTH production.

Proopiomelanocortin (POMC) is a common precursor of melanocortin-related peptides in the pituitary and primarily regulated by CRH. ACTH is produced in pituitary corticotrophs when POMC is cleaved to β-lipotropic hormone and ACTH by the prohormone convertase-1/3 processing enzyme. Pterostilbene also decreased POMC expression and levels in AtT-20 cultured cells (FIGS. 3C and 3D). Thus further indicating that pterostilbene suppresses ACTH synthesis and secretion in corticotroph cells, as suggested by the data displayed in FIG. 2. None of the main pterostilbene conjugates (Pter-S and Pter-G) decreased ACTH production in AtT-20 cells (results not shown). Thus indicating that the natural structure, and not its in vivo generated metabolites, is responsible of inhibiting ACTH production.

Exogenous Administration of Corticosterone Antagonizes the Effect of Pterostilbene on Melanoma Growth.

Does the Pter-induced decrease in circulating glucocorticoids affect melanoma growth? Human melanoma cells express high-affinity GR. As shown in Table 4 treatment with pterostilbene reduced circulating corticosterone levels and melanoma growth in all models assayed, but without affecting the number of GR. However pterostilbene was unable to significantly affect in vivo melanoma growth if mice received at the same time a constant i.v. infusion of exogenous corticosterone (which resets its pathophysiological levels in melanoma-bearing mice) (Table 2). Therefore, since pterostilbene does not directly affect melanoma growth under in vitro conditions (FIG. 1C), our results suggest that Pter-induced inhibition of melanoma growth indirectly requires glucocorticoids and, consequently, GR-derived intracellular signaling.

TABLE 4

GR number in growing melanoma cells in mice treated with pterostilbene and/or corticosterone (CRC)

| Treatment | A2058 | | | MeWo | | | MelJuso | | |
|---|---|---|---|---|---|---|---|---|---|
| | Tumor vol. (mm$^3$) | $10^3$ GR/cell | CRC (ng/mL plasma) | Tumor vol. (mm$^3$) | $10^3$ GR/cell | CRC (ng/mL plasma) | Tumor vol. (mm$^3$) | $10^3$ GR/cell | CRC (ng/mL plasma) |
| None | 1049 ± 267 | 73 ± 6 | 247 ± 36 | 507 ± 166 | 52 ± 4 | 195 ± 35 | 286 ± 69 | 55 ± 5 | 179 ± 37 |
| Pter | 258 ± 66* | 71 ± 5 | 123 ± 29* | 167 ± 53* | 45 ± 6 | 87 ± 17* | 145 ± 35* | 47 ± 4 | 80 ± 15* |
| CRC | 857 ± 185 | 80 ± 7 | 205 ± 48 | 426 ± 116 | 49 ± 7 | 177 ± 29 | 240 ± 94 | 46 ± 6 | 164 ± 41 |
| Pter + CRC | 906 ± 214 | 72 ± 5 | 196 ± 37 | 451 ± 159 | 50 ± 5 | 186 ± 35 | 229 ± 77 | 51 ± 5 | 175 ± 35 |

Melanoma cells stably expressing the red fluorescence protein (RFP) were inoculated, as in FIG. 1, and allowed to grow for 35 days. Treatment with pterostilbene (as in FIG. 1) and/or costicosterone [using ALZET minipumps (ALZET Osmotic Pumps, Cupertino, CA) and jugular vein catheterism (following manufacturer's instructions); the mean rate of infusion was of 0.3 μg of corticosterone/h] started 1 week after tumor inoculation. Treatment of tumor-bearing mice with vehicles (DMSO-ethanol for pterostilbene as indicated under Methods; or polyethylene glycol 400 for corticosterone) did not significantly affect the rate of melanoma growth as compared to controls (not shown). The number of GR (expressed as binding sites/cell) was not significantly different when 72 h-cultured A2058-RFP, MeWo-RFP or MelJuso-RFP cells were compared with their wild type A2058, MeWo or MelJuso cell counterparts (not shown). Data for GR number, tumor volume (Tumor vol.) and corticosterone (blood samples were obtained at 12 h circadian time, see FIG. 2) displayed in this table were obtained 35 days after tumor inoculation. All tumors had 50-70 mm$^3$ of volume on day 7 after inoculation. GR number on day 7 was not significantly different from GR number on day 35 (not shown). Data are mean values ± SD of 6-7 different animals.
*Significantly different p < 0.01 comparing all groups vs controls (untreated). Data obtained in melanoma-bearing mice treated with vehicle were not significantly different from those calculated for the untreated group (not shown).

TABLE 5

Effect of pterostilbene treatment on different Nrf2- and redox state-related enzyme activities and metabolites in melanoma cells growing in vivo

| | | A2058 | | MeWo | | MelJuso | |
|---|---|---|---|---|---|---|---|
| | | — | +Pter | — | +Pter | — | +Pter |
| GSH and TXN | GCL (mU/10$^6$ cells) | 133 ± 25 | 58 ± 17† | 77 ± 19 | 35 ± 12† | 112 ± 31 | 49 ± 12† |
| | GSS (mU/10$^6$ cells) | 16.3 ± 4.7 | 8.5 ± 2.0* | 12.4 ± 3.6 | 7.4 ± 1.6* | 13.6 ± 2.4 | 7.8 ± 1.5† |
| | GPX (mU/10$^6$ cells) | 6.1 ± 2.2 | 3.9 ± 1.1 | 4.6 ± 2.0 | 2.8 ± 1.0 | 5.3 ± 1.7 | 2.1 ± 0.5† |
| | GSR (mU/10$^6$ cells) | 10.0 ± 3.0 | 6.1 ± 1.6 | 8.5 ± 1.7 | 4.9 ± 1.2* | 9.0 ± 3.0 | 5.1 ± 1.0† |
| | GST (mU/10$^6$ cells) | 15.1 ± 2.8 | 7.5 ± 1.3† | 10.3 ± 2.2 | 6.5 ± 1.3* | 7.8 ± 1.5 | 4.7 ± 1.3* |
| | GGT (mU/10$^6$ cells) | 20.5 ± 4.5 | 19.6 ± 2.7 | 15.3 ± 3.7 | 16.0 ± 2.4 | 17.5 ± 3.4 | 15.9 ± 3.5 |
| | GSH (nmol/10$^6$ cells) | 22.4 ± 3.9 | 10.5 ± 2.1† | 12.3 ± 2.9 | 7.3 ± 1.7† | 19.6 ± 3.7 | 10.8 ± 2.9† |
| | GSSG (nmol/10$^6$ cells) | 0.3 ± 0.1 | 0.3 ± 0.1 | 0.1 ± 0.05 | 0.1 ± 0.03 | 0.1 ± 0.03 | 0.1 ± 0.04 |
| | TXN (μg/10$^6$ cells) | 1.0 ± 0.3 | 0.5 ± 0.1* | 1.4 ± 0.4 | 0.8 ± 0.2* | 0.9 ± 0.2 | 0.3 ± 0.1† |
| | TXNRD (U/10$^6$ cells) | 1.3 ± 0.3 | 0.7 ± 0.2* | 1.6 ± 0.3 | 0.9 ± 0.2† | 1.2 ± 0.3 | 0.6 ± 0.1† |
| ROS | SOD1 (U/10$^6$ cells) | 1.5 ± 0.5 | 0.6 ± 0.2† | 1.1 ± 0.3 | 0.5 ± 0.2* | 0.8 ± 0.2 | 0.4 ± 0.2* |
| | SOD2 (U/10$^6$ cells) | 0.3 ± 0.1 | 0.1 ± 0.05† | 0.2 ± 0.1 | 0.1 ± 0.05 | 0.2 ± 0.05 | 0.1 ± 0.05* |
| | CAT (mU/10$^6$ cells) | 3.8 ± 0.7 | 1.7 ± 0.3† | 2.7 ± 0.4 | 1.6 ± 0.4† | 3.9 ± 1.1 | 1.1 ± 0.3† |
| | NOX (R.L.U./10$^6$ cells) | 162 ± 38 | 177 ± 4.5 | 146 ± 37 | 132 ± 25 | 155 ± 26 | 142 ± 37 |
| | H$_2$O$_2$ (nmol/10$^6$ cells × min) | 1.2 ± 0.4 | 0.7 ± 0.2† | 1.5 ± 0.3 | 0.7 ± 0.2† | 1.6 ± 0.4 | 0.8 ± 0.2† |
| | O$_2^-$ (ΔFL1, a.u.) | 2.4 ± 0.5 | 3.9 ± 0.6* | 2.9 ± 0.8 | 3.5 ± 0.7 | 3.2 ± 0.7 | 5.0 ± 1.3* |
| NADPH supplying dehydrogenases | G6PDH (mU/10$^6$ cells) | 660 ± 113 | 305 ± 78† | 437 ± 55 | 266 ± 39† | 512 ± 49 | 366 ± 63† |
| | ME (mU/10$^6$ cells) | 76 ± 16 | 43 ± 12† | 44 ± 11 | 32 ± 11 | 38 ± 12 | 25 ± 7† |
| | IDH (U/10$^6$ cells) | 2.2 ± 0.5 | 1.2 ± 0.4* | 2.4 ± 0.4 | 1.5 ± 0.4* | 2.6 ± 0.4 | 1.5 ± 0.4† |
| Redox state | NADPH (nmol/mg prot) | 0.14 ± 0.2 | 0.06 ± 0.02† | 0.12 ± 0.06 | 0.05 ± 0.002* | 0.11 ± 0.3 | 0.05 ± 0.02† |
| | NADP$^+$ (nmol/mg prot) | 0.01 ± 0.005 | 0.05 ± 0.01† | 0.01 ± 0.005 | 0.04 ± 0.01† | 0.005 ± 0.001 | 0.03 ± 0.01 |
| | GSH/GSSG | 75 ± 6 | 35 ± 5† | 123 ± 11 | 73 ± 11† | 196 ± 21 | 108 ± 17† |
| | NADPH/NADP$^+$ | 14.1 ± 2.1 | 1.2 ± 0.3† | 12.0 ± 3.5 | 1.2 ± 0.2† | 22.0 ± 4.2 | 1.7 ± 0.3† |

Tumor-bearing mice were treated as in FIG. 1a. All parameters (see under Methods) were measured in melanoma cells isolated from tumors 35 days after inoculation. Data are mean values ± SD for 7-8 different tumors per parameter and experimental condition.
*Significantly different p < 0.05,
†p < 0.01.

Effect of Pterostilbene Treatment on the Nrf2-Dependent Antioxidant System in Growing Melanomas.

Figure 4:
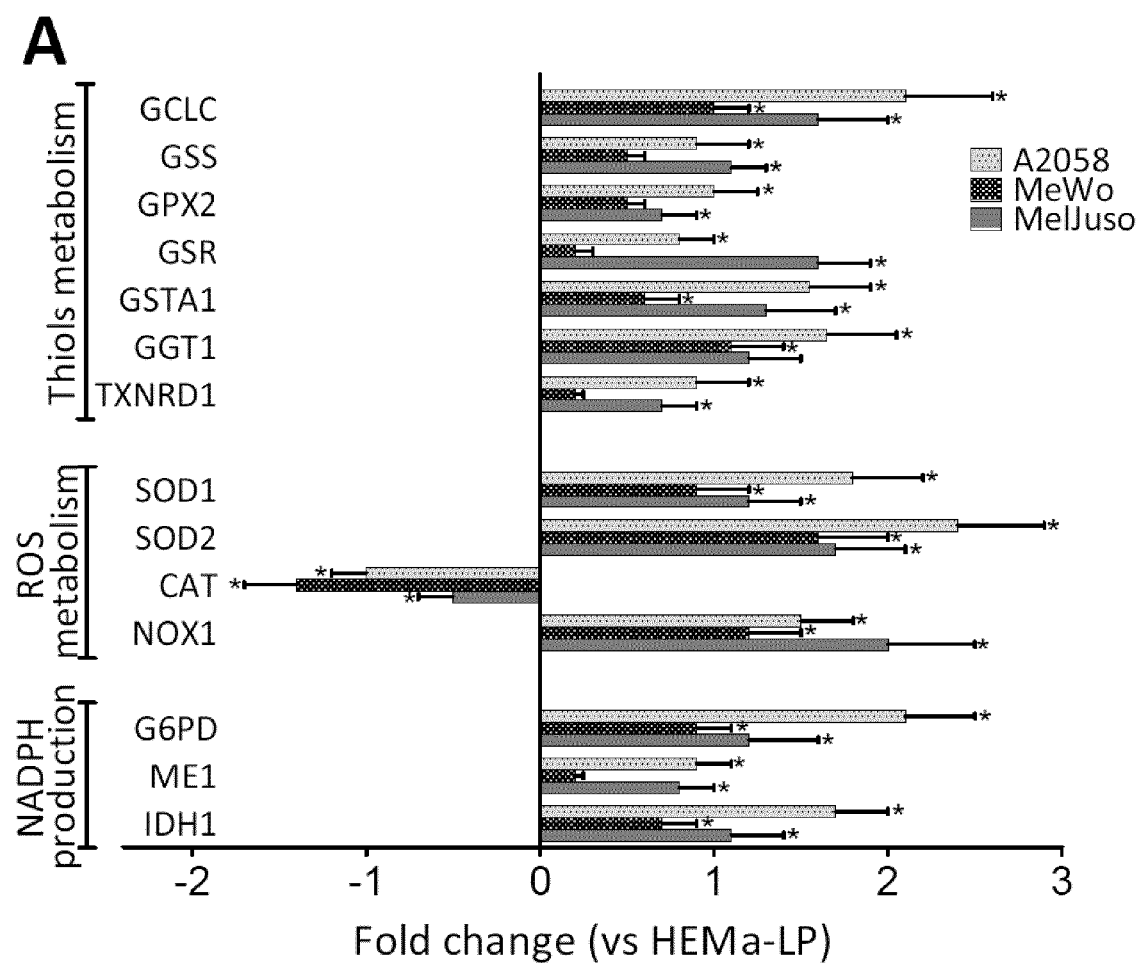
FIG. 4. Effect of pterostilbene treatment on nuclear Nrf2 and its transcription activity in melanoma-bearing mice. (A) Expression of different Nrf2-dependent genes in A2058-RFP, MeWo-RFP and MelJuso-RFP cells, isolated by laser microdissection (as indicated under Methods) from in vivo growing tumors 35 days after tumor inoculation, was compared vs 48 h-cultured HEMa-LP cells (*Significantly different p<0.05). (B) Expression of the same genes was compared in in vivo growing A2058-RFP, MeWo-RFP and MelJuso-RFP cells treated and untreated with pterostilbene (as in FIG. 1A) (*Significantly different p<0.05). All data for (A) and (B), expressing fold change (quantitative RT-PCR, see under Methods for calculations), show mean values±SD for 5-6 different experiments. No significant differences in expression of the genes displayed were found when control A2058, MeWo and MelJuso cells and their RFP counterparts were compared under in vitro conditions (not shown). (C) Nuclear accumulation of Nrf2 from in vivo growing A2058-RFP, MeWo-RFP and MelJuso-RFP cells was measured by Western blotting (no significant differences were found when these data were compared with those found in control A2058, MeWo and MelJuso cells, not shown) (mean values±SD for 5 different experiments, *Significantly different p<0.01 comparing pterostilbene treatment vs controls). (D) Effect of Nrf2 overexpression (see under Methods) on the tumor growth of control and Pter-treated (as in FIG. 1A) A2058-bearing mice. Results obtained in these cells transfected with lentiviral vector not harboring any gene (negative control) were not different from control values (not shown). Data are mean values±SD from 6-7 different experiments (*Significantly different p<0.01, comparing pterostilbene treatment vs controls; no significant differences were found when A2058/Tet-Nrf2 cells, ±pterostilbene treatment, were compared with control A2058 untreated cells).
Figure 4:
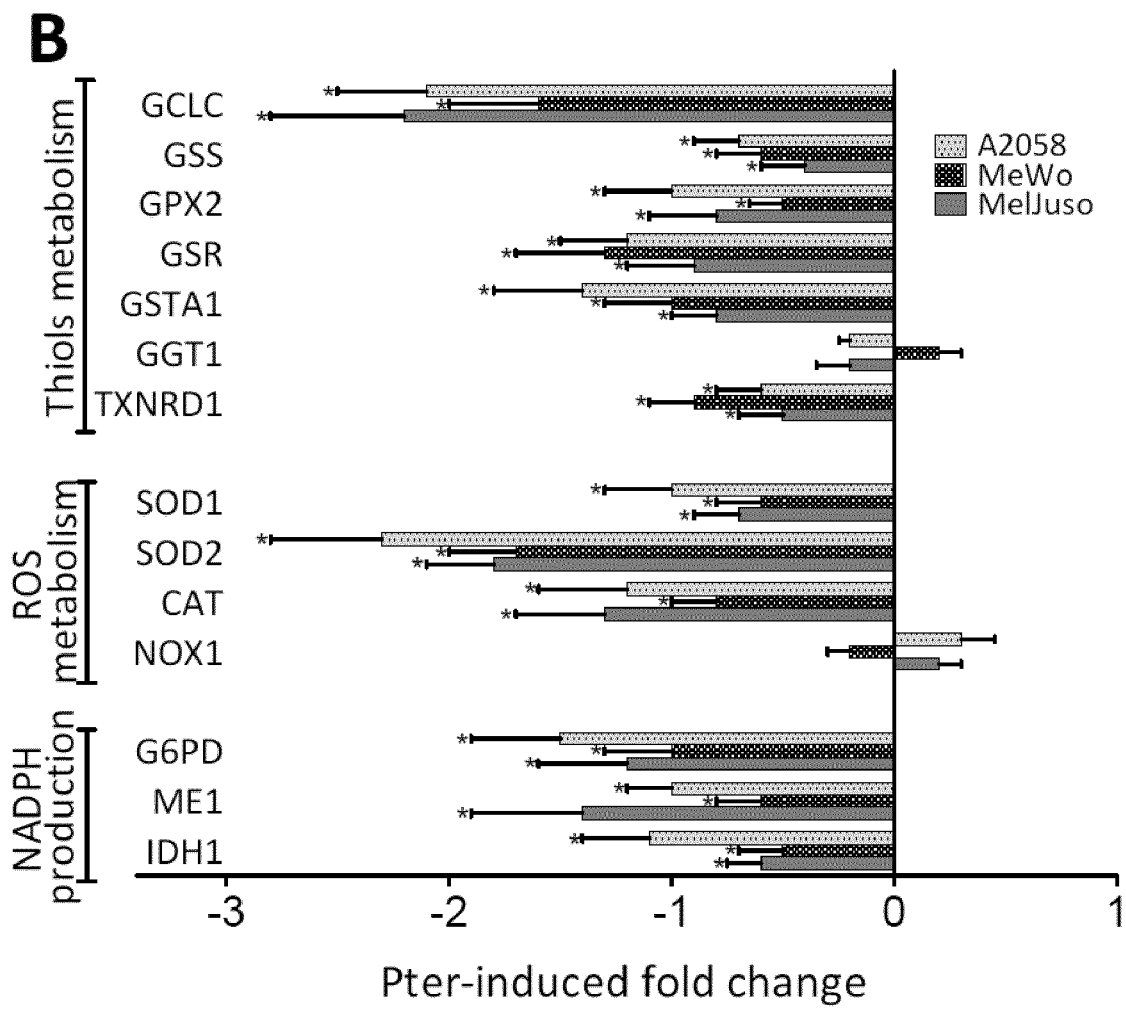
Figure 4:
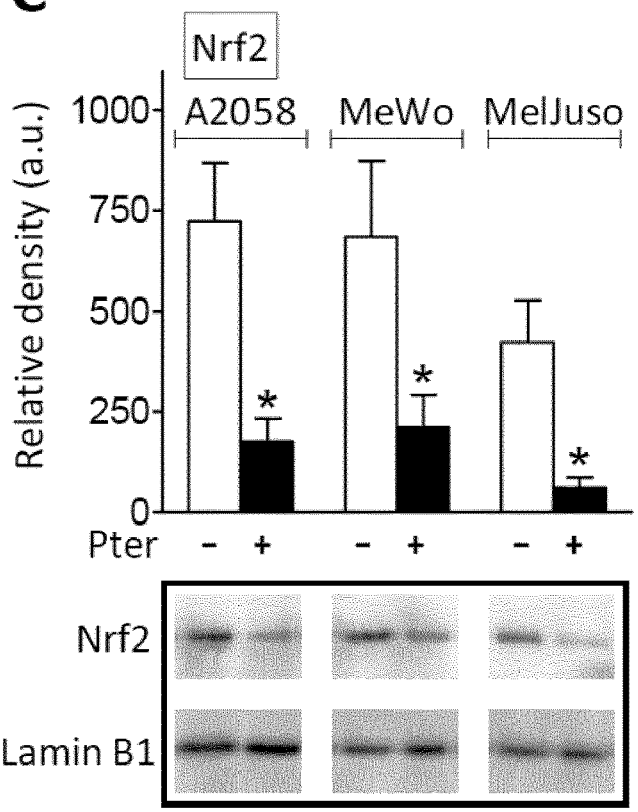
Figure 4:
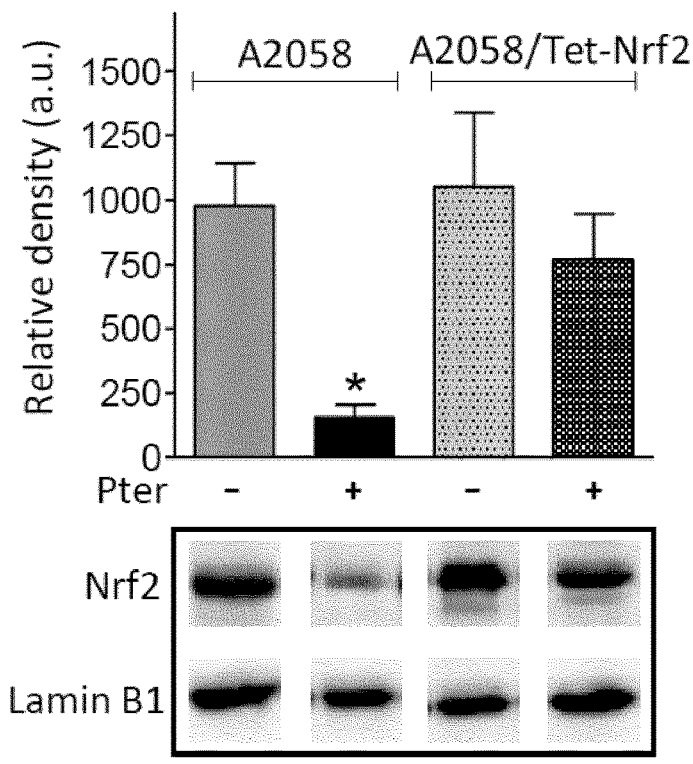
Figure 4:
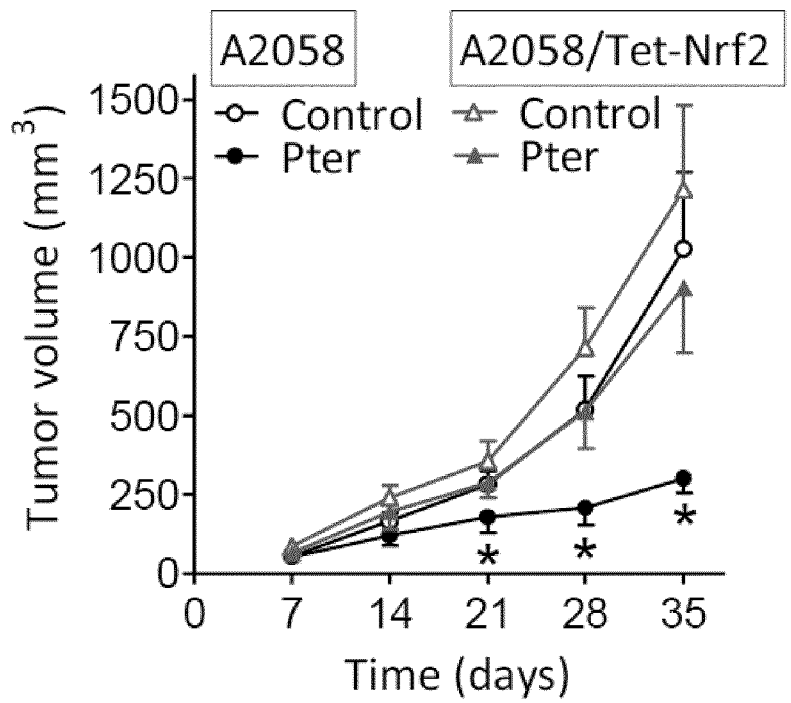

The inventors recently reported that GR knockdown decreases the antioxidant protection of highly metastatic B16-F10 melanoma cells, where Nrf2 [nuclear factor (erythroid-derived 2)-like 2] and p53 down-regulation associated with a decrease in expression and activity of: γ-glutamyl-cysteine ligase (GCL), superoxide dismutases (SOD) 1 and 2, catalase (CAT), glutathione peroxidase (GPX), and glutathione reductase (GSR) thereby causing a drastic decrease in the survival of metastatic cells during their interaction with vascular endothelial cells under in vitro and in vivo conditions. However, pterostilbene treatment decreases circulating corticosterone (FIG. 2A) without affecting the number of GR in melanoma cells (Table 2). Therefore it is uncertain whether pterostilbene treatment may also affect the Nrf2-dependent battery of antioxidant and xenobiotic-metabolizing enzymes. As compared to cultured human melanocytes (HEMa-LP), expression of practically all checked Nrf2-dependent enzymes, excepting a decrease in CAT, increases in A2058, MeWo and MelJuso melanoma cells growing in vivo (FIG. 4A). Thus suggesting that cancer cells, as compared to their normal counterparts, tend to reinforce their antioxidant defenses. However, pterostilbene treatment causes a decrease in the expression of all Nrf2-dependent enzymes tested, with some exceptions i.e. GGT1 (γ-glutamyl transpeptidase 1) and NOX1 (NADPH oxidase 1) which appear not affected by the stilbene (FIG. 4B). The Pter-induced decrease in melanoma antioxidant defense was confirmed by measuring many different GSH (glutathione)-, ROS (reactive oxygen species)-, and cellular redox state-related enzyme activities and metabolites (Table 3). As shown in FIG. 4C, and as compared to control melanoma-bearing mice, these effects indeed associate with a decreased in nuclear Nfr2 in melanoma cells from in vivo Pter-treated mice. Moreover, melanoma cells engineered to overexpress Nrf2 were able to grow in vivo as controls despite treatment with pterostilbene (FIG. 4D). These results are relevant for three main reasons: a) pterostilbene treatment decreases the Nrf2-dependent cancer cell defense; b) as previously shown in human lung cancer, Nrf2 enhances cell proliferation and resistance to anticancer drugs; and c) pterostilbene treatment may facilitate identification of potential key targets for melanoma therapy. This could be indeed the case, e.g., for GSH or SOD activities (see FIG. 4B and Table 5). GSH (γ-L-glutamyl-L-cysteinyl-glycine) is the most prevalent non-protein thiol in mammalian cells and multidrug and/or radiation resistance, which are characteristic features of malignant tumors, frequently associated with high GSH content in the cancer cells. Nevertheless the potential advantage of GSH depletion for cancer therapy has never been implemented. Buthionine sulfoximine [BSO, a selective inhibitor of GCL (the rate-limiting step in GSH synthesis) is the only GSH-specific compound that has reached clinical phases (see https://clinicaltrials.gov)]. However, the main limitation for BSO, when administered systemically (i.p. or i.v.), is that it decreases GSH in both tumor and non-tumor tissues. On the other hand the active $O_2^{-\cdot}$ production and low SOD activity in cancer cells were originally suggested to render the malignant cells highly dependent on SOD for survival and sensitive to inhibition of SOD. Based on this background and on our present results, our next step forward was assay the potential efficacy of an experimental therapy involving these potential targets.

Melanoma Cells from Pter-Treated Mice are Highly Sensitive to Combined Chemotherapy and Nrf2-Related Target Therapy.

GSH depletion only appears to be therapeutically effective when very low levels of this tripeptide can be achieved within the cancer cells. Nevertheless, experimentally, GSH can be rapidly depleted using diethylmaleate (DEM, an α,β-unsaturated carbonyl compound). On the other hand, down-regulation of SOD activities can be achieved using a) the known SOD inhibitor diethyldithiocarbamate, but it has antagonistic effects on apoptosis by triggering both cytochrome c release and caspase inhibition and has not been tried in vivo; or b) using antisense oligonucleotides. For these experiments the A2058 cell line bearing BRAFv600E [the most common mutation in melanoma] were used under in vitro controlled conditions. As shown in FIG. 5A, cultured A2058 cells, isolated from Pter-treated mice (30 mg/kg every 48 h for a period of 5 weeks, as in FIG. 1A), were completely eliminated by the combination of DEM-induced GSH depletion and paclitaxel protein-binding particles [PAC.PBP, 100 ng/ml (approx. mean values in human plasma obtained after administration of the standard i.v. dose of 260 mg/m² regularly used in e.g. patients bearing a metastatic breast cancer) (see e.g. www.cancer.gov)]. It is important to remark, as indicated by the data in FIG. 5A, that the combination of DEM and PAC.PBP (as compared to the effect of each drug alone) shows a clear synergy. PAC.PBP was selected, as the best drug candidate against the A2058 melanoma [IC50=0.23±0.04 μM (n=5)], after screening most drugs currently used against melanoma f. As shown in FIG. 5B, the combination of antisense oligonucleotides anti-sod1 (sod1-AS) (which targets the main intracellular SOD activity, see Table 5) and PAC.PBP was less effective. Incubation of A2058 cells, isolated from control (non Pter-treated mice), with DEM and PAC.PBP or sod1-AS and PAC.PBP (as in FIGS. 5A and 5B) only decreased melanoma cell number to 51±12 or 73±7% of control values, respectively; n=5 in both cases, p<0.01) (see Table 6). This proof-of-concept assay suggests the pretreatment with pterostilbene and GSH depletion as an excellent chemosensitizing strategy to be tested against malignant melanoma.

TABLE 6

In vitro effect of DEM and PAC.PBP on isolated A2058 cells (as in FIG. 5A) but without the in vivo treatment with Pter

| Culture time (h) | Control | PAC.PBP | DEM | PAC.PBP + DEM |
|---|---|---|---|---|
| Cell number (×10⁶) | | | | |
| 24 | 0.47 ± 0.07 | 0.50 ± 0.11 | 0.49 ± 0.10 | 0.55 ± 0.07 |
| 36 | 0.53 ± 0.10 | 0.45 ± 0.06 | 0.51 ± 0.05 | 0.29 ± 0.05* |
| 48 | 0.60 ± 0.09 | 0.55 ± 0.09 | 0.56 ± 0.08 | 0.33 ± 0.06* |
| 72 | 0.91 ± 0.05 | 0.83 ± 0.07 | 0.67 ± 0.06* | 0.46 ± 0.11* |
| Cell viability (%) | | | | |
| 72 | 98 ± 1 | 96 ± 2 | 96 ± 2 | 67 ± 5* |

*p < 0.01 comparing all conditions versus controls

Effect of Pterostilbene on Human Breast, Lung, Liver, Prostate, Ovarian, and Colorectal Cancer Growth.

We investigated if Pter administration is effective (as found in melanomas) in other cancers. With this aim we performed further studies using cellular models with genetic backgrounds that reflect the more frequent variants found in patients in each cancer type. Expression of GR in these types of cancers has been also reported, although (even large) differences in GR levels might be expected among patients as suggested by the data found in e.g. patients with advanced non-small cell lung cancer. Our results show that: a) i.v. administration of Pter inhibited xenograft growth in most assayed tumors (FIG. 15); b) GR levels were measured in all tumors (Table 14) and i.v. administration of Pter to mice bearing these types of cancers decreased blood levels of ACTH and corticosterone (Table 13); c) Pter decreased nuclear Nrf2 in all cancer cell types cells under in vivo conditions (FIG. 1) (all having very low or very low levels of GR, Table 13); d) Pter treatment down-regulated GSH levels and GSH- and oxidative stress-related enzyme activities in most cancer cells growing in vivo (Table 14). Therefore the same key effects reported for melanoma cells as illustrated previously also apply for other types of cancers expressing the GR.

Cancer Cells from Pter-Treated Mice are Highly Sensitive to Combined Chemotherapy and GSH-Depleting Agents.

Figure 17:
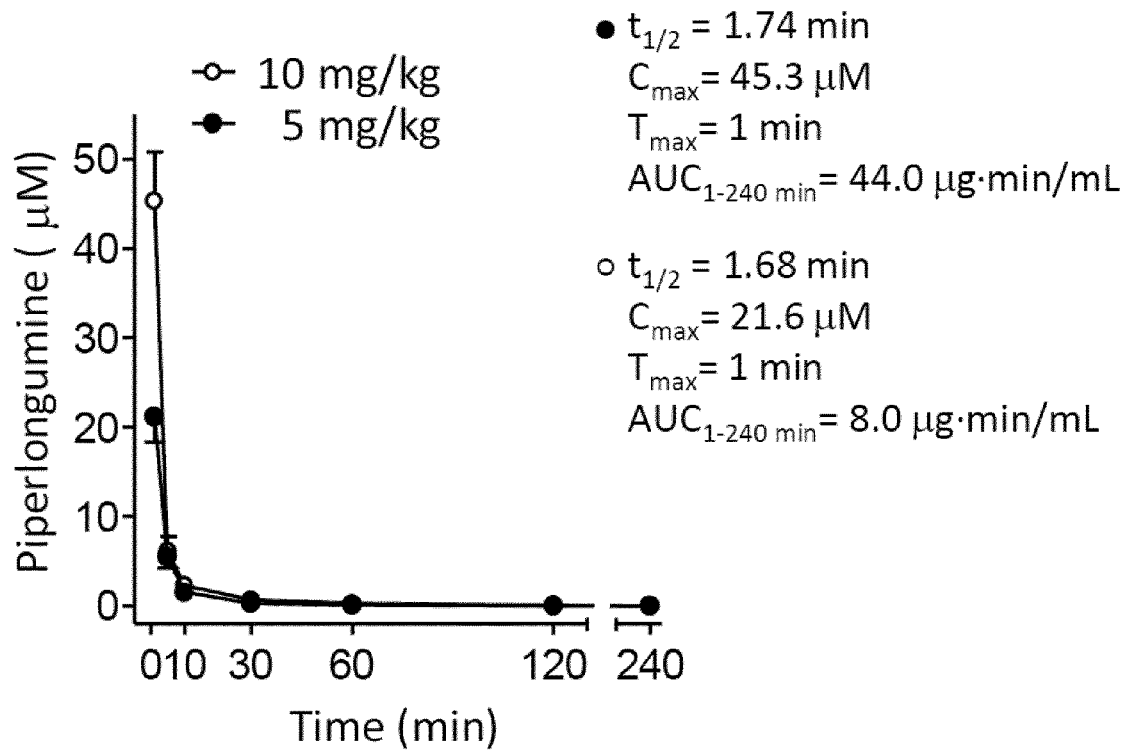
FIG. 17. Plasma levels (A) and pharmacokinetic parameters (B) of piperlongumine (PL) after its i.v. administration to nu/nu mice. PL (5-10 mg/kg) was dissolved in DMSO and administered (10-20 μL) i.v. (tail vein). PL levels were analyzed as described under Methods. Each time point represent the mean±SD (n=5).
Figure 18:
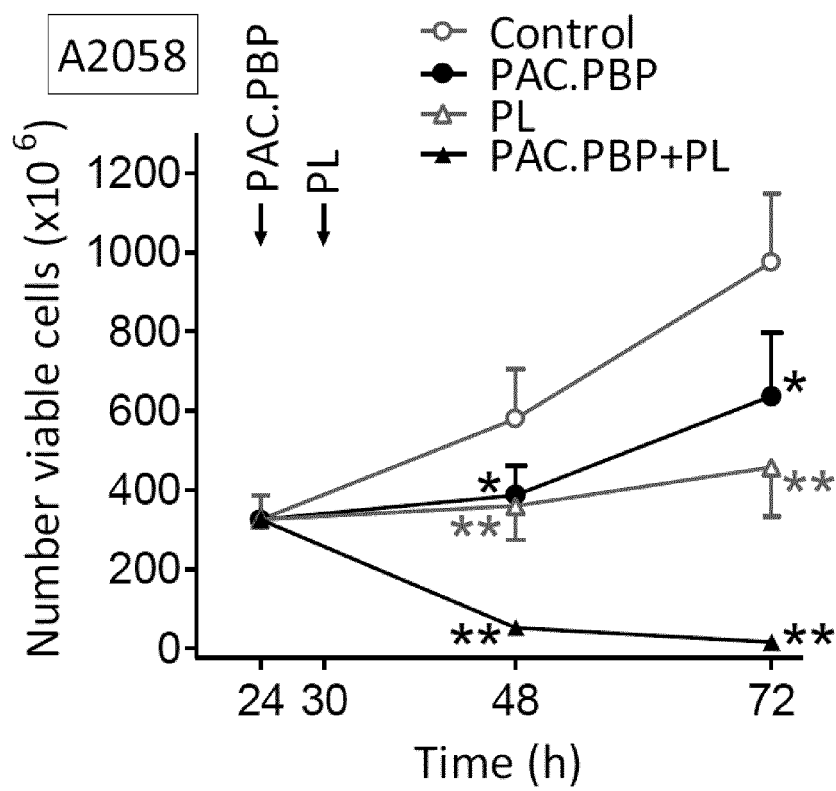
FIGS. 18-25. Effect of piperlongumine and I-BET762, as GSH depleting and chemosensitizing agents, in in vitro growing human melanoma, pancreatic, breast, lung, liver, prostate, ovarian, and colorectal cancer cells. Cancer cells, isolated from Pter-treated tumor-bearing mice, were cultured as indicated under Methods. Chemotherapy (0.25 μM PAC.PBP in A2058 melanoma and MDA-MB-231 breast carcinoma cells; 0.125 μM PAC.PBP and 25 μM GTB in AsPC-1 pancreatic cancer cells; 1 μM VRB and 15 μM cisPt in A459 lung carcinoma cells; 0.15 μM DXR in HepG2 hepatocellular carcinoma cells; 15 nM DCT in PC-3 prostate carcinoma cells; 0.15 μM PAC.PBP and 25 μM CarboPt in SK-OV-3 ovarian carcinoma cells; 3 μM 5-FU, 1 μM FA and 0.6 μM IRI in HT-29 colorectal carcinoma cells) was added to the cultured flasks 24 h after seeding. PL (1 μM in A2058 and AsPC-1 cells; 0.5 μM in A549 and HT-29 cells; 0.2 μM in HepG2, PC-3, and SK-OV-3 cells; 0.1 μM in MDA-MB-231 cells) or I-BET762 (0.5 μM in HT-29 cells; 0.2 μM in A2058, AsPC-1, HepG2, PC-3, and SK-OV-3 cells; 0.1 μM in A549 and MDA-MB-231 cells) were added 6 h later. Data are mean values±SD for 4-5 different experiments per cell line (*p<0.05 and **p<0.01, comparing all experimental conditions versus control. PL, piperlongumine; PAC.PBP, paclitaxel protein-bound particles; GTB, gemcitabine; DXR, doxorubicin; VRB, vinorelbin; CisPt, cisplatin; docetaxel, DCT; CarboPt, carboplatin; 5-FU, 5-fluoracil; FA, folinic acid; IRI, irinotecan; 5-FU+FA+IRI=FOLFIRI).
Figure 18:
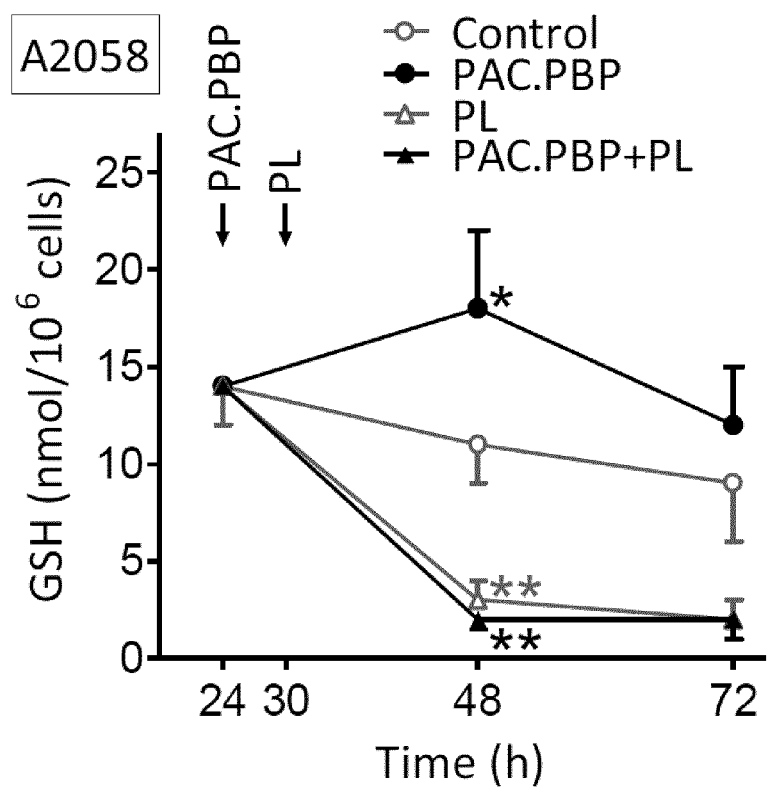
Figure 18:
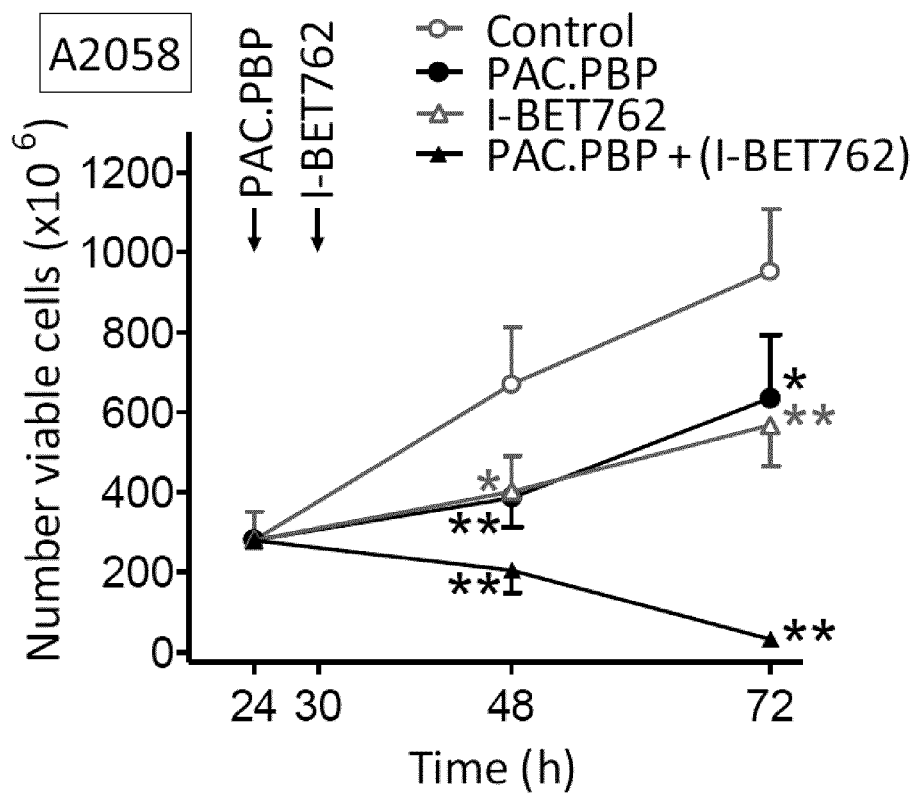
Figure 18:
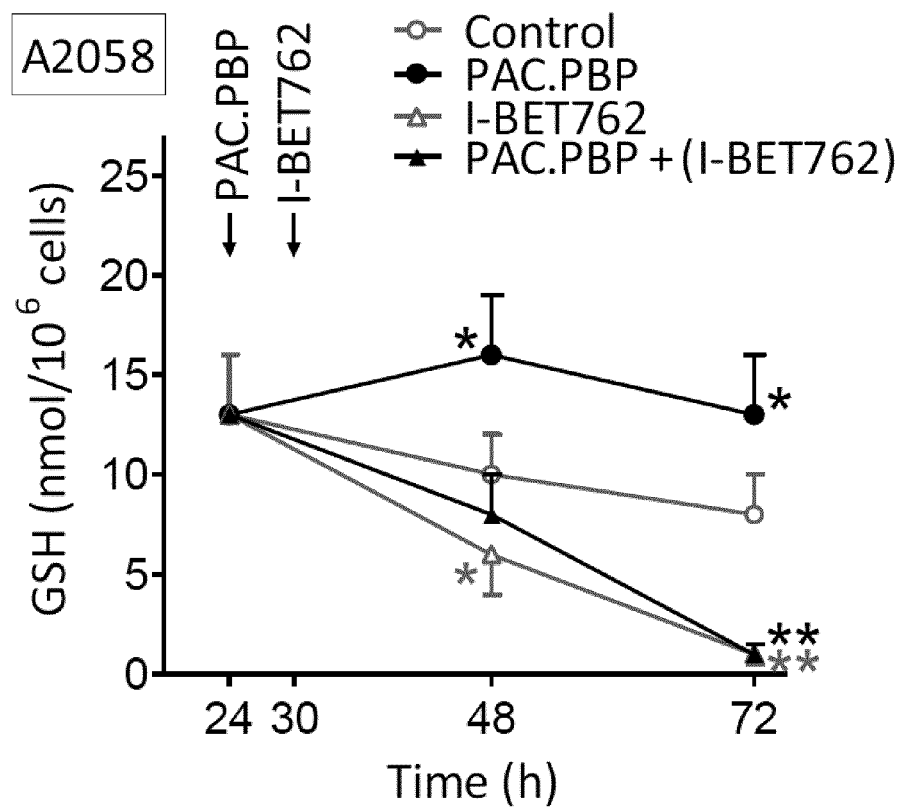
Figure 18:
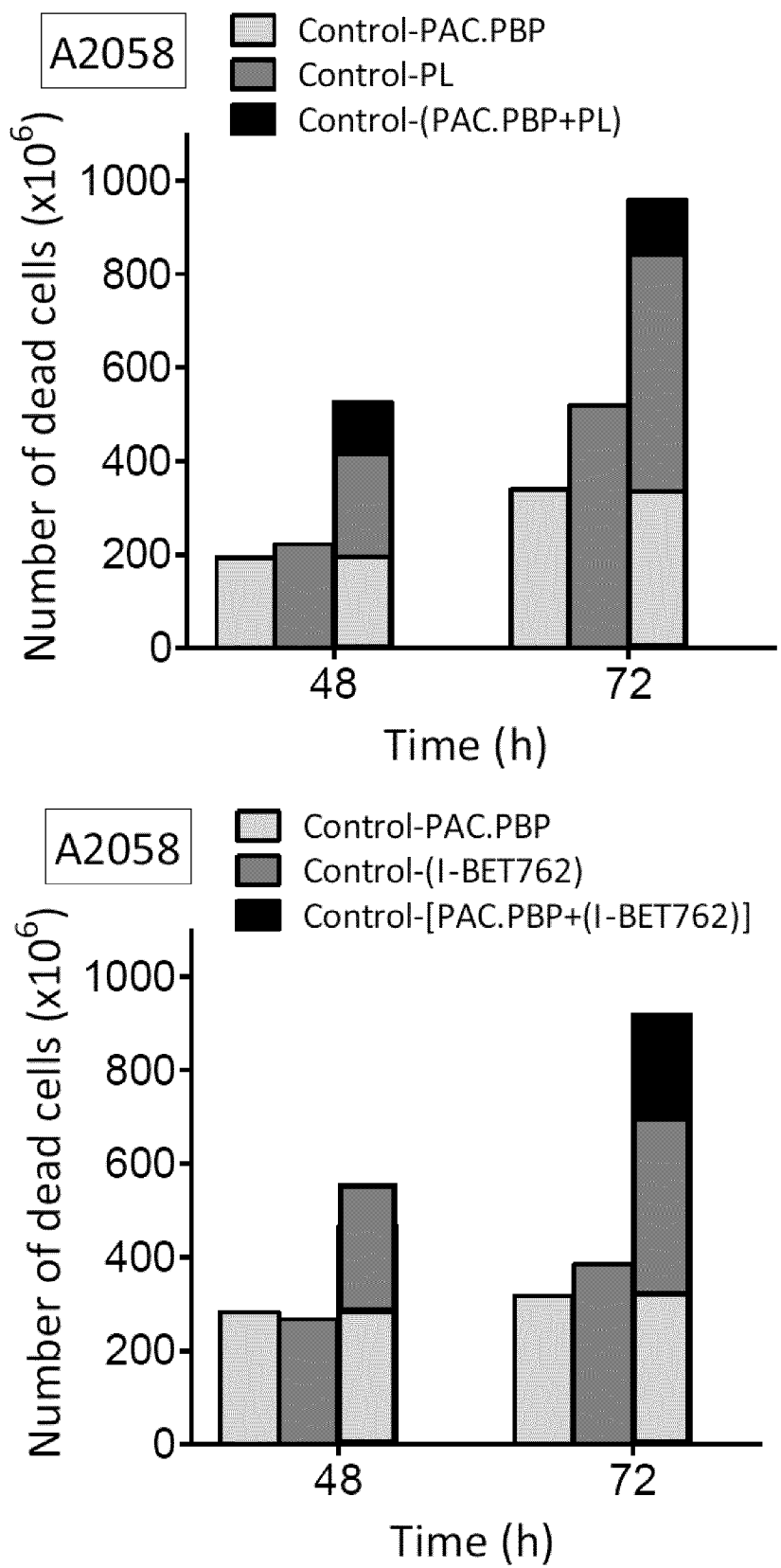
Figure 19:
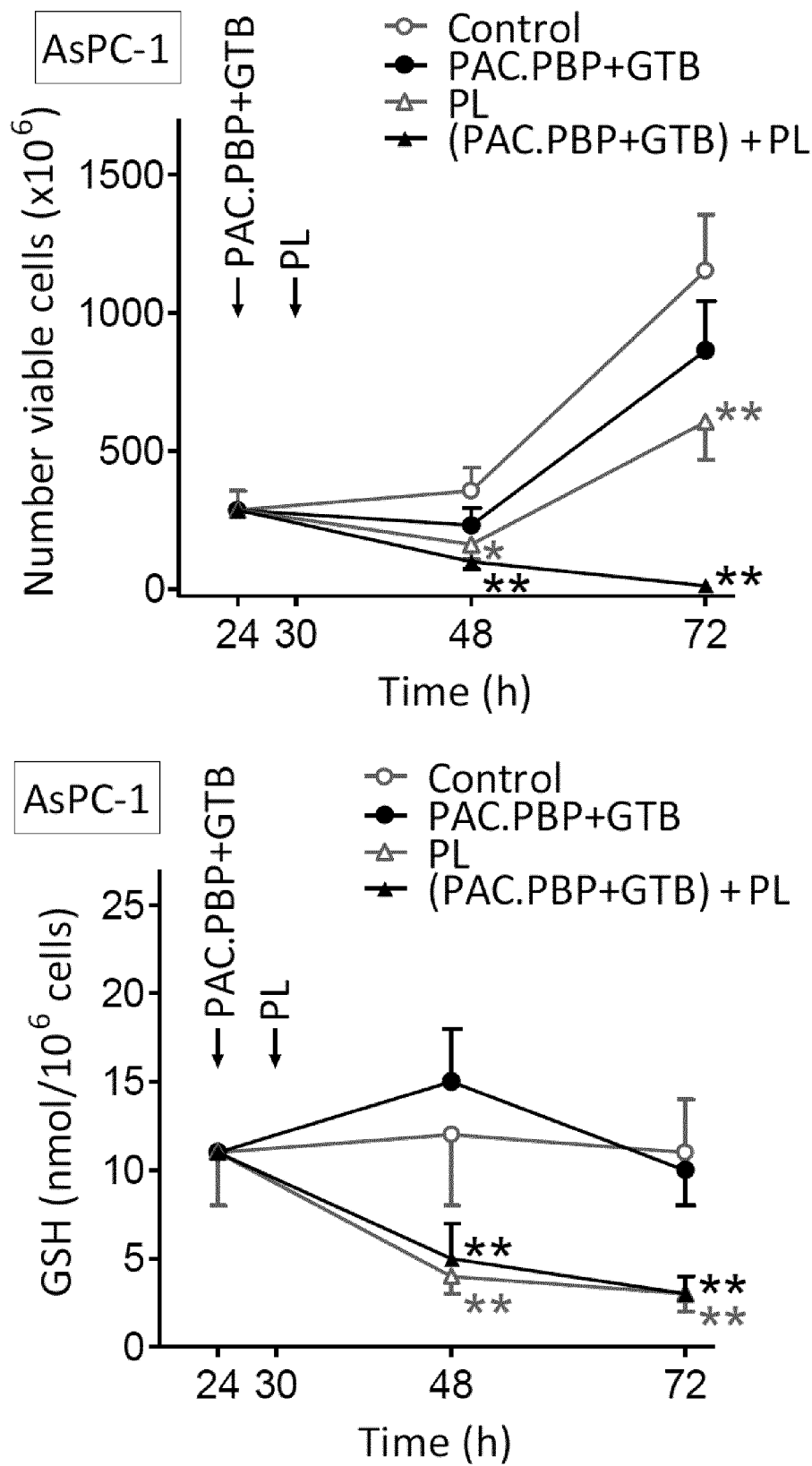
Figure 19:
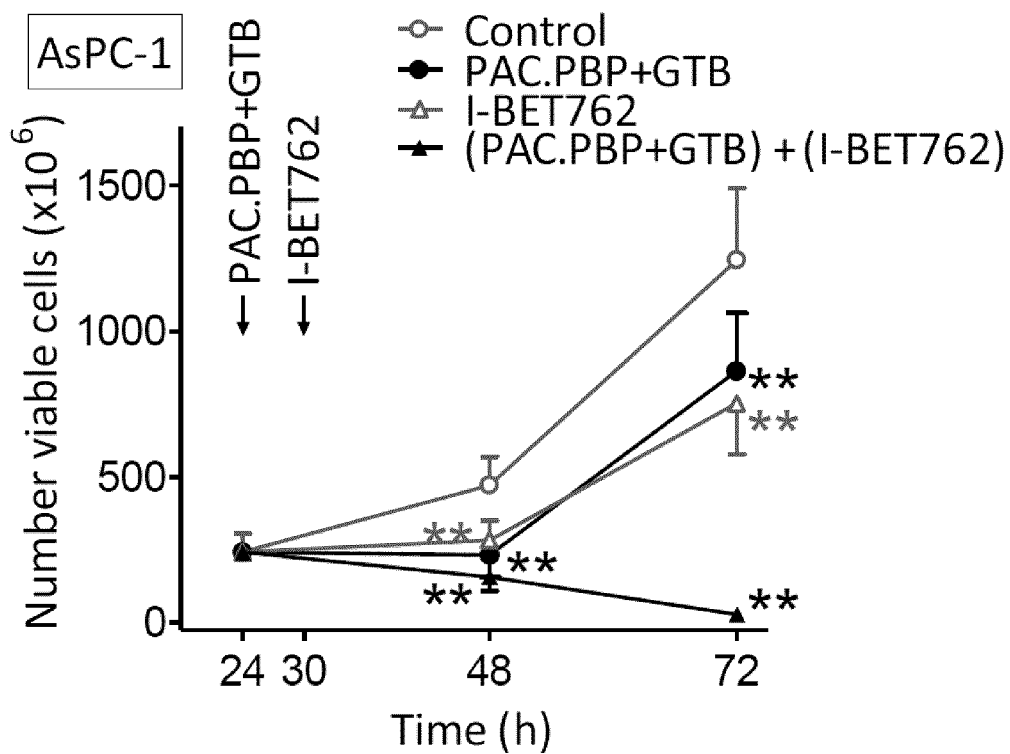
Figure 19:
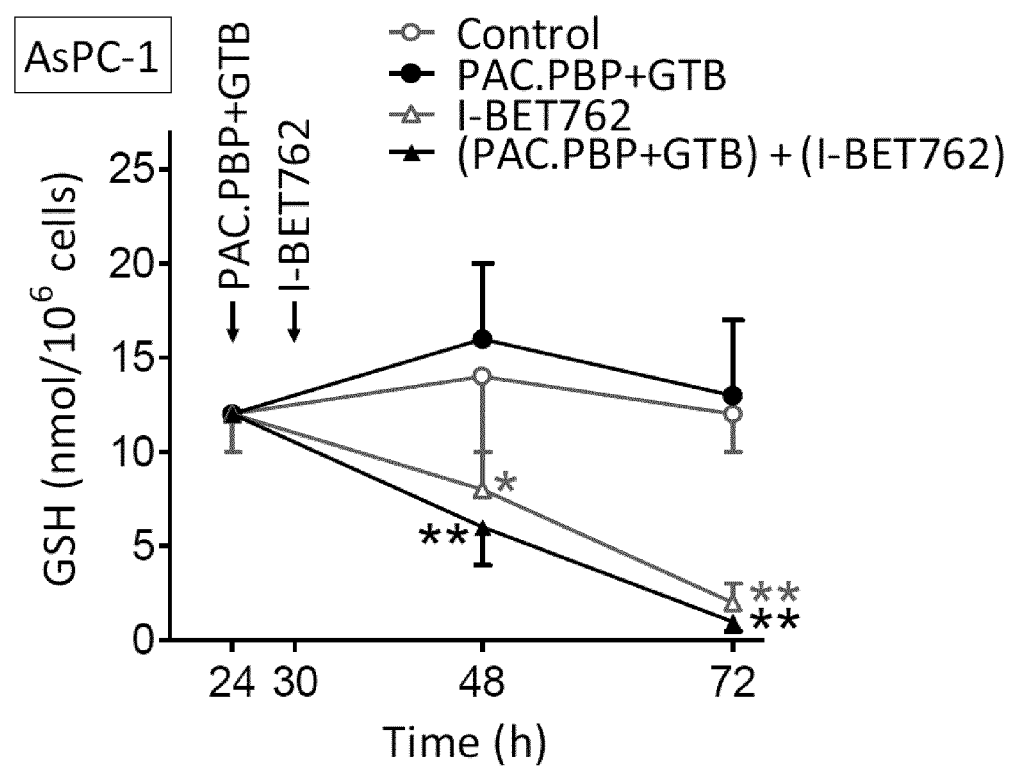
Figure 19:
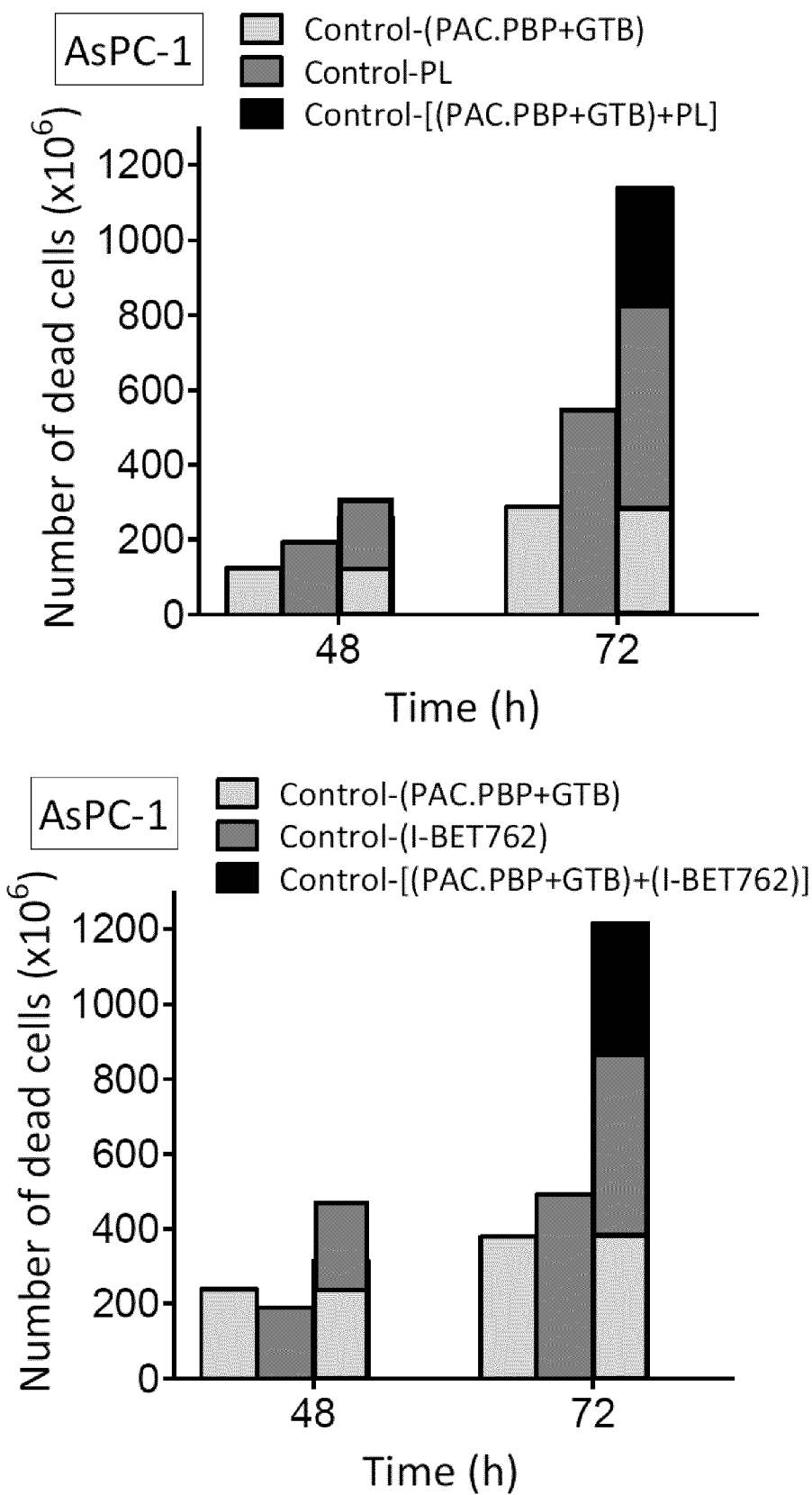
Figure 20:
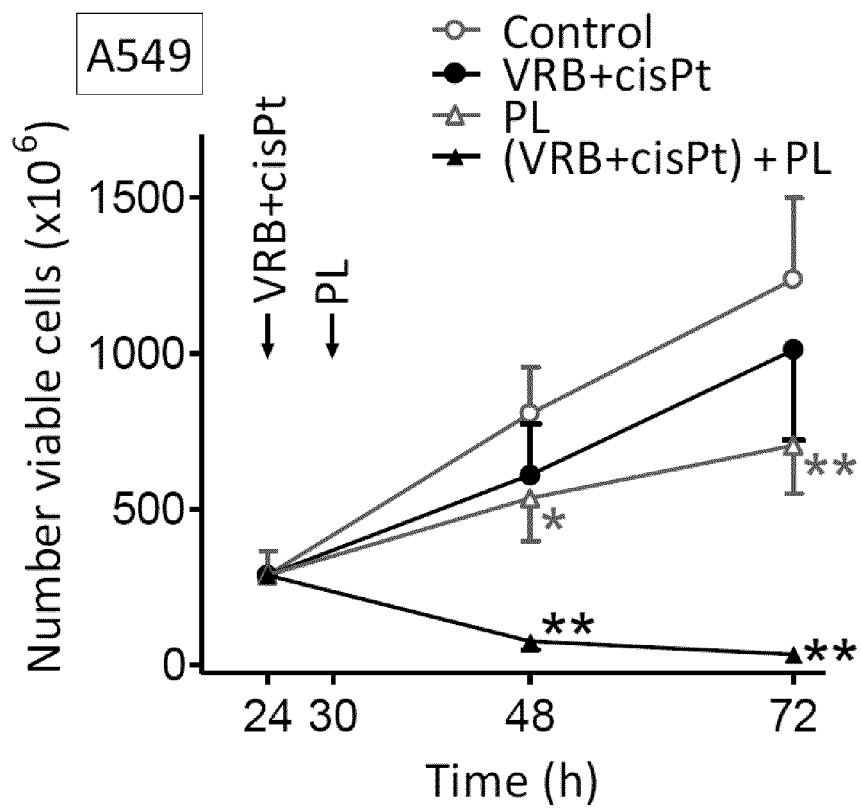
Figure 20:
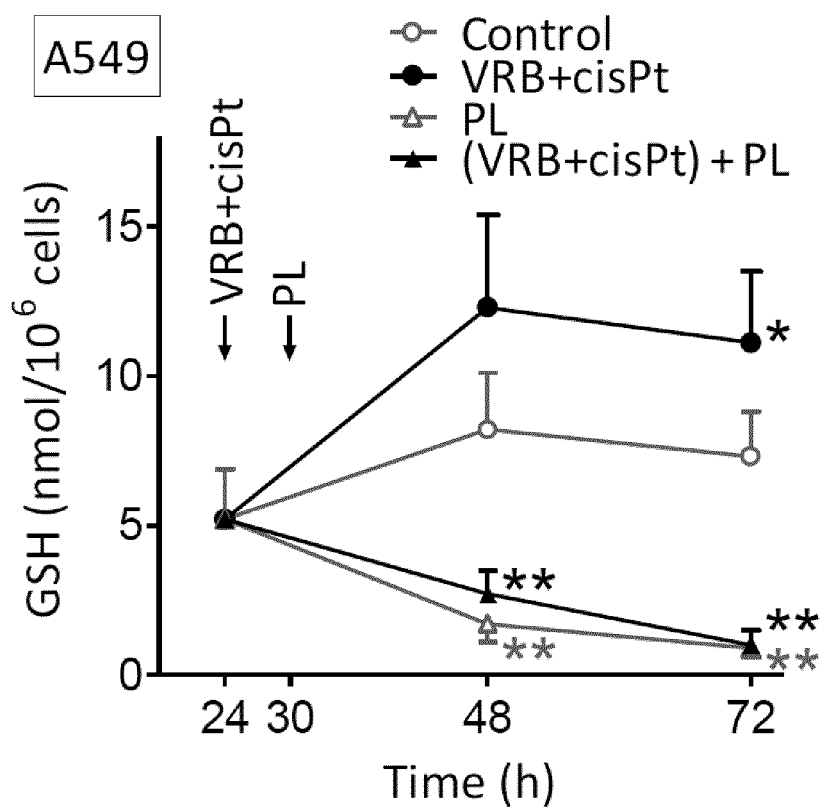
Figure 20:
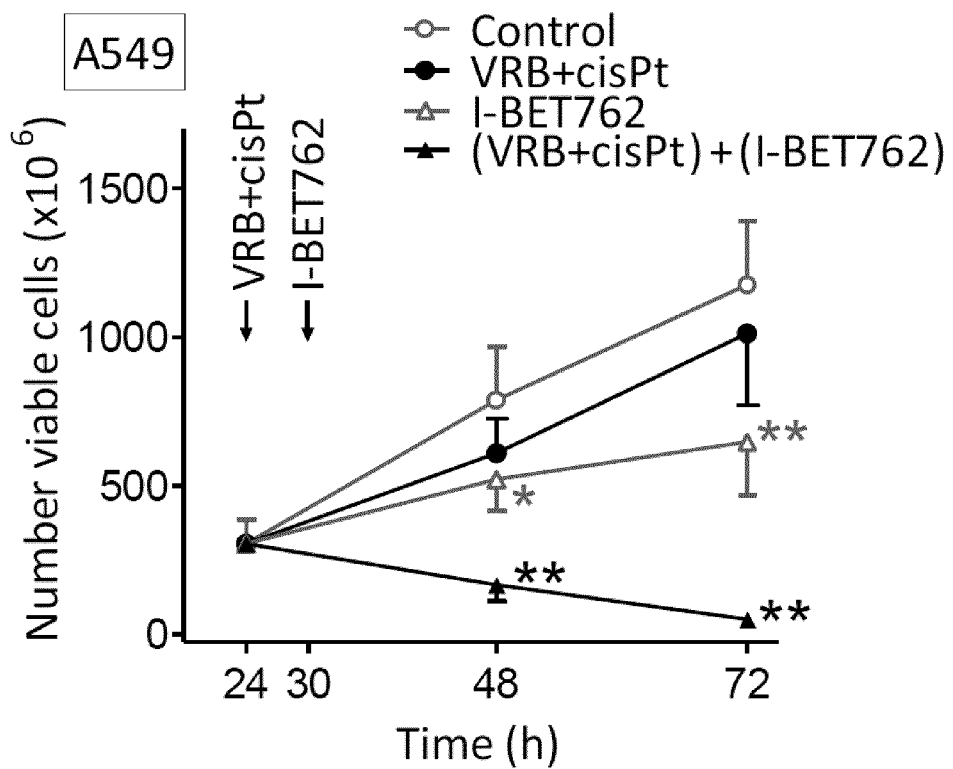
Figure 20:
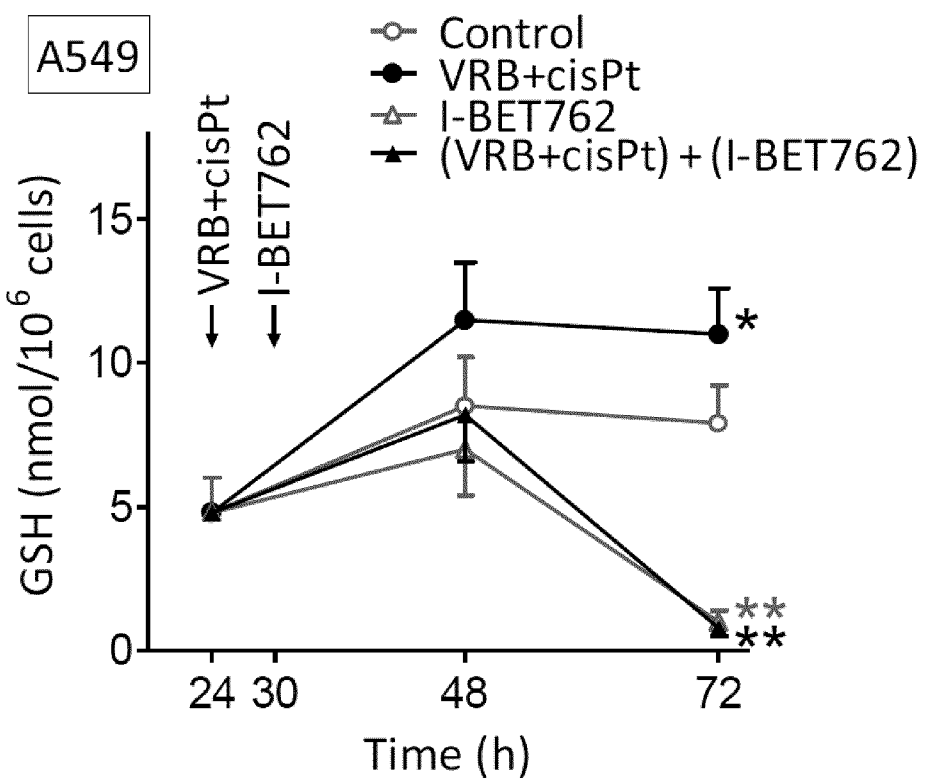
Figure 20:
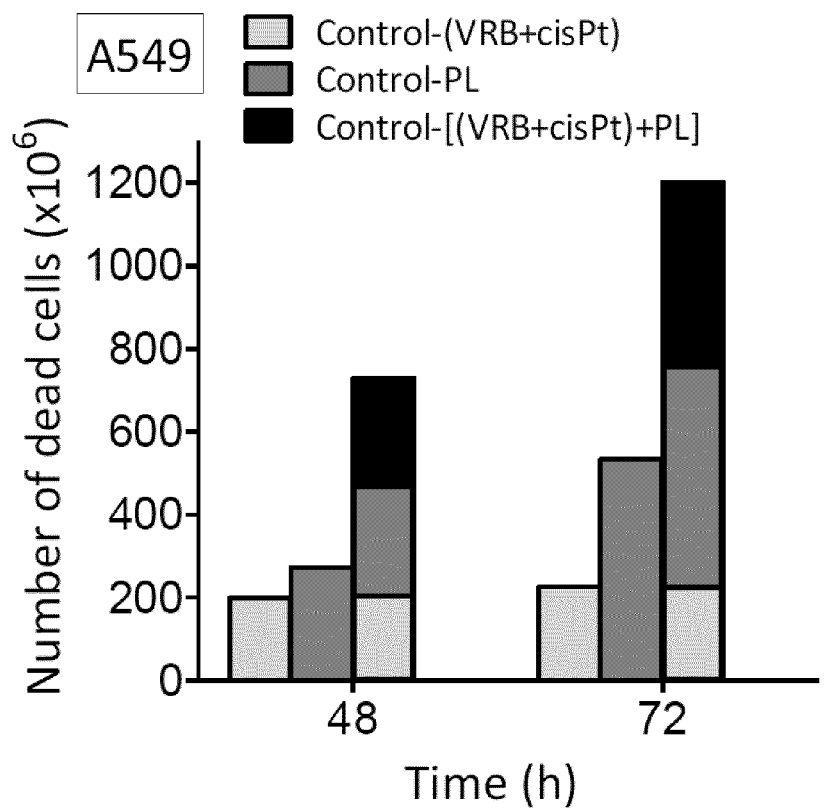
Figure 20:
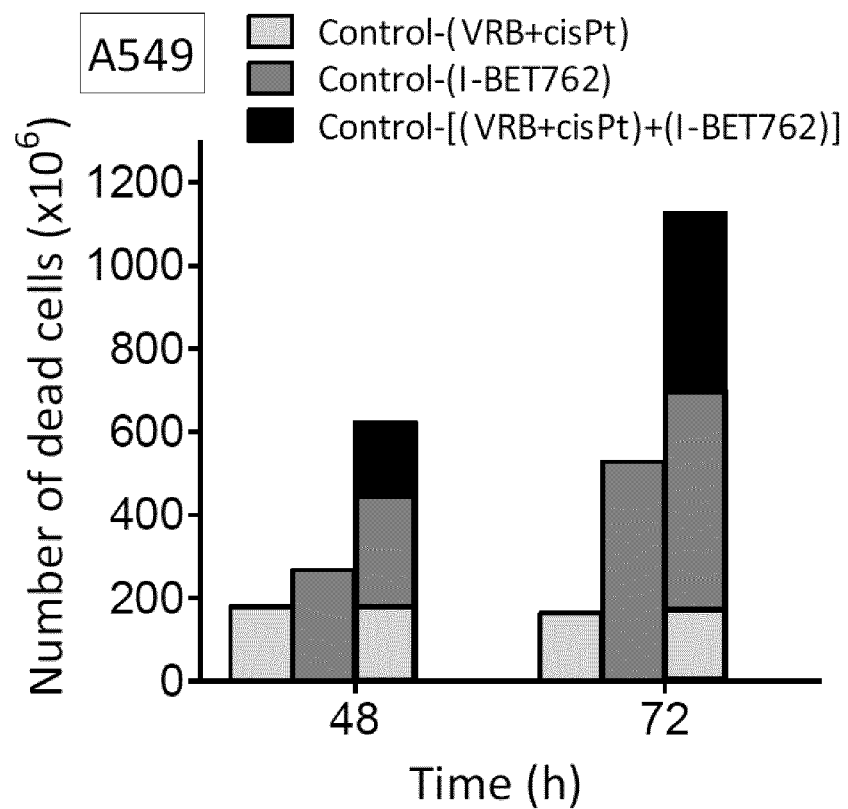
Figure 21:
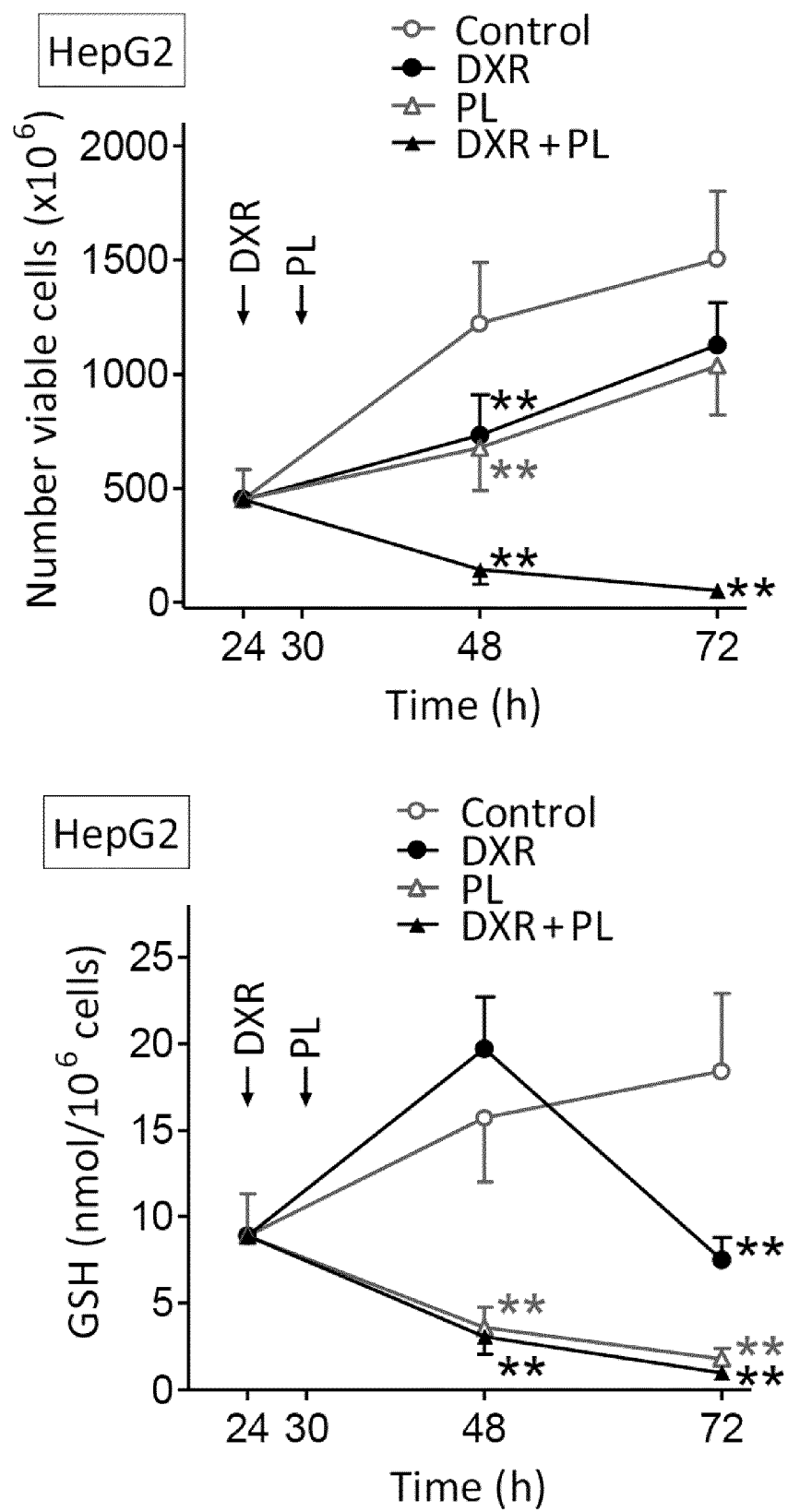
Figure 21:
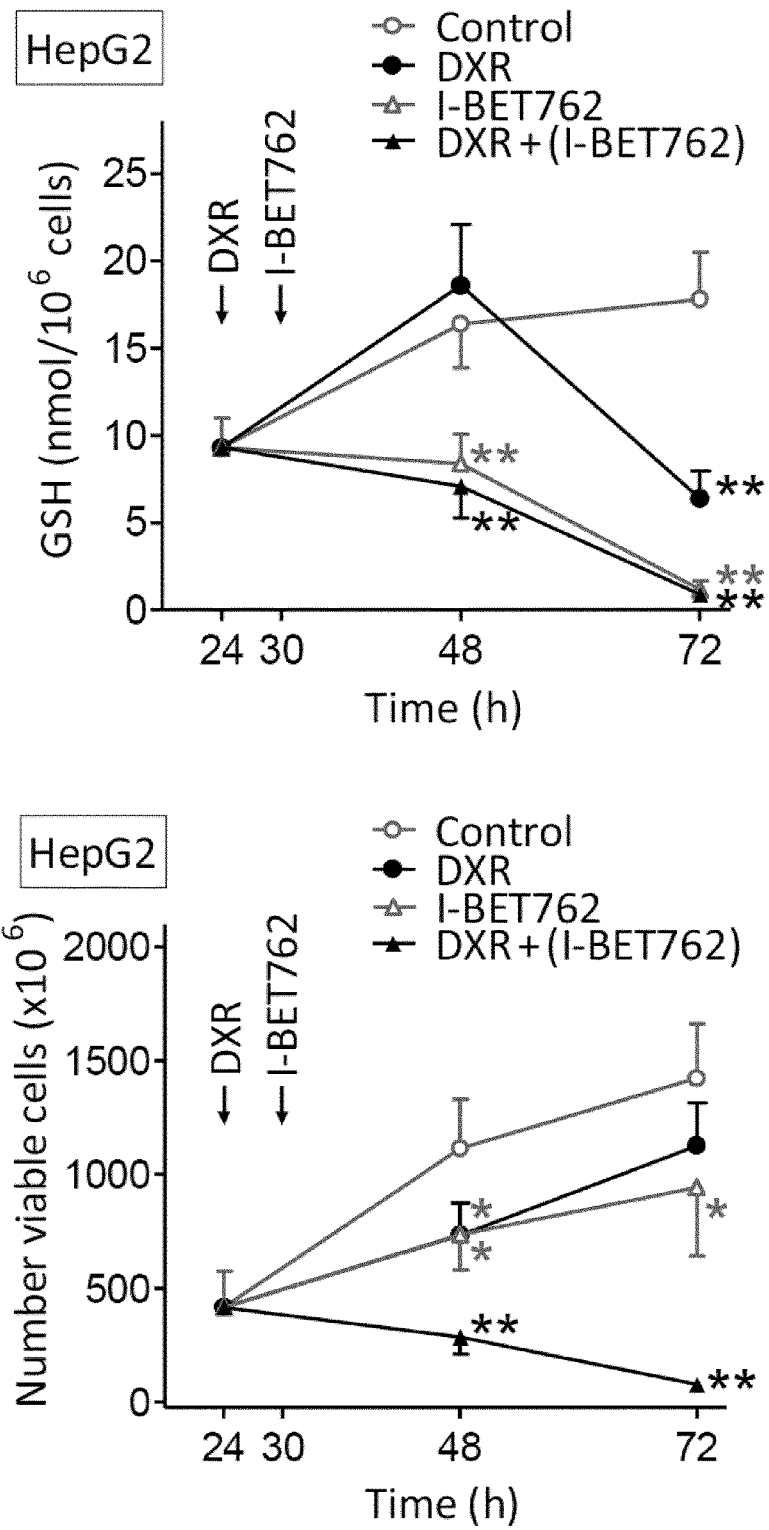
Figure 21:
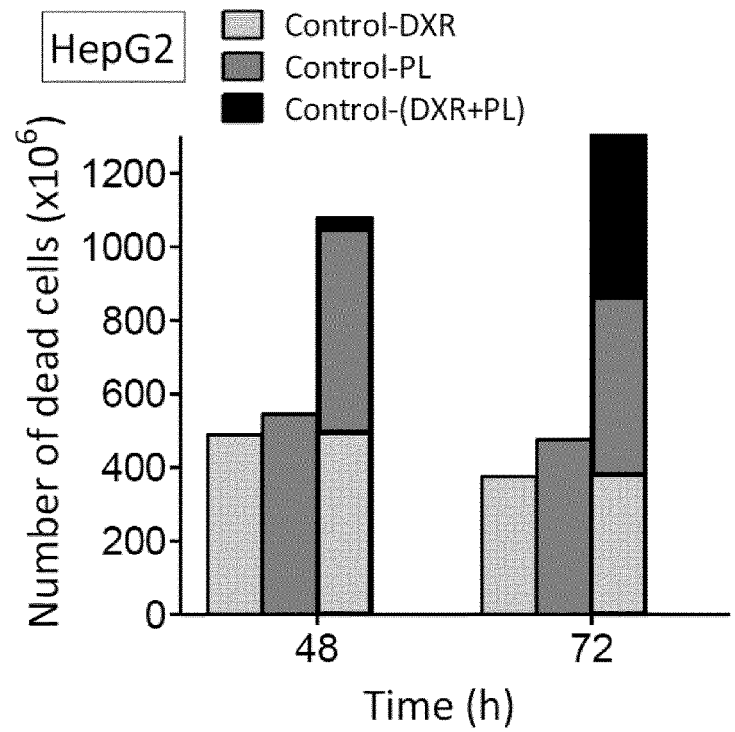
Figure 21:
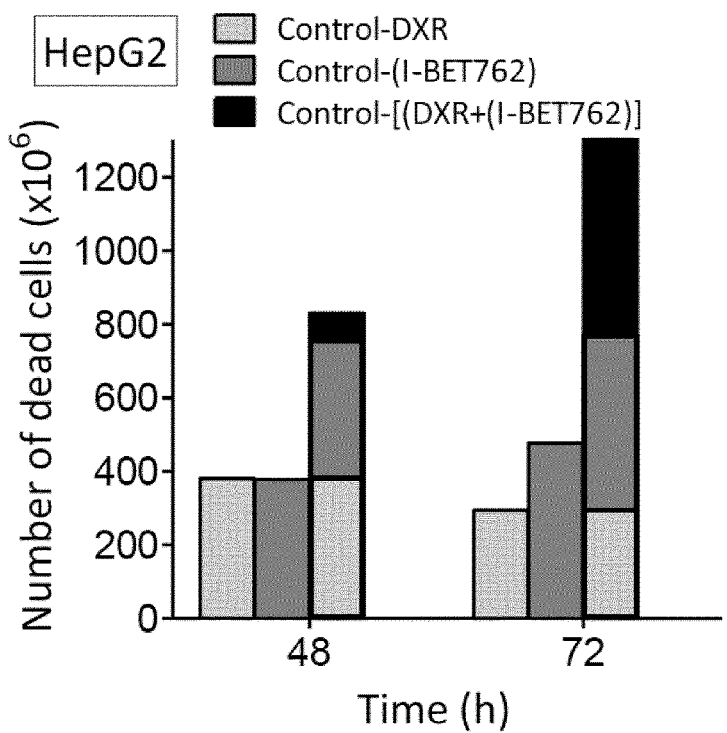
Figure 22:
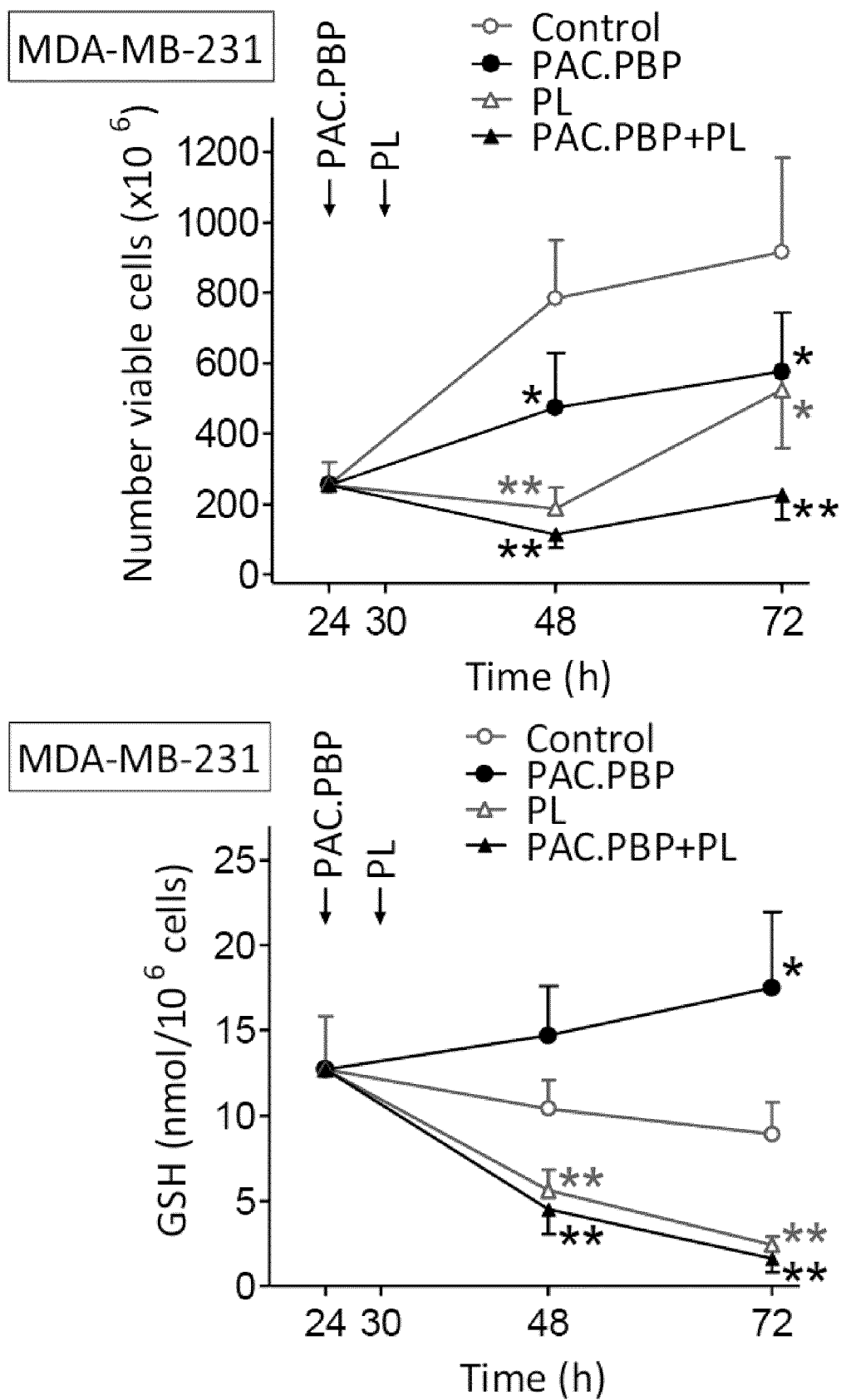
Figure 22:
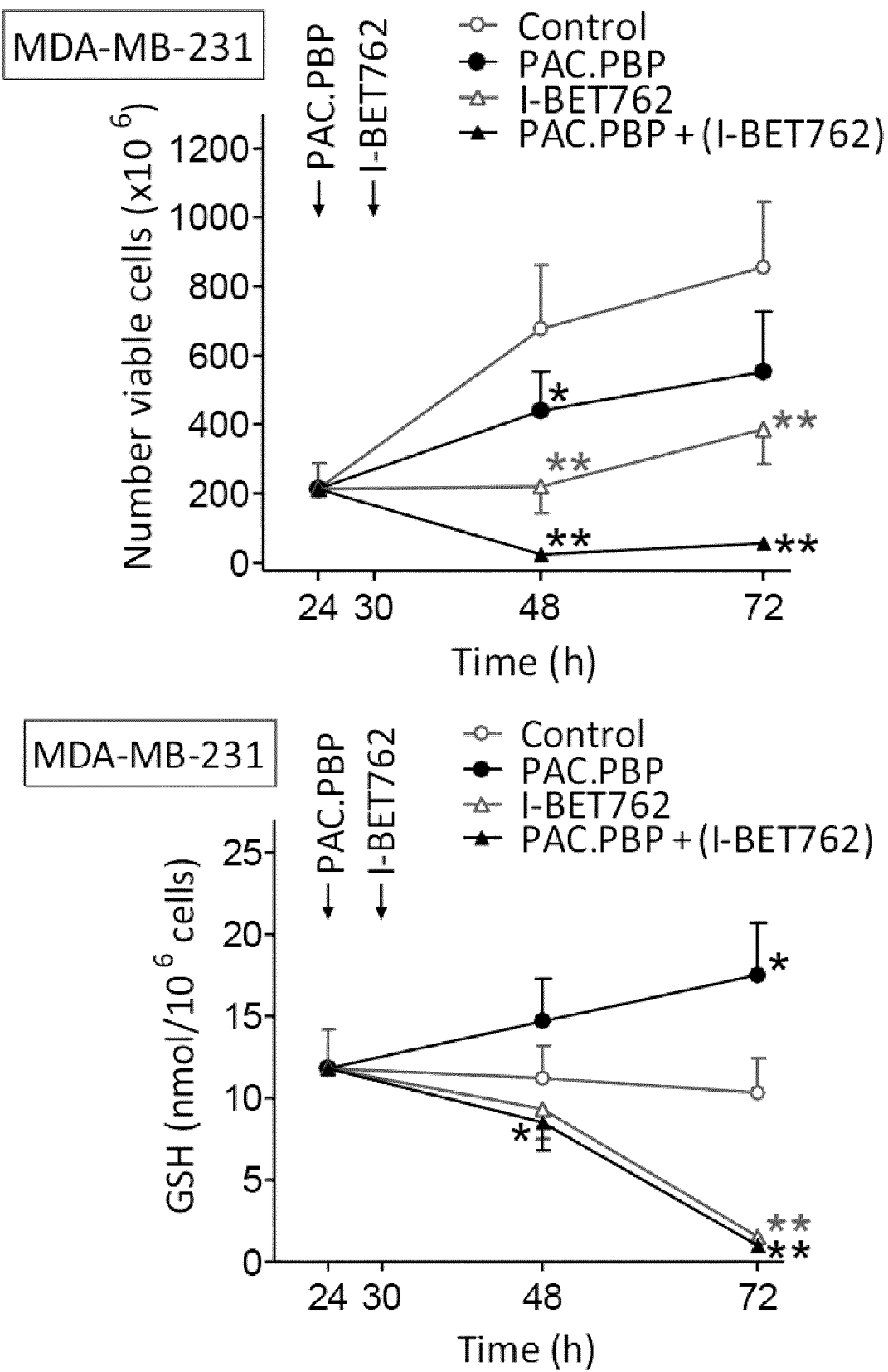
Figure 22:
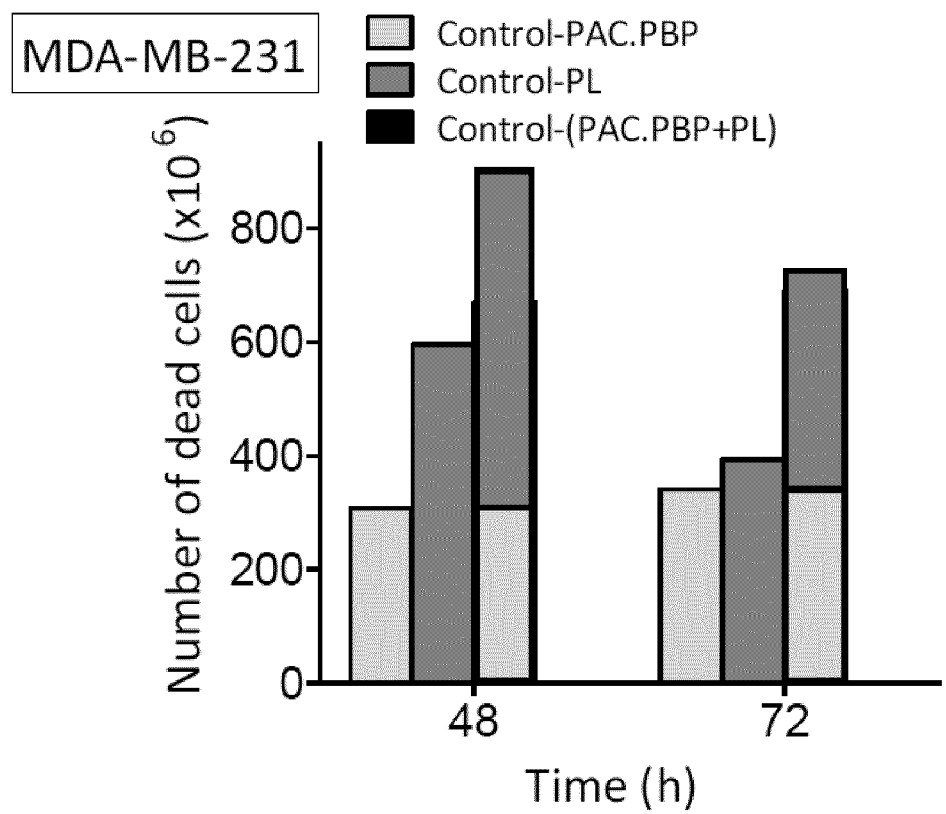
Figure 22:
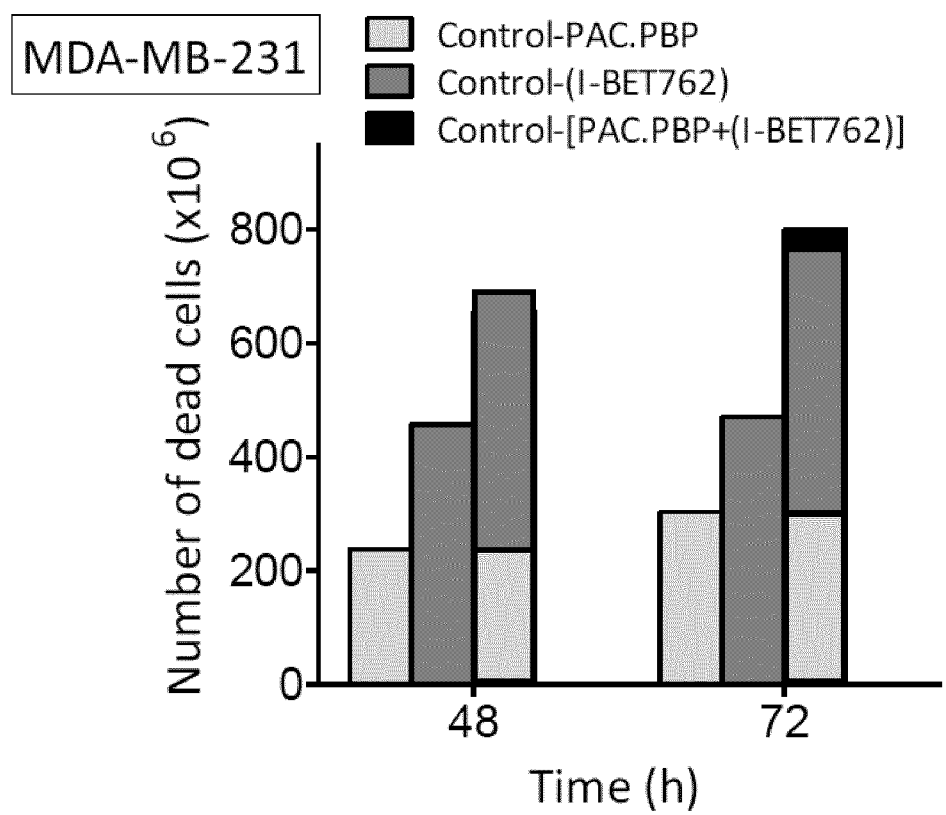
Figure 23:
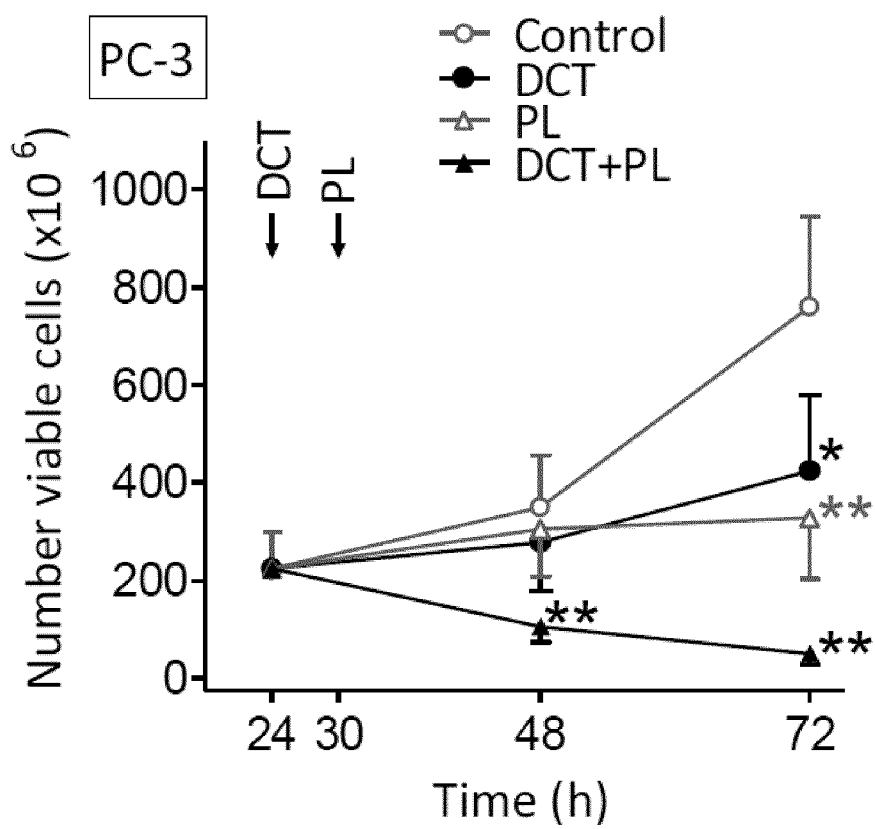
Figure 23:
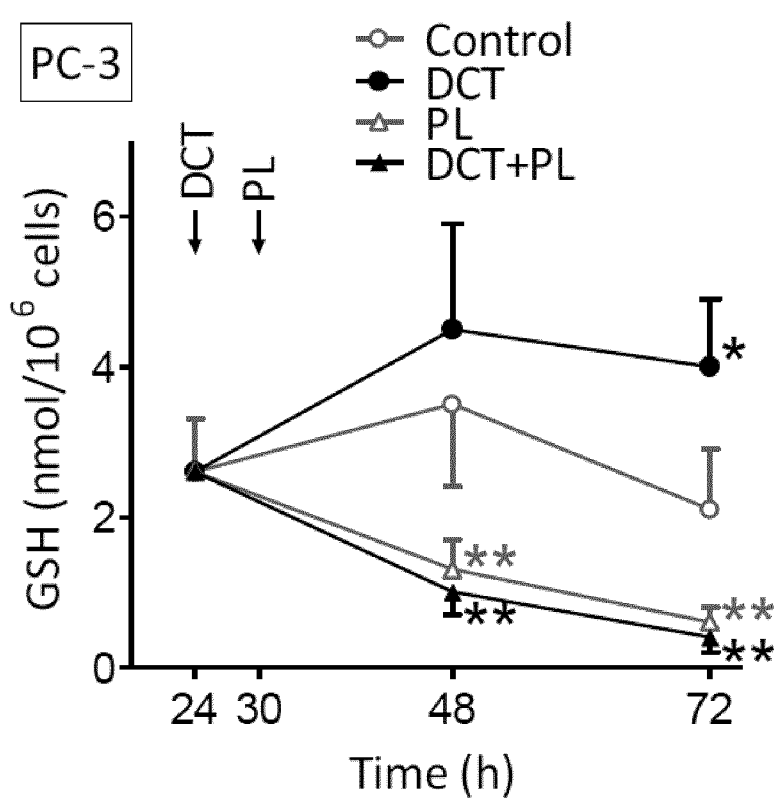
Figure 23:
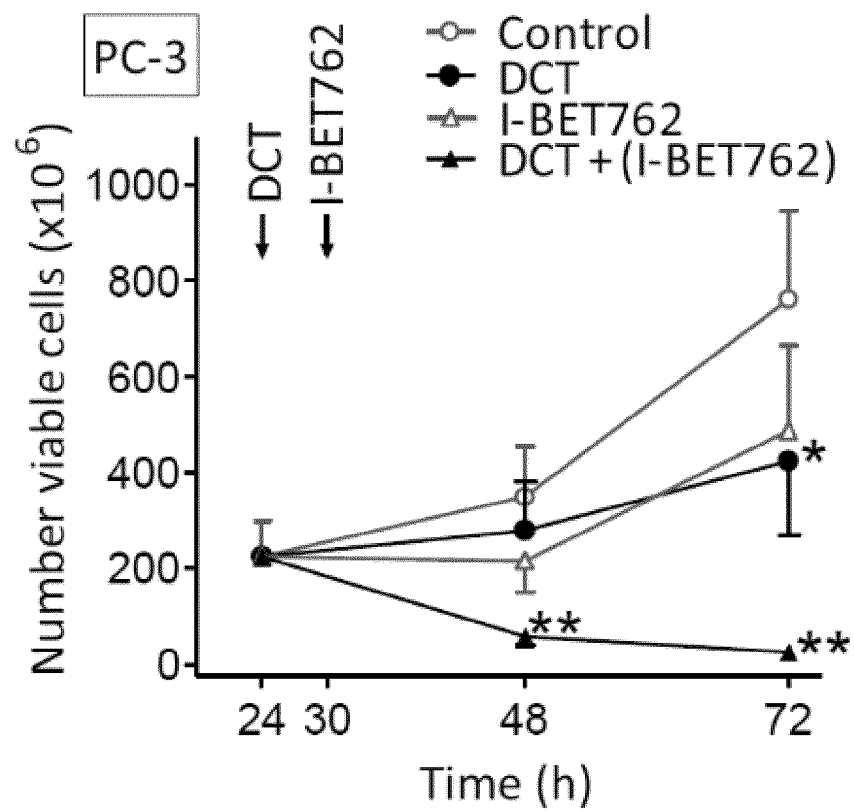
Figure 23:
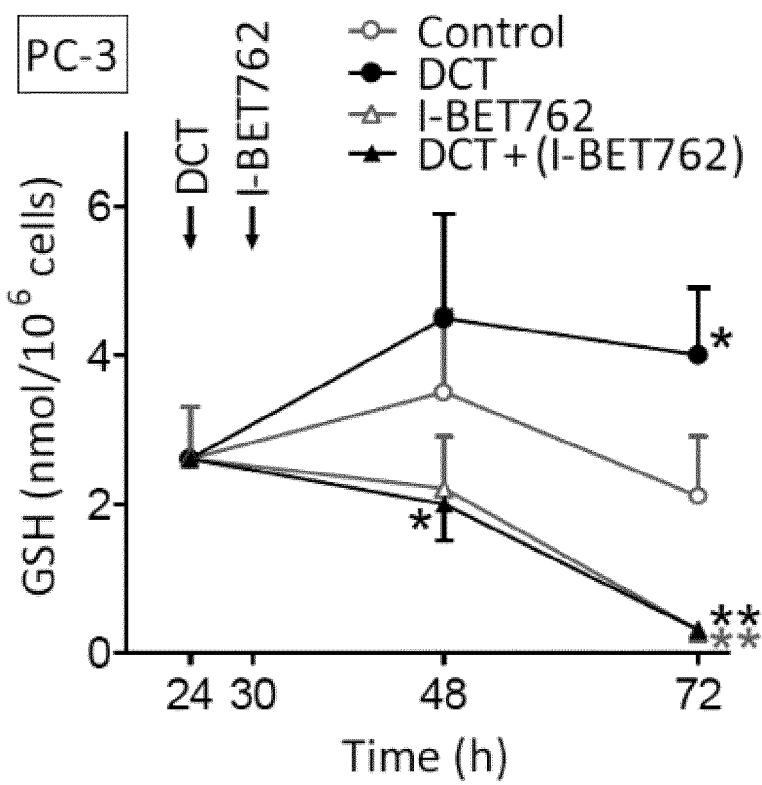
Figure 23:
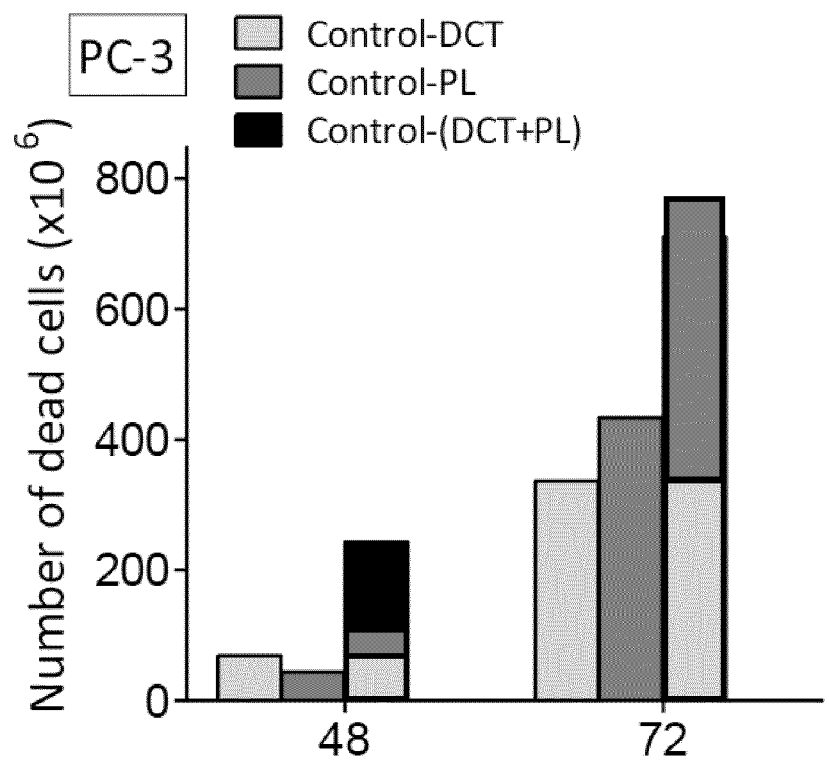
Figure 23:
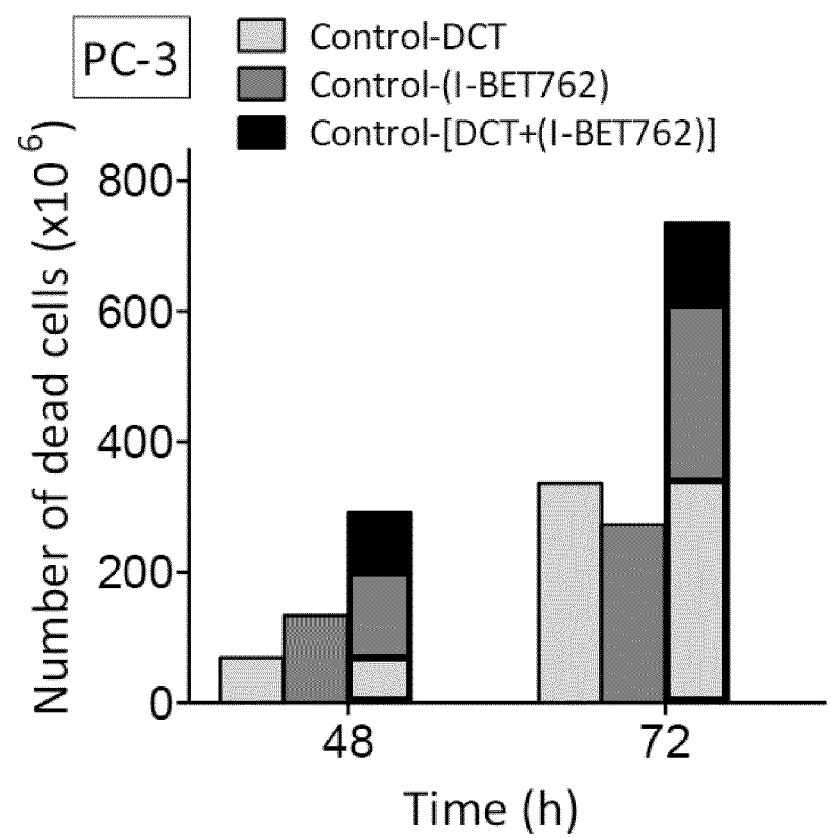
Figure 24:
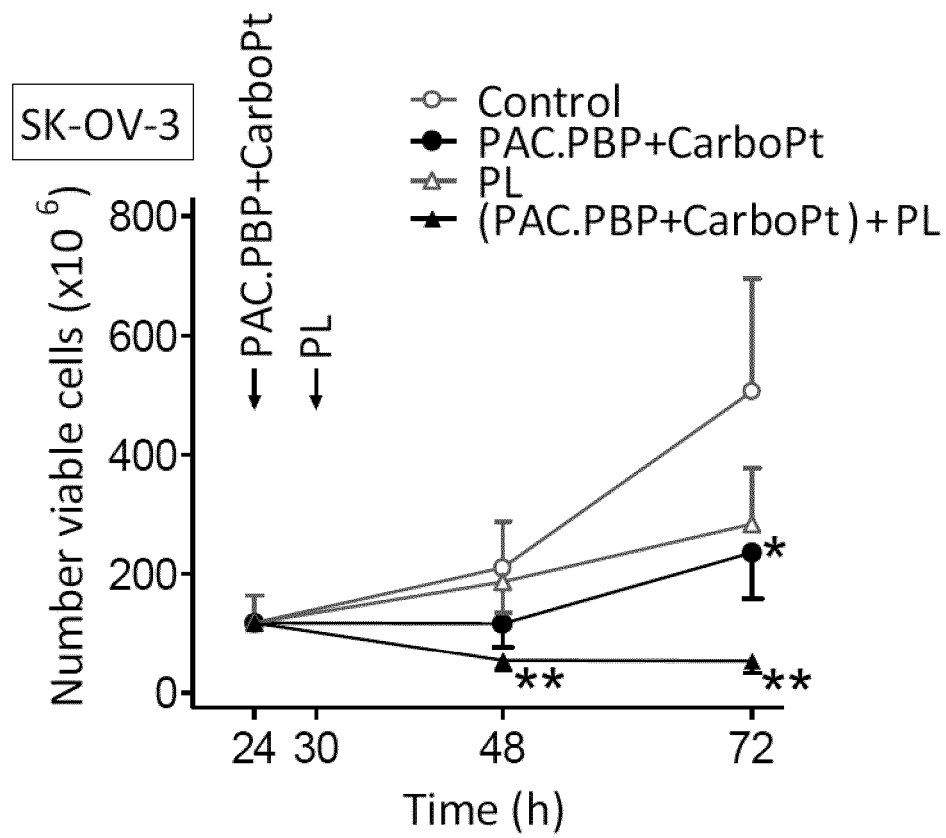
Figure 24:
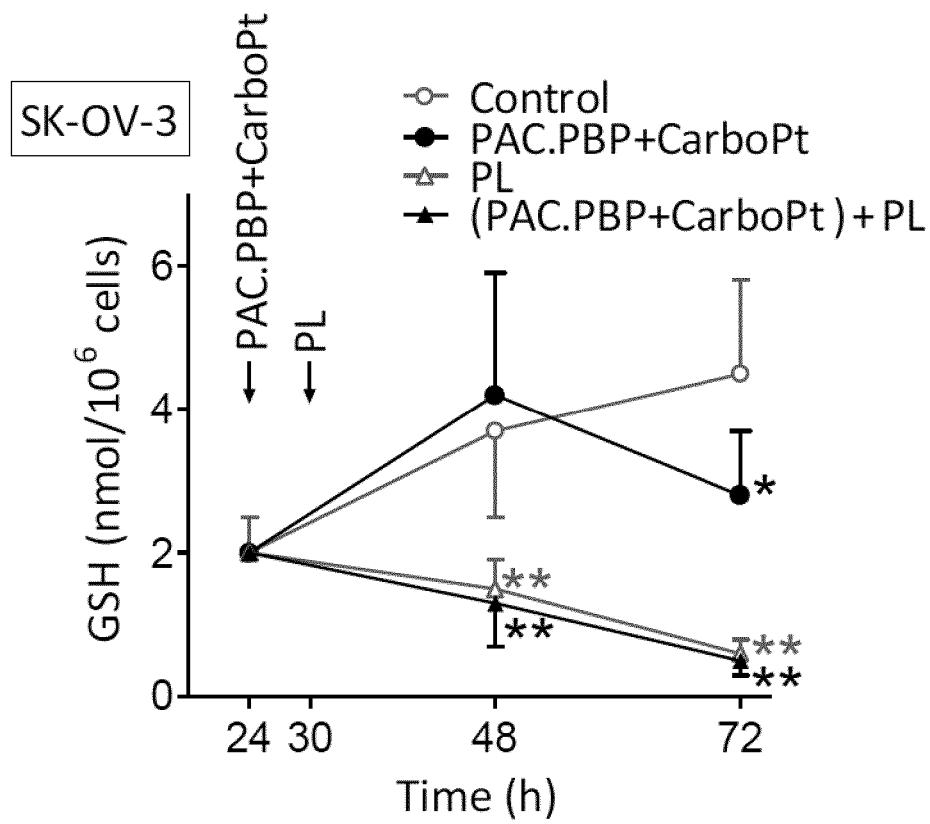
Figure 24:
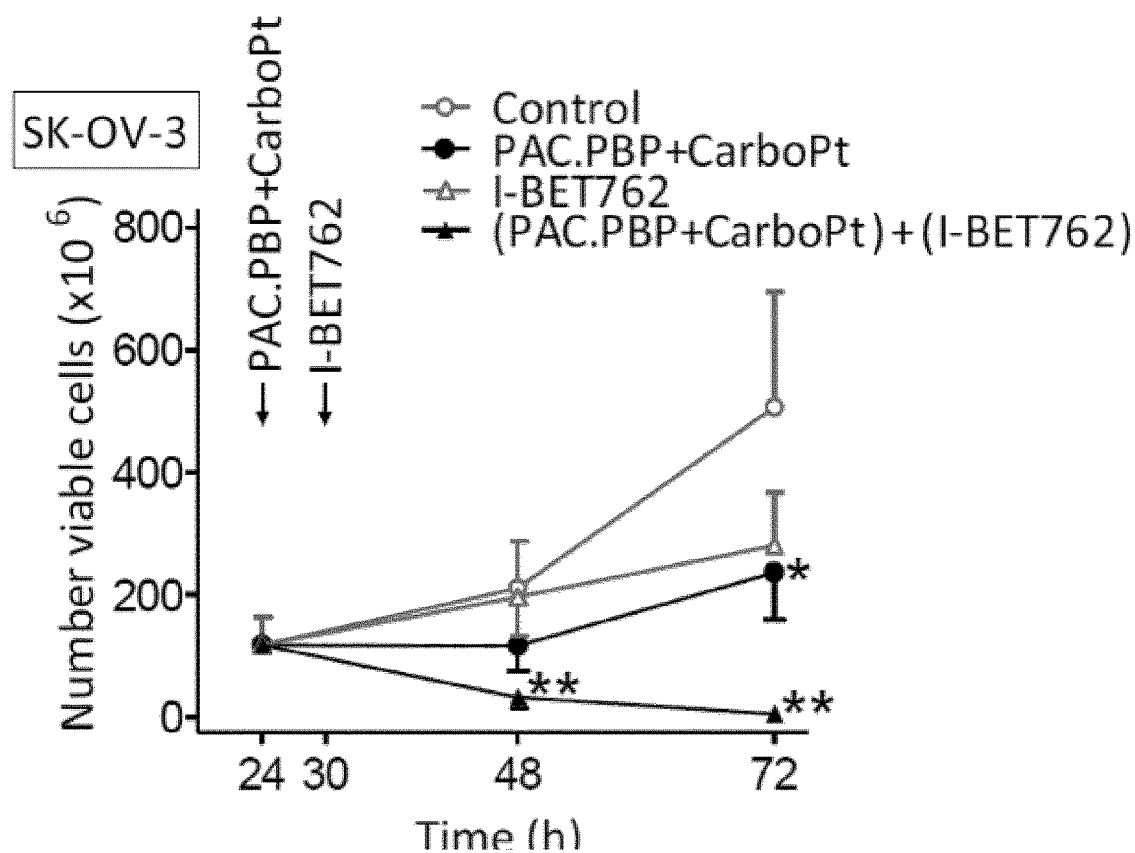
Figure 24:
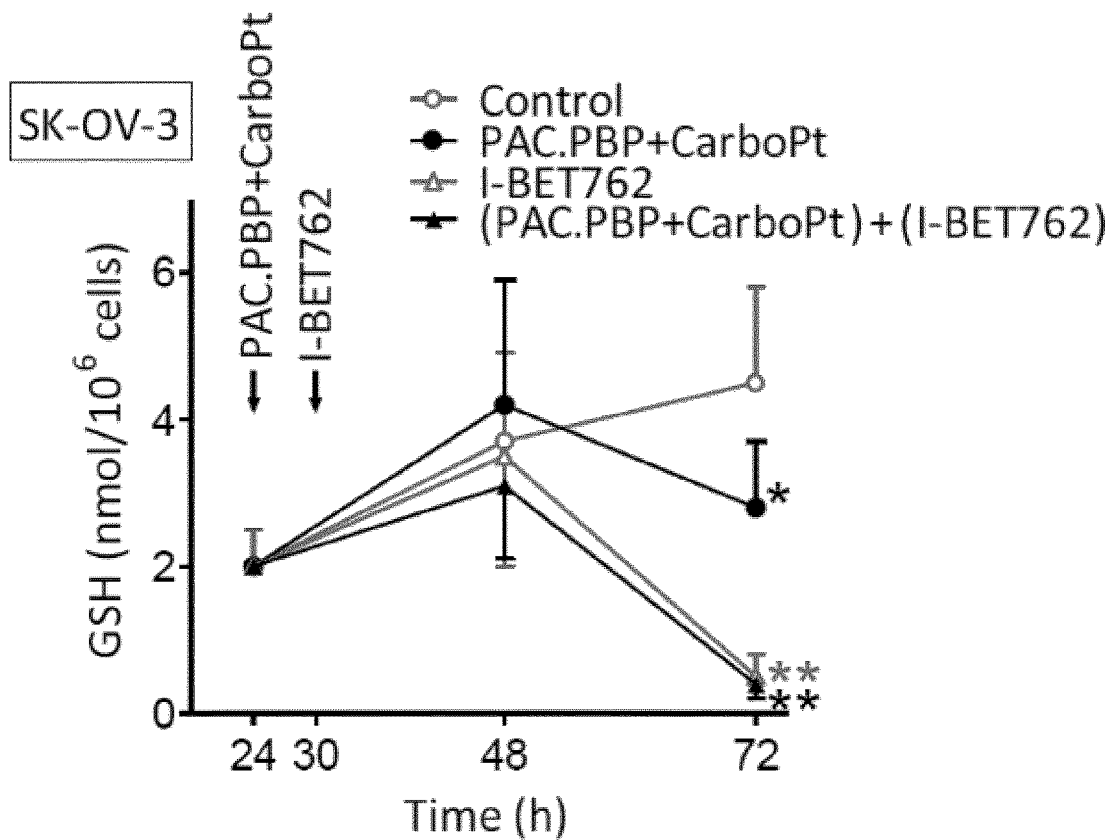
Figure 24:
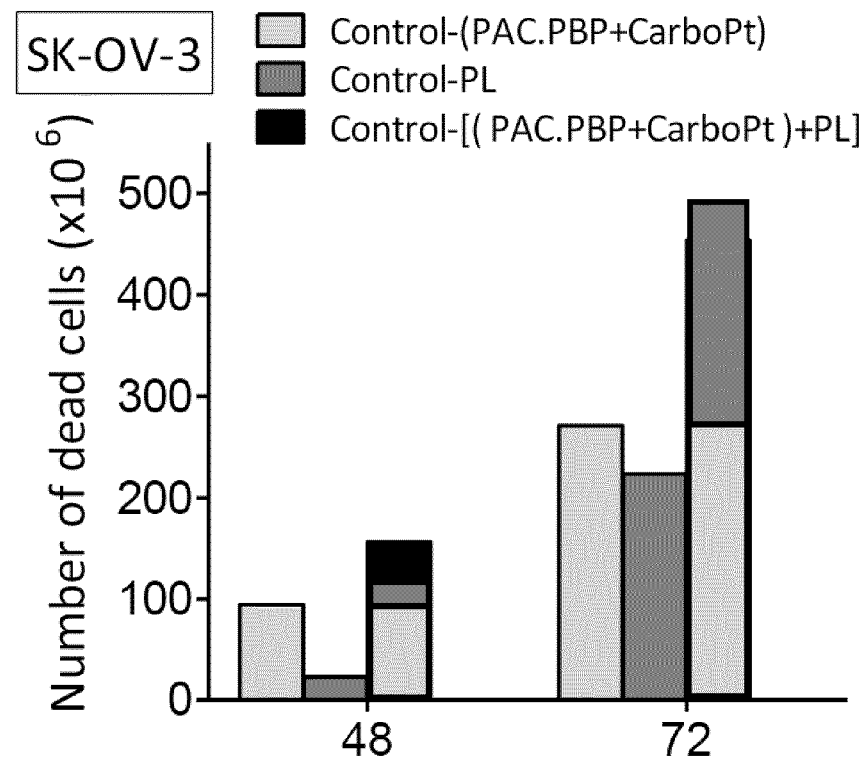
Figure 24:
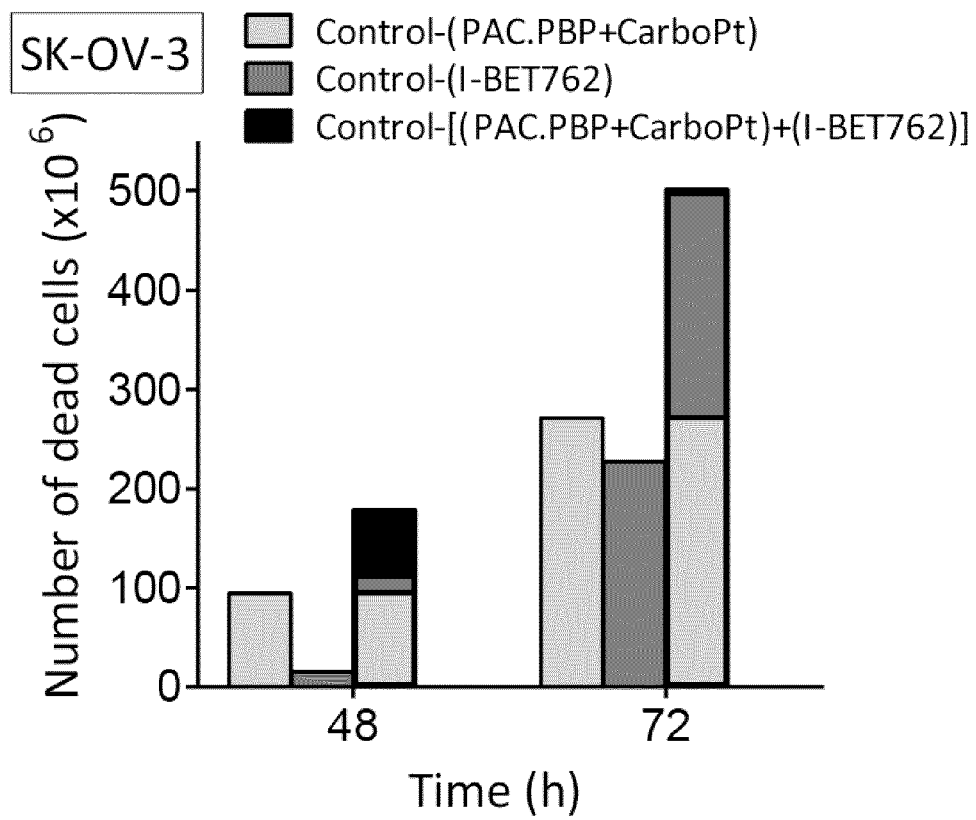
Figure 25:
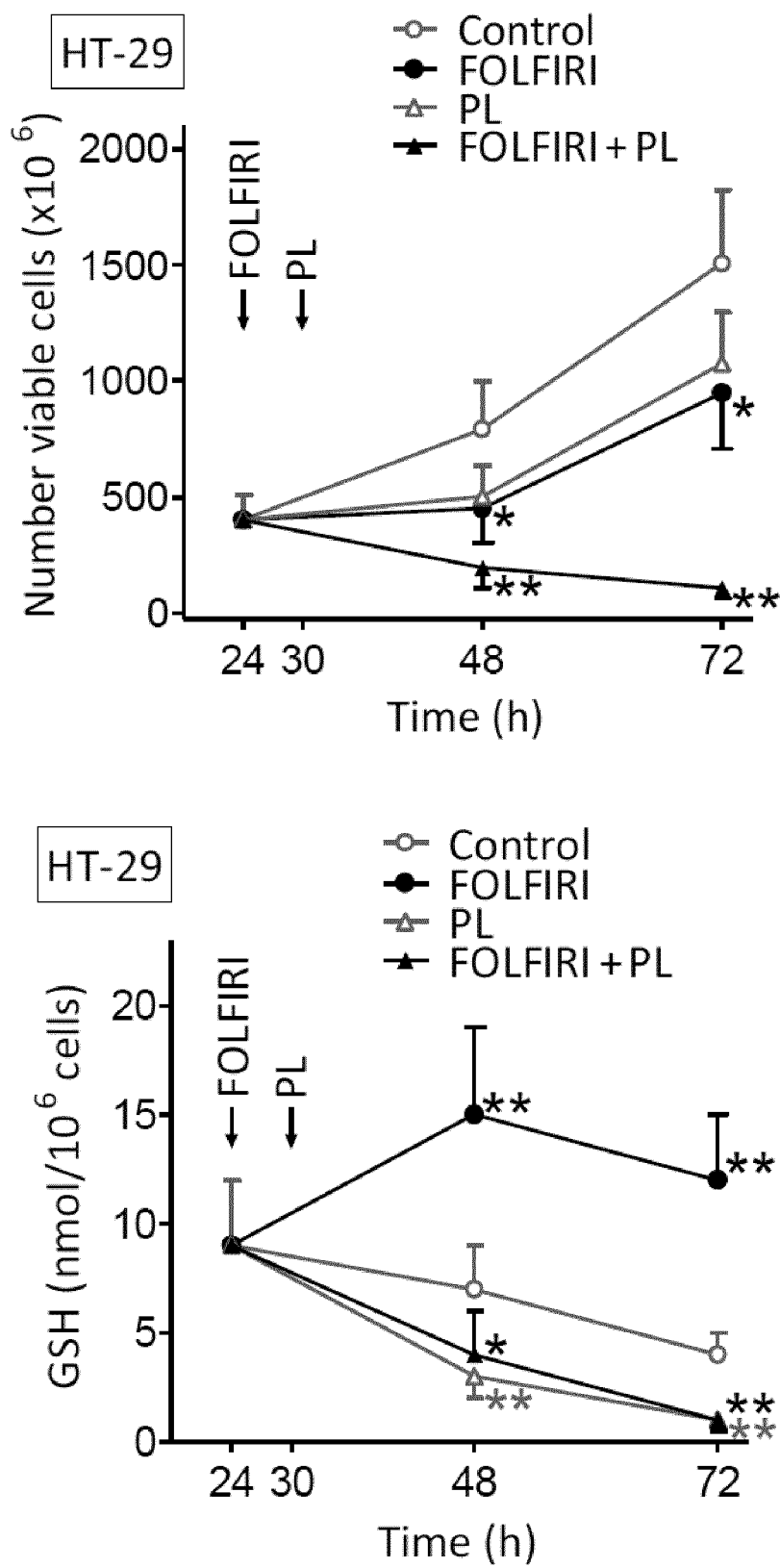
Figure 25:
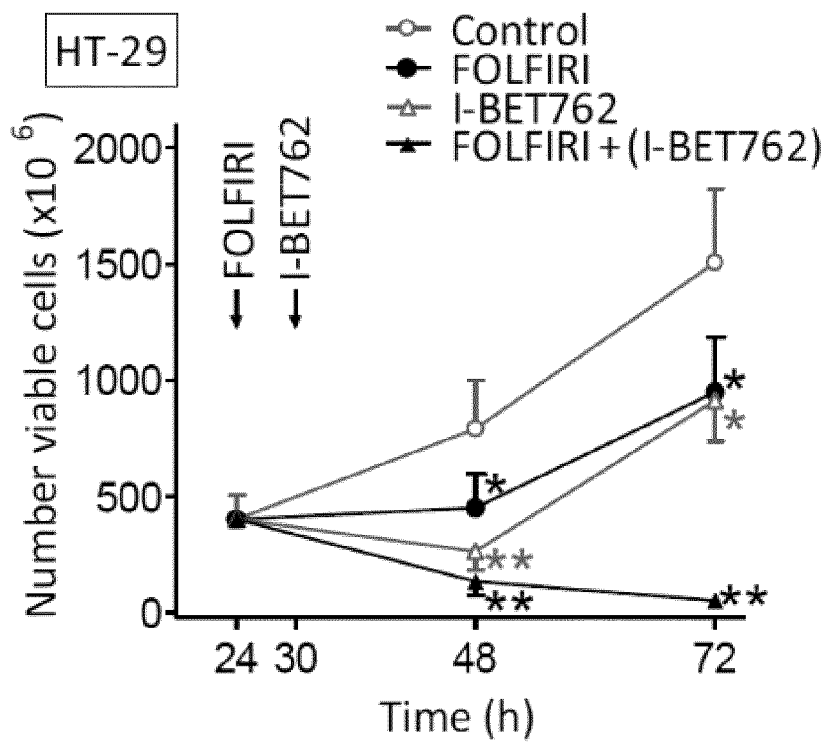
Figure 25:
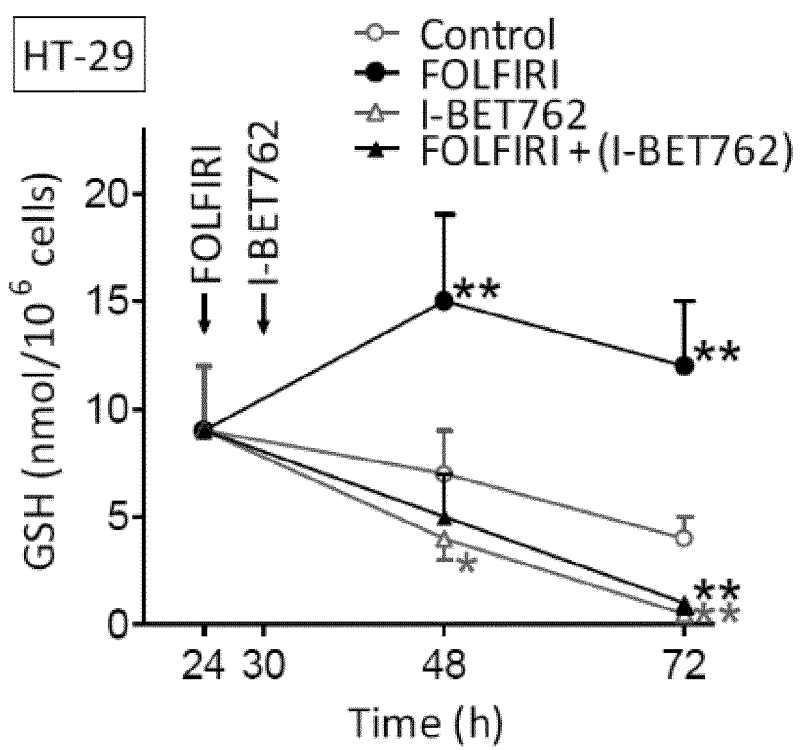
Figure 25:
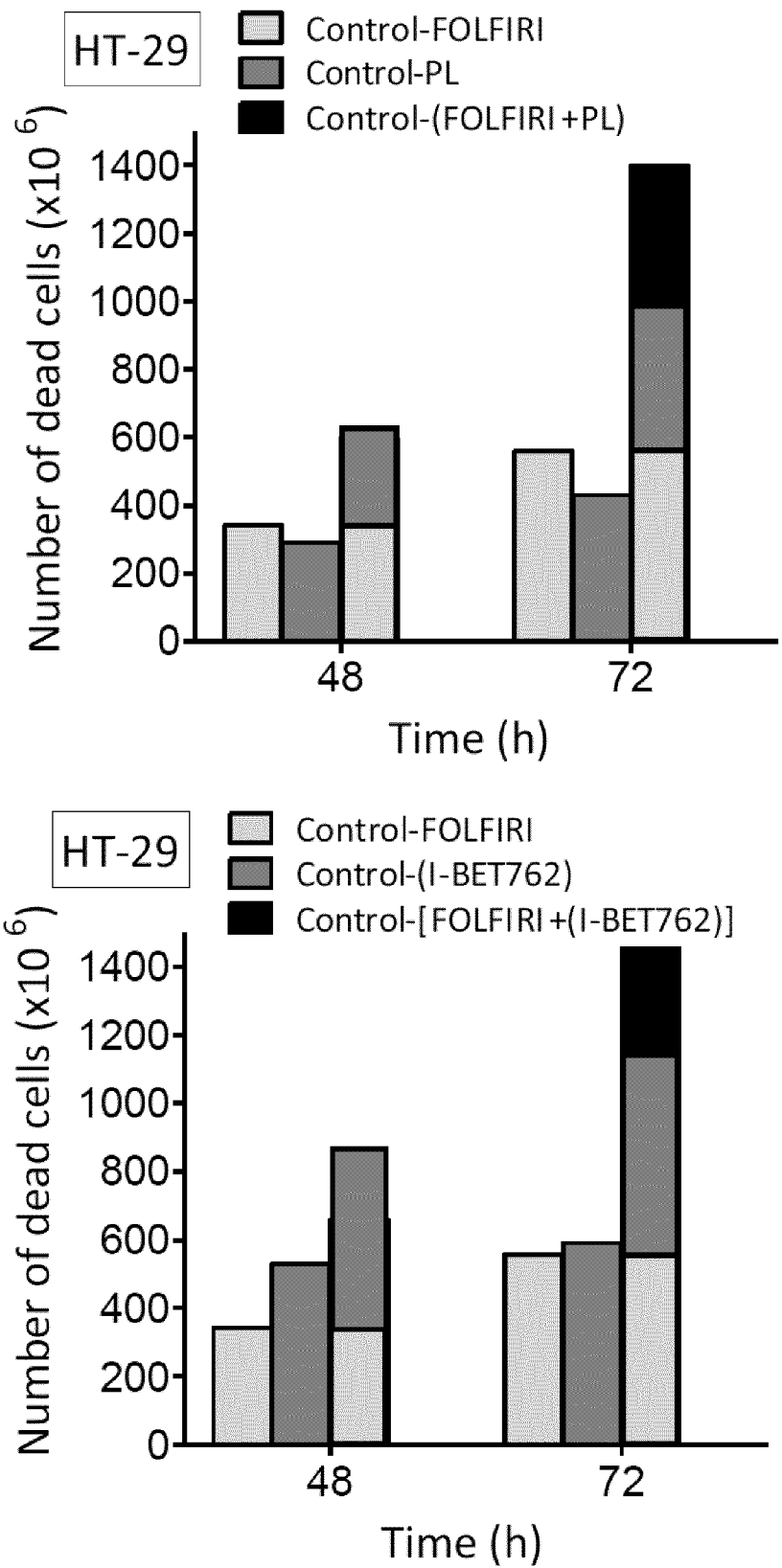

From the all potential GSH depletors, and after running preliminary experiments, two were selected. A) Piplartine (piperlongumine, PL, 5,6-dihydro-1-[(2E)-1-oxo-3-(3,4,5-trimethoxyphenyl)-2-propenyl]-2(1H)-pyridinone), a biologically active alkaloid/amide form Piper species (Piperaceae) which has been shown to have anticancer effects. Interestingly piplartine appears to increases ROS levels and apoptotic cell death in cancer cells but has little effect on either rapidly or slowly dividing primary normal cells. And B) I-BET762, also known as GSK525762A ((S)-2-(6-(4-chlorophenyl)-8-methoxy-1-methyl-4H-benzo [f][1,2,4]triazolo [4,3 a][1,4]diazepin-4-yl)-N-ethylacetamide), a small molecule inhibitor of the BET (Bromodomain and Extra-Terminal) family of bromodomain-containing proteins with potential antineoplastic activity. Interestingly strong down-regulation of c-MYC has been described in a large diversity of cancer types using different BET specific inhibitors. Moreover different findings link c-MYC and GSH synthesis regulation, e.g. c-Myc transcriptionally regulates GCL expression through the ERK/c-Myc phosphorylation pathway (15), and c-Myc is also a Nrf2-interacting protein (16). Consequently, it has been observed that endogenous expression of oncogenic c-Myc lowers the level of cellular ROS. Two different oncogenes, K-Ras and c-Myc, can constitutively increase the transcription of Nrf2 to elevate the basal activity of the antioxidant and cellular detoxification program. In in vitro efficacy assays the concentrations used of PL and I-BET762 were based on pharmacokinetics studies run in our lab (PL, nu/nu mice) (FIG. 17). We run concentration course experiments and the concentration of PL or I-BET762 used in each cancer was the minimum concentration that caused a significant reduction of cancer growth as compared to controls (see FIGS. 18-25). Since the expected in vivo effect of a concentration-dependent drug can be approached using the ratio AUC/MIC (AUC, area under the curve; MIC, minimum inhibitory concentration), under in vitro conditions, we used concentrations that are below (or do not exceed) the limit set by that ratio. The chemotherapy (based on drugs currently used in patients) was selected, for each cancer cell type, after preliminary screening tests. In vitro concentrations used for each chemotherapy drug were based on standard human doses (used for each specific cancer) and drug pharmacokinetics in cancer patients (www.cancer.gov).

As shown in FIGS. 18-25 the number of viable cancer cells, isolated from Pter-treated mice, was drastically reduced by the combination of selected chemotherapy and PL or I-BET762. Additionally, these figures show a clear synergy between the glutathione depleting agent and the chemotherapeutic agent as compared to the effect of each of these compounds alone.

TABLE 7

Effect of anti-melanoma chemotherapy on viability (IC50) of in vitro growing A2058, MeWo and MelJuso Melanoma cell lines

| | IC50 (µM) | | |
|---|---|---|---|
| | A2058 | MeWo | MelJuso |
| Paclitaxel | 0.35 ± 0.10 | 11.12 ± 2.15 | 0.13 ± 0.03 |
| Paclitaxel.PBP | 0.23 ± 0.05 | 7.45 ± 1.40 | 0.07 ± 0.02 |
| Cisplatin | >100 | 44.32 ± 5.43 | 11.23 ± 1.77 |
| Dacarbazine | >100 | >100 | 56.74 ± 7.46 |
| Vinblastine | 7.65 ± 1.35 | 14.50 ± 2.17 | 0.19 ± 0.04 |
| Vincristine | 6.19 ± 2.06 | 12.45 ± 3.04 | 0.15 ± 0.02 |
| Valproic acid | >100 | >100 | 66.17 ± 6.39 |
| BCNU | >100 | >100 | 0.17 ± 0.06 |
| Methotrexate | >100 | >100 | 1.35 ± 0.34 |
| Arsenate | >100 | 94.36 ± 12.41 | 65.45 ± 5.19 |
| Temozolomide | >100 | >100 | >100 |
| Daunorubicin | 2.40 ± 0.73 | 2.61 ± 0.51 | 1.44 ± 0.35 |

The drugs were selected from those recommended by the NCI (www.cancer.gov) for the treatment of melanoma at different steps of in vivo progression. Data are mean values ± SD from 5-6 different experiments per cell line.

TABLE 8

Plasma levels of corticosterone and ACTH, and GR number in cancer cells in pancreatic cancer-bearing mice treated with Pter and/or corticosterone (CRC)

| | AsPC-1 | | | | BxPC-3 | | | |
|---|---|---|---|---|---|---|---|---|
| Treatment | Tumor vol. (mm$^3$) | 10$^3$ GR/cell | CRC (ng/mL plasma) | ACTH (pg/mL plasma) | Tumor vol. (mm$^3$) | 10$^3$ GR/cell | CRC (ng/mL plasma) | ACTH (pg/mL plasma) |
| None | 1217 ± 214 | 72 ± 15 | 356 ± 51 | 280 ± 57 | 690 ± 177 | 126 ± 44 | 192 ± 44 | 195 ± 29 |
| Pter | 523 ± 168* | 63 ± 10 | 217 ± 33* | 112 ± 31* | 226 ± 63* | 115 ± 27 | 88 ± 21* | 68 ± 11* |
| CRC | 1066 ± 235 | 67 ± 7 | 324 ± 48 | 106 ± 17* | 588 ± 158 | 134 ± 36 | 177 ± 36 | 55 ± 12* |
| Pter + CRC | 955 ± 196 | 75 ± 12 | 305 ± 64 | 80 ± 8* | 607 ± 163 | 125 ± 31 | 160 ± 29 | 57 ± 7* |

Figure 7:
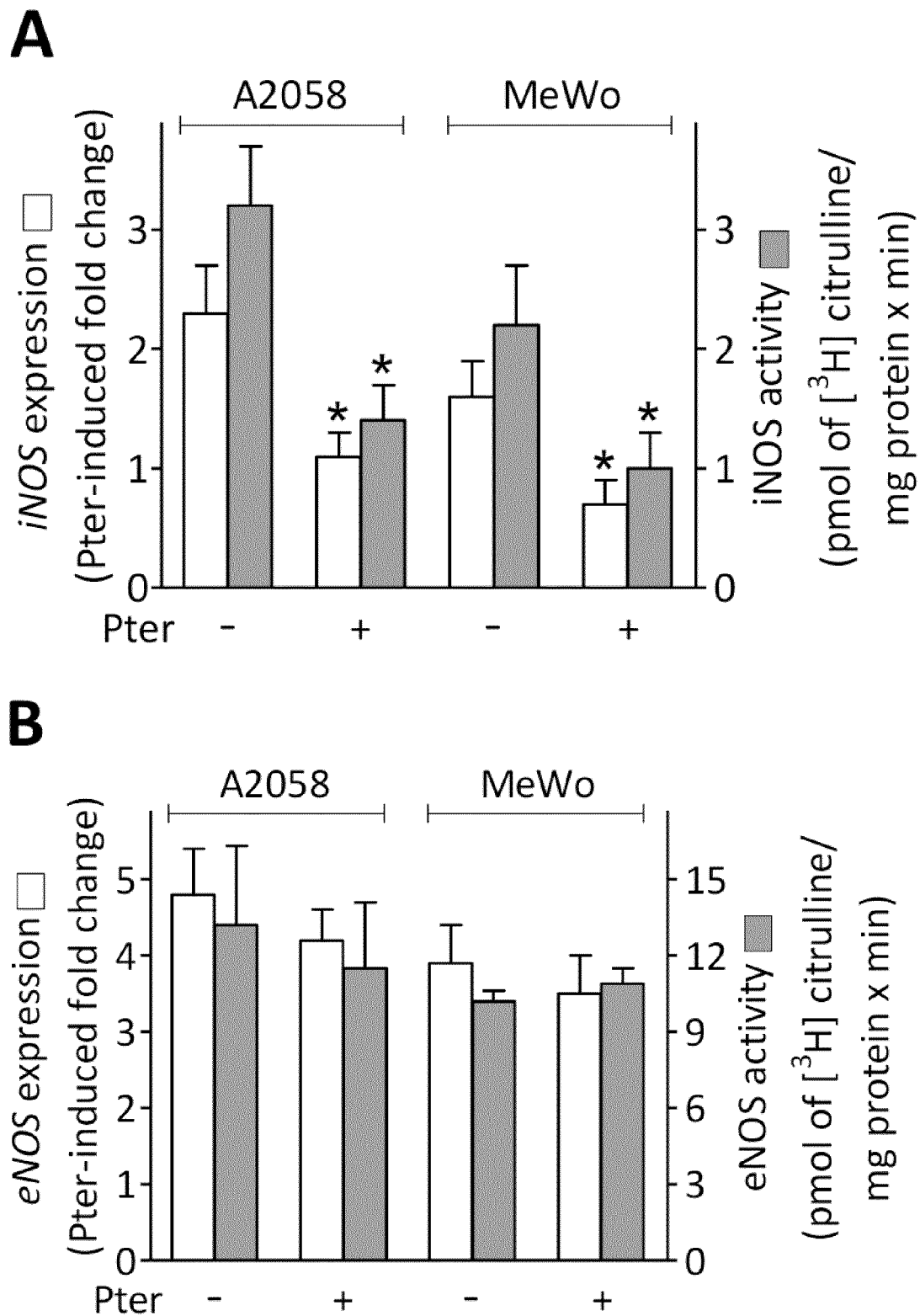
FIG. 7. Expression and activity of iNOS and eNOS in melanoma and endotelial cells, respectively, treated in vivo with Pter. Mice were treated as in FIG. 1A and, thereafter, cells were isolated from the growing tumors as explained under Methods. Total NOS activity is referred as iNOS in tumor cells or eNOS in endothelial cells because it is, in each case, the main activity present in each cell type. Data are expressed as –fold change (gene expression) or picomol of citrulline production (enzyme activity) and are the means±SD of 4-5 different experiments. NO production (NOx=$NO_2^-$ plus $NO_3^-$, see under Methods) in 24-h cultured A2058 melanoma cells isolated from control or Pter-treated mice was of 0.36±0.07 and 0.15±0.04 nmol/$10^6$ cells (n=5; p<0.01), respectively. *Significantly different p<0.01 comparing Pter-treated mice versus controls.
Figure 8:
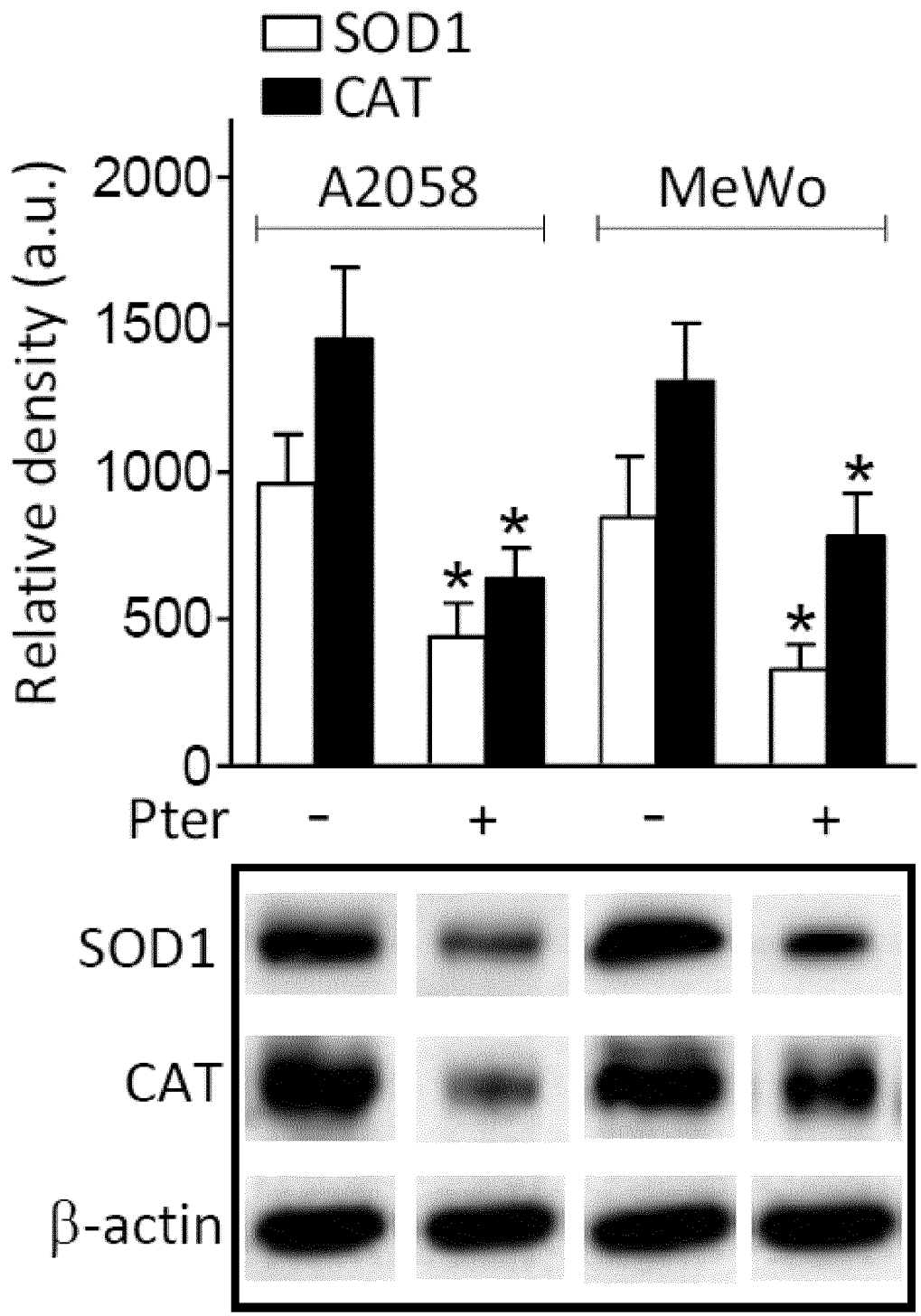
FIG. 8. Effect of Pter treatment on SOD1 and CAT protein levels in human melanoma tumors growing in vivo. Western blot analysis was performed as indicated under Methods. Data are mean values±SD of 4 different animals. *Significantly different p<0.01 comparing controls versus Pter-treated mice.
Figure 9:
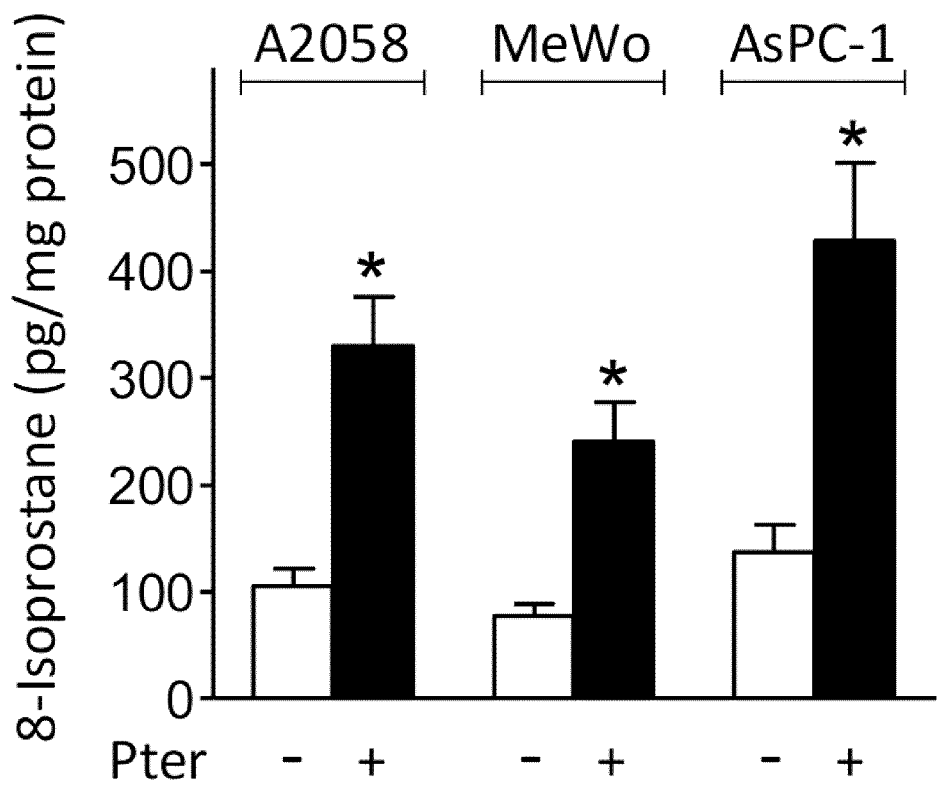
FIG. 9. Effect of Pter treatment on lipid peroxidation in human melanoma and pancreatic cancer tumors growing in vivo. 8-Isoprostane levels were measured to evaluate lipid peroxidation as indicated under Methods. Data are mean values±SD of 5-6 different animals. *Significantly different p<0.01 comparing controls versus Pter-treated mice.
Figure 10:
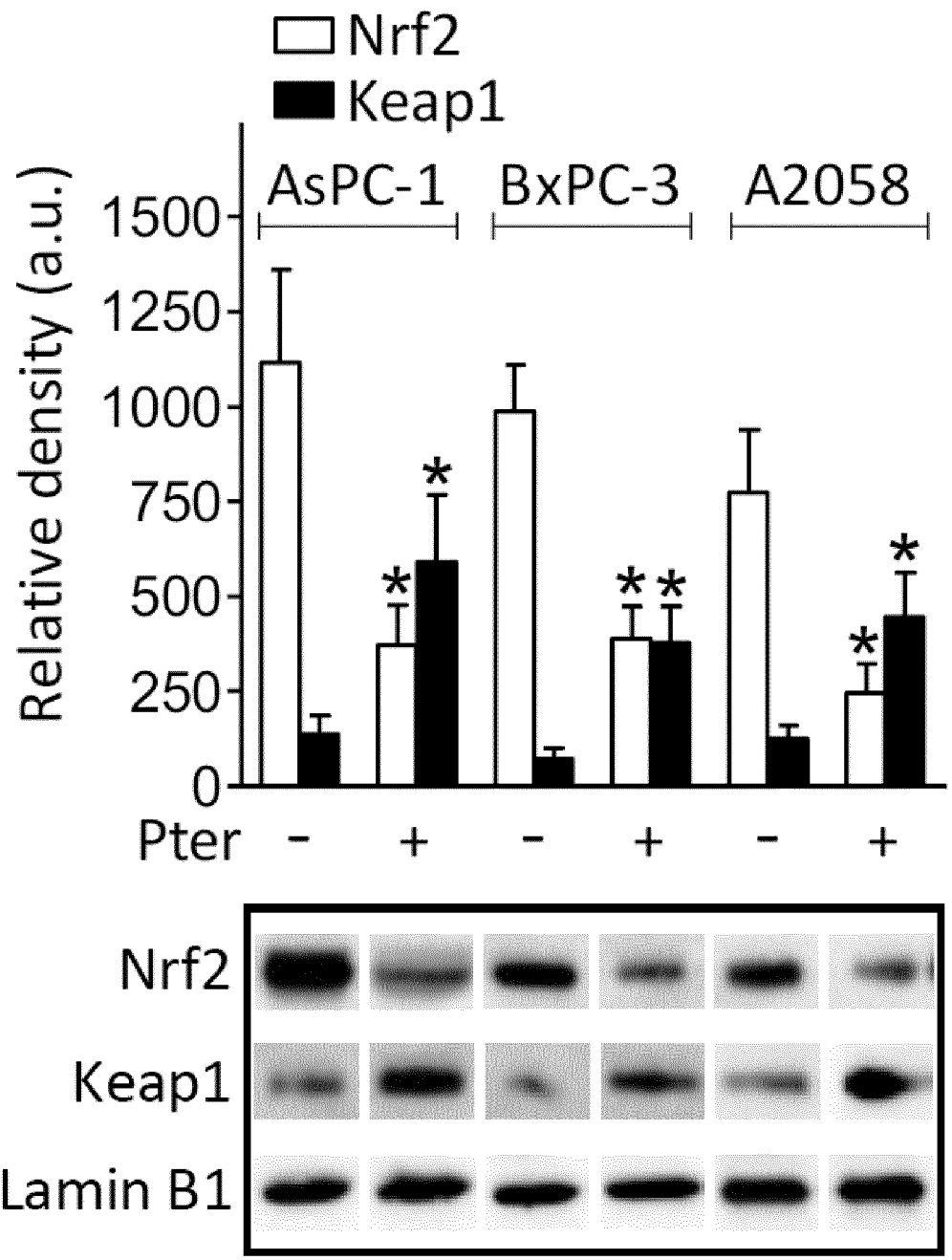
FIG. 10. Effect of Pter treatment on nuclear Nrf2 and cytosolic Keap1 in melanoma-pancreatic cancer-bearing mice. Nuclear accumulation of Nrf2 and cytosolic levels of Keap1 from in vivo growing ASPC-1-RFP, BxPC-3-RFP and A2058 cells were measured by Western blotting (see under Methods). Anti-Keap1 monoclonal antibodies were from Thermo Scientific Inc. (Rockford, Ill.). Data are mean values±SD for 4-5 different experiments, *Significantly different p<0.01 comparing Pter treatment vs controls).
Figure 11:
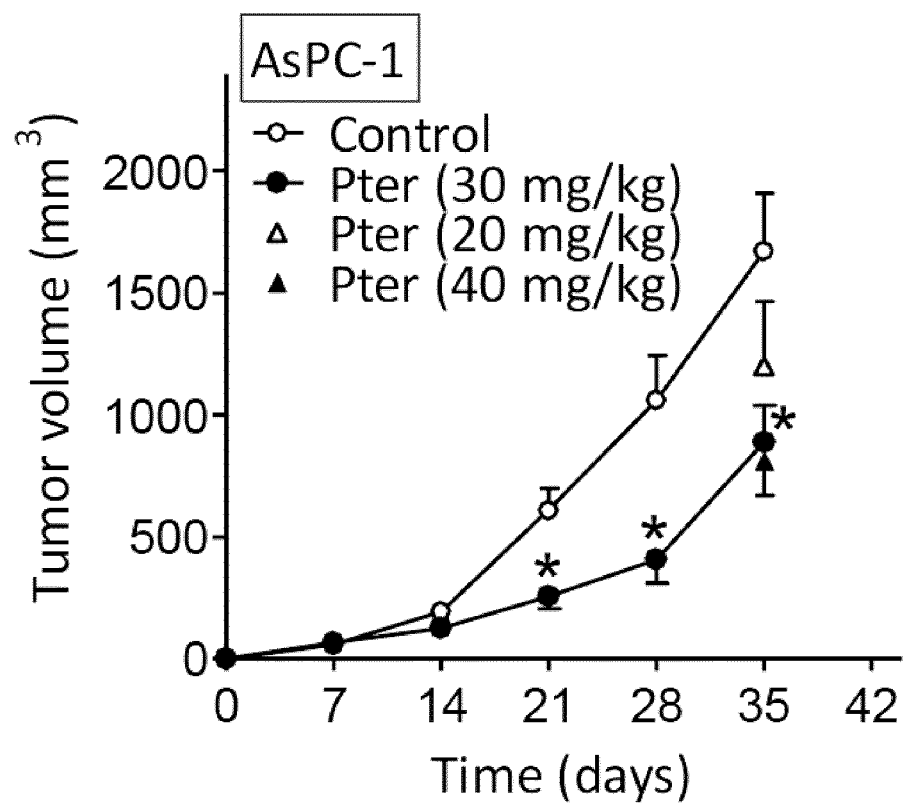
FIG. 11. In vivo effect of Pter on human pancreatic cancer growth. Pter was administered i.v. every 48 h for a period of 4-5 weeks, starting 1 week after tumor inoculation. For the doses of 20 and 40 mg Pter/kg only the point at the end of the treatment period is shown. Plasma vs tumor levels of Pter after its i.v. administration (30 mg/kg) were not significantly different from those calculated for melanoma-bearing mice. Under in vitro conditions 15 μM Pter×60 min every 24 h starting 24 h after seeding (as in FIG. 1C) did not affect ASPC-1 and BxPC-3 cell growth or viability. All data displayed All data are mean values±SD of 6-7 different animals. *Significantly different p<0.01 comparing Pter-treated mice vs controls.
Figure 11:
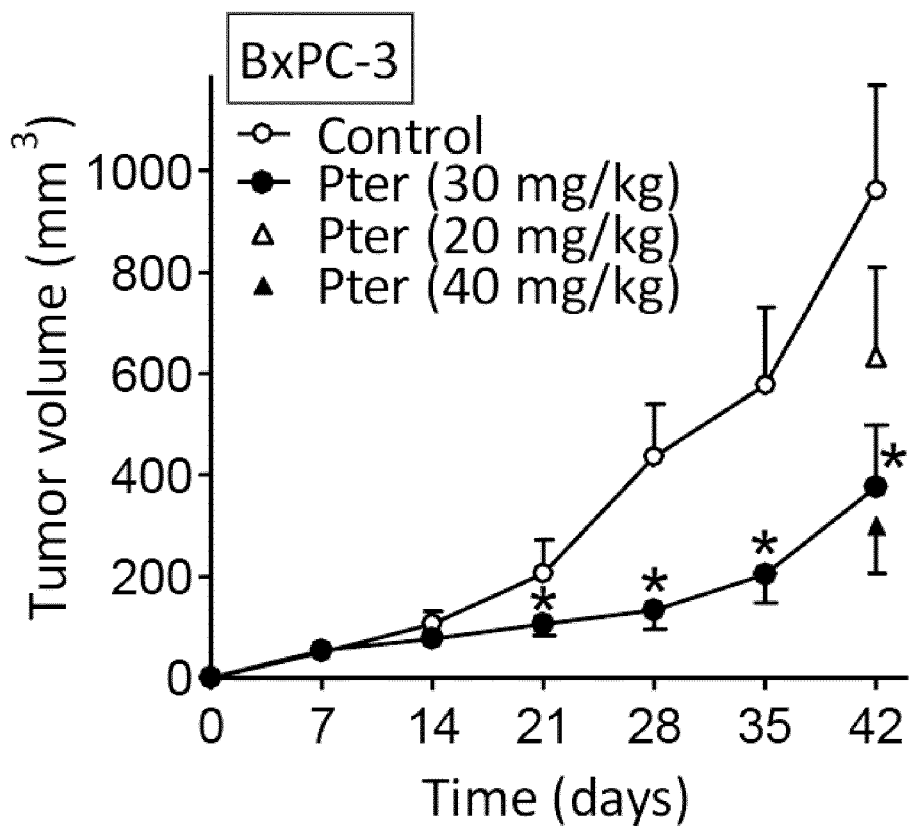

Pancreatic cancer cells stably expressing the red fluorescence protein (RFP) (transfection was performed using the same methodology used for melanoma cells) were inoculated, as in FIG. 7, and allowed to grow for 28 (ASPC-1) or 35 (BxPC-3) days. Treatment with Pter (as in FIG. 7) and/or corticosterone was performed as in Table 4. Treatment of tumor-bearing mice with vehicles (DMSO-ethanol for Pter as indicated under Methods; or polyethylene glycol 400 for corticosterone) did not significantly affect the rate of pancreatic cancer growth as compared to controls (not shown). The number of GR (expressed as binding sites/cell) was not significantly different when 72 h-cultured AsPC-1-RFP and BxPC-3-RFP cells were compared with their wild type AsPC-1 or BxPC-3 cell counterparts (not shown). Data for GR number; tumor volume (Tumor vol.) and corticosterone (blood samples were obtained at 12 h circadian time) displayed in this table were obtained 28 (AsPC-1) or 35 (BxPC-3) days after tumor inoculation. Data for ACTH levels were obtained at 6 h circadian time. All tumors had 50-70 mm$^3$ of volume on day 7 after inoculation. GR number on day 7 was not significantly different from GR number on day 28 or 35 (not shown). Data are mean values ± SD of 5-6 different animals.
*Significantly different p < 0.01 comparing all groups vs controls (untreated). Data obtained in pancreatic cancer-bearing mice treated with vehicle were not significantly different from those calculated for the untreated group (not shown).

TABLE 9

Effect of Pter treatment on different Nrf2- and redox state-related enzyme activities and metabolites in pancreatic cancer cells growing in vivo

|  |  | AsPC-1 | | BxPC-3 | |
|---|---|---|---|---|---|
|  |  | − | +Pter | − | +Pter |
| GSH and TXN | GCL (mU/10$^6$ cells) | 157 ± 32 | 85 ± 27* | 94 ± 24 | 36 ± 15† |
|  | GSS (mU/10$^6$ cells) | 20.2 ± 3.9 | 12.4 ± 2.7† | 8.5 ± 1.8 | 4.0 ± 1.3† |
|  | GPX (mU/10$^6$ cells) | 20.3 ± 4.4 | 15.0 ± 2.6* | 14.7 ± 3.0 | 9.2 ± 2.0* |
|  | GSR (mU/10$^6$ cells) | 8.6 ± 2.4 | 5.5 ± 1.2* | 4.1 ± 1.3 | 2.3 ± 0.7* |
|  | GST (mU/10$^6$ cells) | 12.4 ± 2.9 | 8.0 ± 1.5 | 5.3 ± 1.7 | 3.2 ± 1.0* |
|  | GGT (mU/10$^6$ cells) | 28.9 ± 5.8 | 27.5 ± 7.4 | 20.4 ± 3.4 | 19.7 ± 3.7 |
|  | GSH (nmol/10$^6$ cells) | 19.2 ± 2.4 | 10.4 ± 2.0† | 8.5 ± 1.7 | 3.7 ± 1.1† |
|  | GSSG (nmol/10$^6$ cells) | 0.4 ± 0.1 | 0.3 ± 0.1 | 0.3 ± 0.05 | 0.3 ± 0.1 |
|  | TXN (μg/10$^6$ cells) | 0.7 ± 0.2 | 0.3 ± 0.15† | 0.5 ± 0.2 | 0.2 ± 0.1* |
|  | TXNRD (U/10$^6$ cells) | 1.2 ± 0.4 | 0.7 ± 0.2* | 1.1 ± 0.3 | 0.8 ± 0.2 |
| ROS | SOD1 (U/10$^6$ cells) | 0.4 ± 0.1 | 0.2 ± 0.05* | 0.2 ± 0.1 | 0.1 ± 0.05 |
|  | SOD2 (U/10$^6$ cells) | 0.2 ± 0.05 | 0.05 ± 0.02† | 0.2 ± 0.1 | 0.05 ± 0.02* |
|  | CAT (mU/10$^6$ cells) | 1.9 ± 0.4 | 1.2 ± 0.3† | 1.6 ± 0.3 | 1.0 ± 0.2† |
|  | NOX (R.L.U./10$^6$ cells) | 103 ± 27 | 115 ± 33 | 80 ± 17 | 89 ± 25 |
|  | H$_2$O$_2$ (nmol/10$^6$ cells × min) | 2.1 ± 0.5 | 1.4 ± 0.3* | 1.9 ± 0.4 | 1.3 ± 0.2* |
|  | O$_2$·− (ΔFL1, a.u.) | 5.0 ± 1.3 | 8.4 ± 2.4* | 3.7 ± 1.1 | 5.9 ± 1.7* |
| NADPH supplying dehydrogenases | G6PDH (mU/10$^6$ cells) | 517 ± 144 | 317 ± 84* | 478 ± 127 | 264 ± 56† |
|  | ME (mU/10$^6$ cells) | 85 ± 21 | 55 ± 15 | 63 ± 18 | 40 ± 7* |
|  | IDH (U/10$^6$ cells) | 1.8 ± 0.4 | 1.0 ± 0.3† | 2.7 ± 0.6 | 1.7 ± 0.5* |
| Redox state | NADPH(nmol/mg prot) | 0.10 ± 0.02 | 0.05 ± 0.02* | 0.09 ± 0.03 | 0.03 ± 0.01† |
|  | NADP$^+$ (nmol/mg prot) | 0.01 ± 0.005 | 0.03 ± 0.01† | 0.02 ± 0.01 | 0.05 ± 0.005† |
|  | GSH/GSSG | 48 ± 7 | 35 ± 6† | 28 ± 5 | 12 ± 4† |
|  | NADPH/NADP$^+$ | 10.2 ± 1.8 | 1.7 ± 0.4† | 4.5 ± 0.6 | 0.6 ± 0.2† |

Tumor-bearing mice were treated as in FIG. 7. All parameters (see under Methods) were measured in pancreatic cancer cells isolated from tumors 28 (ASPC-1) or 35 days (BxPC-3) after inoculation. Data are mean values ± SD for 5-6 different tumors per parameter and experimental conditon.

TABLE 10

Hematology, clinical chemistry, and urinary balance data in A2058- and AsPC-1-bearing mice treated with Pter

|  | | Tumor-bearing mice | | | |
|---|---|---|---|---|---|
|  | Non-tumor-bearing mice | A2058 + vehicle control | A2058 + Pter | AsPC-1 + vehicle control | AsPC-1 + Pter |
| Hematology | | | | | |
| Hematocrit (%) | 39.4 ± 2.4 | 32.1 ± 1.7† | 34.4 ± 3.0 | 27.6 ± 2.9† | 30.1 ± 1.5† |
| Hemoglobin (g/dL) | 12.5 ± 0.5 | 12.0 ± 0.3 | 12.1 ± 0.4 | 11.5 ± 0.2* | 12.0 ± 0.3 |
| Erythrocytes (10$^6$/μL) | 8.7 ± 0.15 | 6.5 ± 0.2† | 7.0 ± 0.2† | 5.5 ± 0.15† | 6.2 ± 0.1† |
| Platelets (10$^3$/μL) | 463 ± 53 | 370 ± 44† | 393 ± 36 | 238 ± 42† | 312 ± 55† |
| Leukocytes (10$^3$/μL) | 2.5 ± 0.4 | 2.0 ± 0.3 | 2.2 ± 0.4 | 1.8 ± 0.2* | 1.9 ± 0.3* |
| Lymphocytes (10$^3$/μL) | 1.3 ± 0.3 | 1.2 ± 0.3 | 1.3 ± 0.2 | 1.0 ± 0.1 | 1.1 ± 0.2 |
| % CD3 | 1.3 ± 0.2 | 1.0 ± 0.3 | 1.2 ± 0.2 | 0.8 ± 0.2 | 0.9 ± 0.3 |
| CD4 | 1.0 ± 0.2 | 1.0 ± 0.1 | 0.9 ± 0.1 | 0.9 ± 0.1 | 0.8 ± 0.1 |
| CD8 | 0.4 ± 0.1 | 0.3 ± 0.1 | 0.4 ± 0.05 | 0.2 ± 0.05* | 0.2 ± 0.1 |
| B cells | 56.8 ± 9.6 | 67.1 ± 11.0 | 63.4 ± 7.7 | 77.6 ± 6.9* | 71.4 ± 11.4 |
| NK | 7.2 ± 1.7 | 3.3 ± 1.0† | 4.1 ± 1.5† | 2.5 ± 0.7† | 2.7 ± 1.1† |
| Neutrophils (10$^3$/μL) | 1.0 ± 0.1 | 0.7 ± 0.2* | 0.8 ± 0.2 | 0.6 ± 0.1† | 0.6 ± 0.2† |
| Monocytes (10$^3$/μL) | 0.1 ± 0.05 | 0.05 ± 0.02 | 0.04 ± 0.02* | 0.05 ± 0.01 | 0.05 ± 0.02 |
| Eosinophils (10$^3$/μL) | 0.1 ± 0.05 | 0.05 ± 0.02 | 0.05 ± 0.02 | 0.05 ± 0.01 | 0.04 ± 0.02 |
| Basophils (10$^3$/μL) | 0.0 ± 0.0 | 0.0 ± 0.0 | 0.0 ± 0.0 | 0.0 ± 0.0 | 0.0 ± 0.0 |
| Plasma osmolality (mOsm/kg) | 283 ± 12 | 305 ± 17 | 278 ± 15 | 265 ± 17 | 278 ± 16 |
| Clinical chemistry | | | | | |
| Urea (mg/dL) | 48.3 ± 6.4 | 53.7 ± 5.2 | 50.4 ± 3.1 | 50.3 ± 4.0 | 52.4 ± 5.7 |
| Uric acid (mg/dL) | 1.9 ± 0.4 | 1.5 ± 0.3 | 1.8 ± 0.4 | 1.4 ± 0.3 | 1.6 ± 0.3 |
| Total protein (g/dL) | 4.0 ± 0.3 | 3.7 + 0.6 | 3.9 ± 0.5 | 3.3 ± 0.4* | 3.5 ± 0.5 |
| Albumin (g/dL) | 3.2 ± 0.3 | 2.8 +0.4 | 2.9 ± 0.6 | 2.5 ± 0.4* | 3.0 ± 0.6 |
| Creatinine (mg/dL) | 0.4 ± 0.1 | 0.5 ± 0.1 | 0.5 ± 0.1 | 0.7 ± 0.2* | 0.5 ± 0.1 |
| Glucose (mg/dL) | 147 ± 12 | 136 ± 15 | 157 ± 19 | 105 ± 16† | 136 ± 20 |
| Total bilirubin (mg/dL) | 0.5 ± 0.1 | 0.4 ± 0.1 | 0.5 ± 0.1 | 0.6 ± 0.1 | 0.5 ± 0.1 |
| Direct bilirubin (mg/dL) | 0.1 ± 0.02 | 0.05 ± 0.01† | 0.1 ± 0.03 | 0.03 ± 0.01† | 0.1 ± 0.03 |
| Aspartate aminotransferase (IU/L ) | 153 ± 25 | 257 ± 36† | 140 ± 27 | 300 ± 45† | 166 ± 27 |
| Aspartate aminotransferase (IU/L) | 153 ± 25 | 257 ± 36† | 140 ± 27 | 300 ± 45† | 166 ± 27 |
| Alanine aminotransferase (IU/L) | 7.5 ± 2.2 | 46.5 ± 7.0† | 7.0 ± 1.6 | 55.8 ± 6.4† | 13.2 ± 3.5* |
| GGT (IU/L) | 2.0 ± 0.4 | 3.5 ± 0.6† | 2.0 ± 0.5 | 4.7 ± 0.5† | 2.3 ± 0.4 |
| Alkaline phosphatase (IU/L) | 132 ± 17 | 155 ± 24 | 140 ± 21 | 177 ± 26* | 147 ± 18 |

TABLE 10-continued

Hematology, clinical chemistry, and urinary balance data in A2058- and AsPC-1-bearing mice treated with Pter

| | Non-tumor-bearing mice | Tumor-bearing mice | | | |
|---|---|---|---|---|---|
| | | A2058 + vehicle control | A2058 + Pter | AsPC-1 + vehicle control | AsPC-1 + Pter |
| Lactate dehydrogenase (IU/L) | 220 ± 31 | 397 ± 49† | 251 ± 38 | 484 ± 55† | 288 ± 30* |
| Sodium (mEq/L) | 145 ± 12 | 157 ± 16 | 152 ± 20 | 133 ± 15 | 149 ± 14 |
| Potassium (mEq/L) | 8.3 ± 1.6 | 9.5 ± 2.0 | 7.7 ± 1.6 | 10.7 ± 2.0 | 8.9 ± 1.7 |
| Chloride (mEq/L) | 101 ± 17 | 111 ± 6 | 99 ± 10 | 122 ± 16 | 106 ± 9 |
| Isolated hepatocytes | | | | | |
| GSH (nmol/g of cells) | 5862 ± 465 | 3975 ± 418† | 4760 ± 377† | 3020 ± 364† | 4420 ± 444† |
| Cell volume (µL/mg dry wt.) | 3.2 ± 0.2 | 3.1 ± 0.3 | 2.9 ± 0.2 | 3.1 ± 0.3 | 3.0 ± 0.3 |
| Glucose utilization (µmol/g × min) | 1.43 ± 0.12 | 1.85 ± 0.17† | 1.57 ± 0.12 | 1.96 ± 0.24† | 1.50 ± 0.13 |
| Isolated CD2+ lymphocytes | | | | | |
| GSH (nmol/$10^6$ cells) | 5.2 ± 0.9 | 3.5 ± 0.7† | 4.3 ± 0.5 | 3.8 ± 0.6† | 4.2 ± 0.6 |
| Cell volume (µm$^3$) | 176 ± 12 | 194 ± 24 | 164 ± 15 | 204 ± 26 | 177 ± 14 |
| Glucose utilization (µmol/g × min) | 1.12 ± 0.11 | 1.46 ± 0.09† | 1.24 ± 0.08 | 1.57 ± 0.11† | 1.23 ± 0.15 |
| Glutamine utilization (µmol/g × min) | 3.25 ± 0.16 | 3.96 ± 0.26† | 3.35 ± 0.32 | 4.16 ± 0.28† | 3.40 ± 0.12 |
| Urinary balance | | | | | |
| pH | 7.5 ± 0.4 | 8.0 ± 0.3 | 7.7 ± 0.5 | 8.2 ± 0.5* | 7.7 ± 0.4 |
| Leukocytes (µL$^{-1}$) | Negative | Negative | Negative | Negative | Negative |
| Erythrocytes (µL$^{-1}$) | Negative | Negative | Negative | Negative | Negative |
| Nitrite | Negative | Negative | Negative | Negative | Negative |
| Protein (g/L) | 0.2 | 0.3 | 0.2 | 0.5 | 0.3 |
| Glucose | Normal | Normal | Normal | Normal | Normal |
| Ketones | Negative | Negative | Negative | Negative | Negative |
| Urobilinogen | Normal | Normal | Normal | Normal | Normal |
| Bilirubin | Negative | Negative | Negative | Negative | Negative |
| GFR (µL/min) | 175 ± 23 | 182 ± 31 | 167 ± 30 | 177 ± 15 | 186 ± 17 |

Standard cell count and chemistry were measured in peripheral blood samples taken from the saphena vein. Pter (30 mg/kg) was administered i.v. as in FIG. 1A. Tumor-bearing mice were sacrificed 28 (AsPC-1) or 35 (A2058) days after tumor inoculation. Mean ± SD of 6-7 different mice in each experimental condition.
*Significantly different $p < 0.05$,
†$p > 0.01$ comparing tumor-bearing mice versus non-tumor-bearing mice.

TABLE 11

Plasma levels of corticosterone and ACTH, and GR number in cancer cells in A2058 melanoma-bearing mice treated with EGCG or Curc + Corticosterone (CRC)

| Treatment | Tumor vol. (mm$^3$) | $10^3$ GR/cell | CRC (ng/mL plasma) | ACTH (pg/mL plasma) |
|---|---|---|---|---|
| None | 1172 ± 21 | 61 ± 11 | 265 ± 27 | 242 ± 41 |
| EGCG | 894 ± 137 | 77 ± 7 | 243 ± 31 | 215 ± 36 |
| EGCG + CRC | 967 ± 199 | 61 ± 9 | 255 ± 25 | 205 ± 18 |
| Curc | 606 ± 126* | 71 ± 12 | 161 ± 17* | 113 ± 25* |
| Curc + CRC | 1044 ± 276 | 80 ± 10 | 297 ± 39 | 227 ± 52 |

Figure 12:
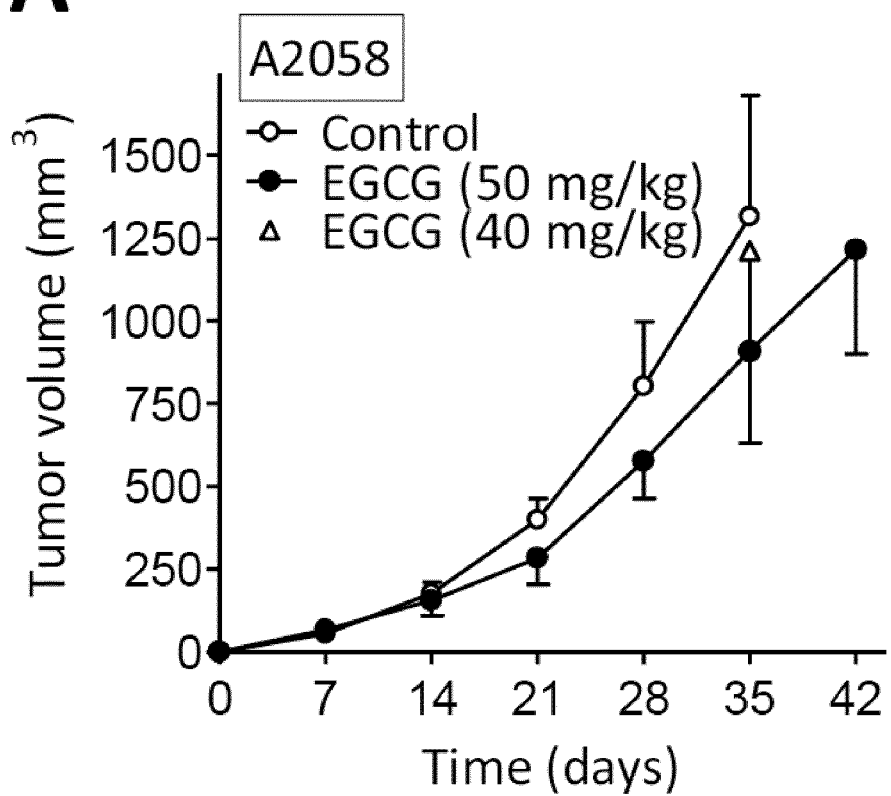
FIG. 12. Effect of (–)-epigallocatechin-3-gallate (EGCG) or curcumin (Curc) treatment on (A) human melanoma (A2058) and (B) pancreatic cancer (AsPC-1) growth in vivo. EGCG or Curc were administered i.v. every 48 h for a period of 5 weeks, starting 1 week after tumor cell inoculation. For this purpose EGCG was dissolved in physiological saline, whereas Curc was dissolved in DMSO. In our experimental conditions the dose of 50 mg/kg every 48 h did not cause deaths in the treated groups. But a higher dose (60 mg EGCG or Curc/kg) caused 45% deaths in the tumor-bearing groups treated with EGCG, and 15% deaths in the tumor-bearing groups treated with Curc (results not shown). All data are mean values±SD of 20 different animals. *Significantly different p<0.01 comparing EGCG- or Curc-treated mice vs controls.
Figure 12:
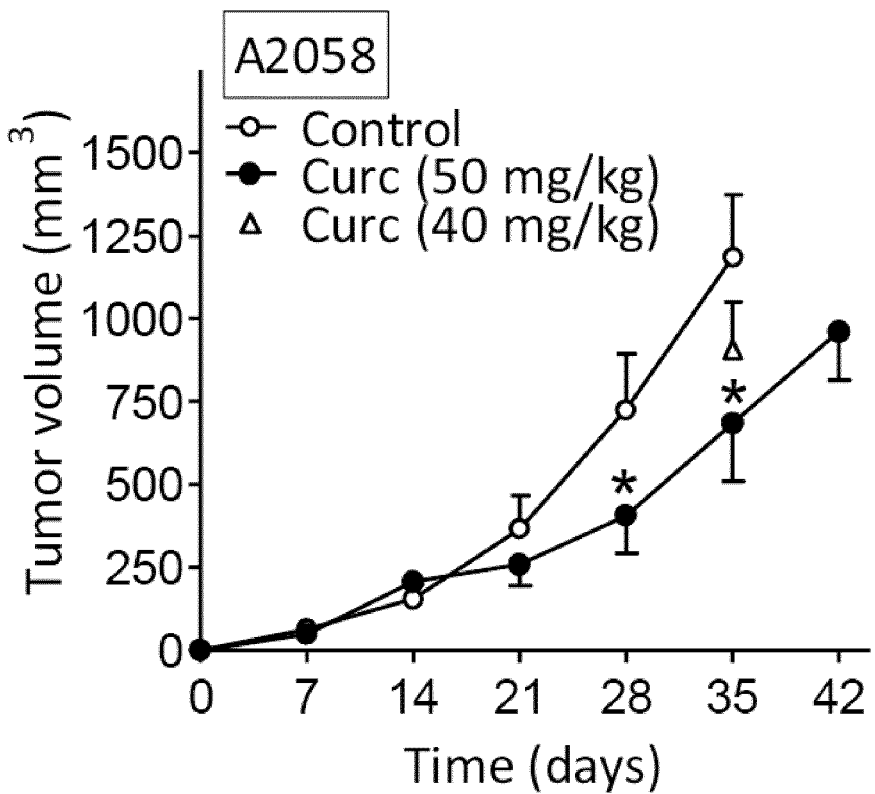
Figure 12:
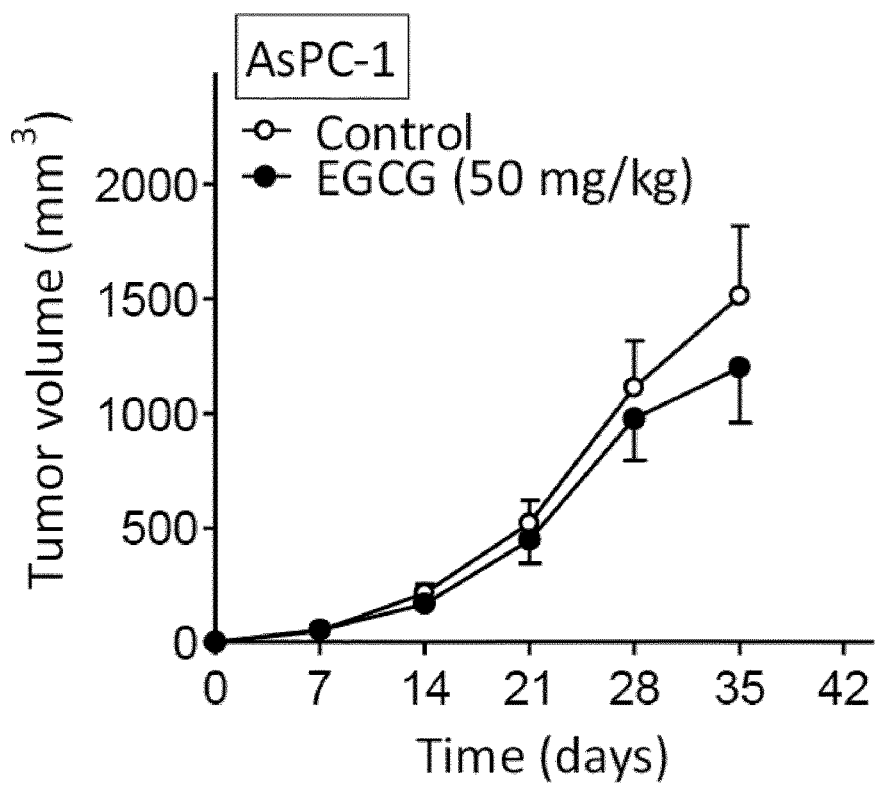
Figure 12:
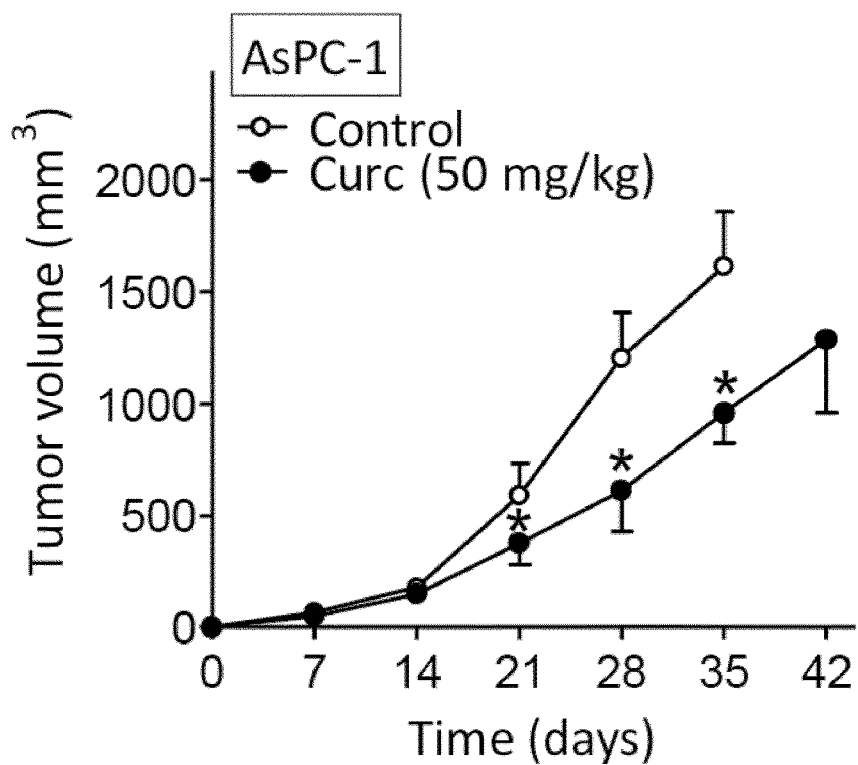
Figure 13:
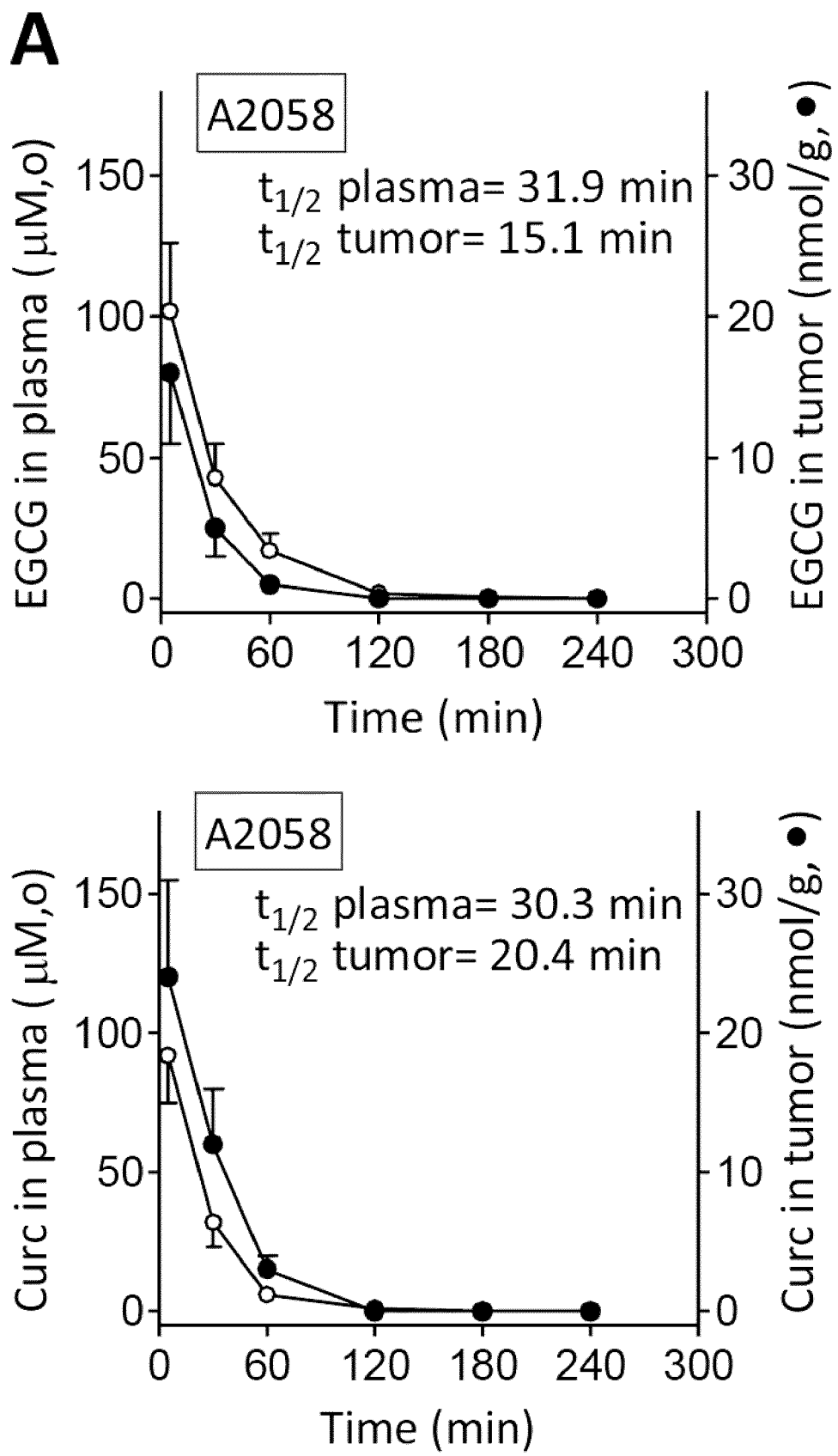
FIG. 13. Plasma vs tumor levels (A), and brain and pituitary levels (B) of EGCG and Curc after its i.v. administration (50 mg/kg) to A2058 melanoma-bearing mice. All data are mean values±SD of 5-6 different animals.
Figure 13:
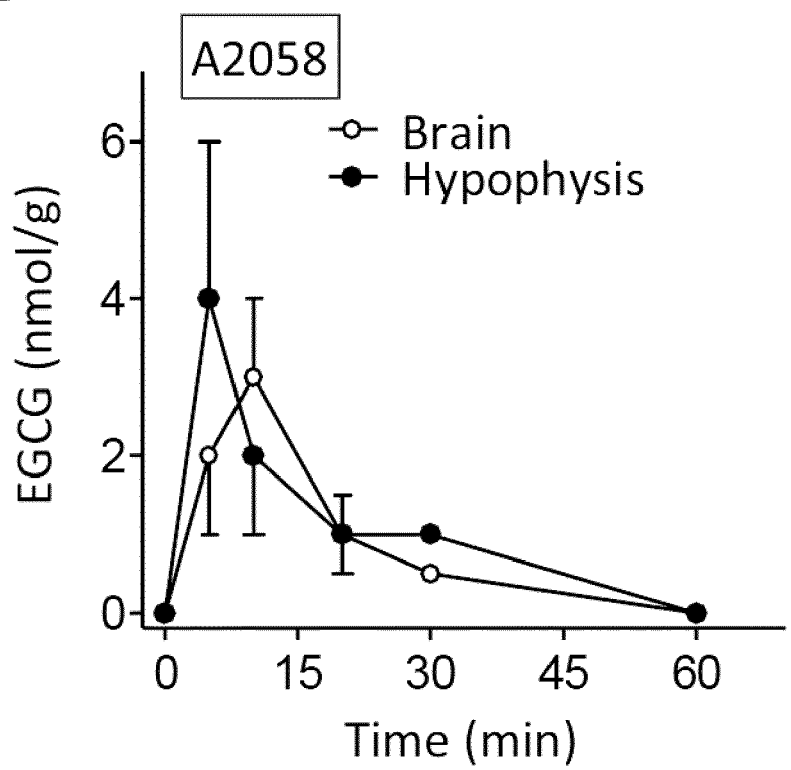
Figure 13:
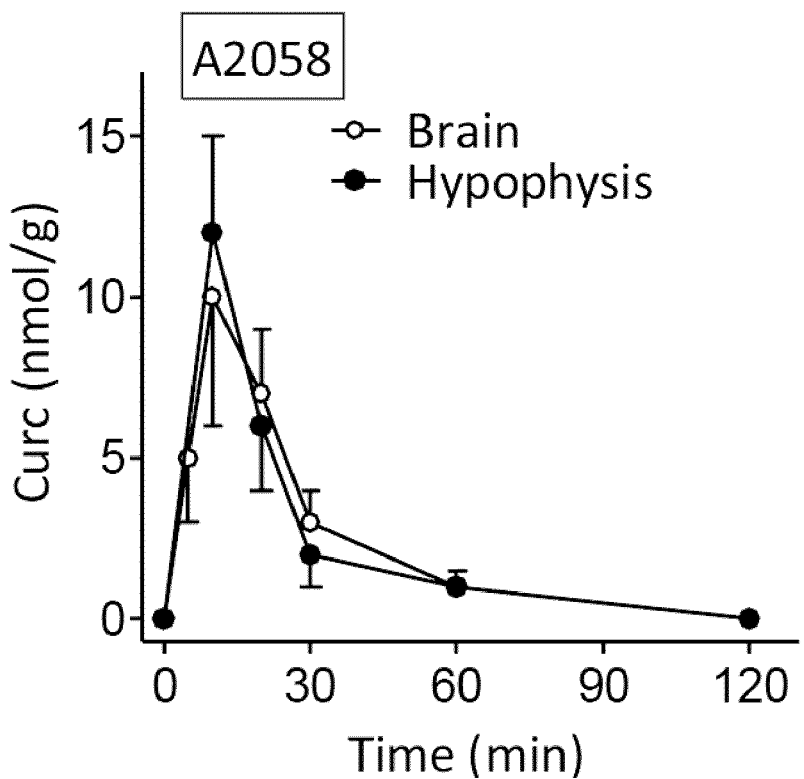

Melanoma cells stably expressing the red fluorescence protein (RFP) were inoculated, as in Table 4, and allowed to grow for 35 days. Treatment with EGCG or Curc (50 mg/kg) was performed as in FIG. 12. Treatment of tumor-bearing mice with vehicles (see Methods) did not significantly affect the rate of growth as compared to controls (not shown). Data for GR number, tumor volume (Tumor vol.), corticosterone (CRC) (blood samples were obtained at 12 h circadian time) and ACTH (blood samples were obtained at 6 h circadian time) displayed in this table were obtained 35 days after tumor inoculation. All tumors had 50-80 mm$^3$ of volume on day 7 after inoculation. GR number on day 7 was not significantly different from GR number on day 35 (not shown). Data are mean values ± SD of 4-5 different animals.
*Significantly different $p < 0.01$ comparing all groups vs controls (untreated). Data obtained in melanoma-bearing mice treated with vehicle were not significantly different from those calculated for the untreated group (not shown).

TABLE 12

Plasma Levels of Corticosterone and GR Number in Cancer Cells in Murine B16-F1 Melanoma Bearing-Mice Treated with Pter and corticosterone (CRC)

| | B16-F1 | | |
|---|---|---|---|
| Treatment | Tumor vol. (mm$^3$) | $10^3$ GR/cell | CRC (ng/mL plasma) |
| None | 1412 ± 303 | 106 ± 15 | 395 ± 57 |
| Pter | 790 ± 156* | 112 ± 16 | 187 ± 36* |
| Pter + CRC | 1237 ± 244 | 94 ± 12 | 351 ± 69 |

Figure 14:
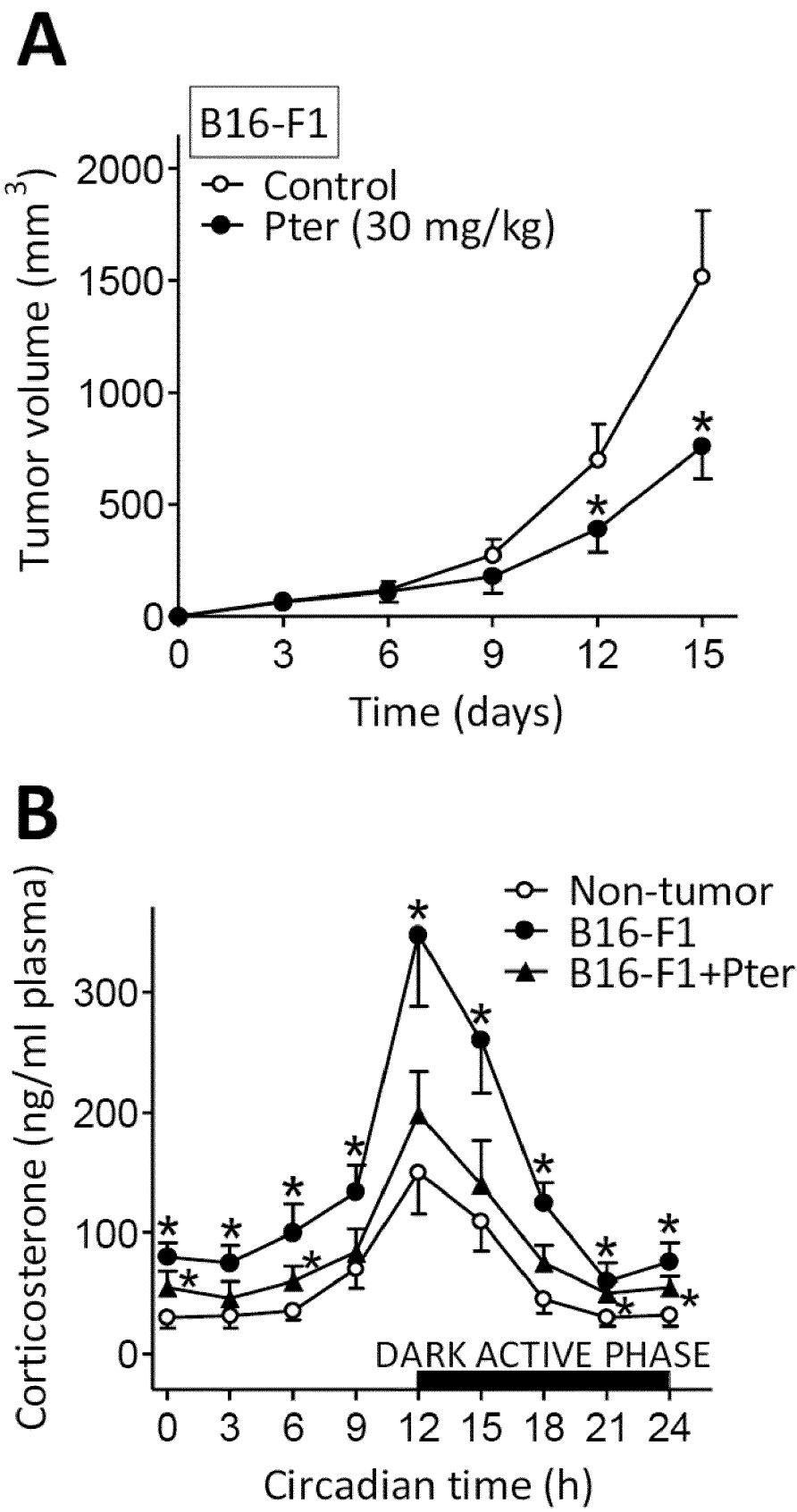
FIG. 14. In vivo effect of Pter on tumor growth (A) and on corticosterone (B) and ACTH (C) levels in plasma of murine B16-F1 melanoma-bearing mice. Pter (30 mg/kg) was administered i.v. every 24 h for a period of 15 days, starting 3 days after tumor inoculation. Using the same methodology as in FIG. 1B we calculated a half-life of Pter in circulating plasma of B16-F1-bearing mice of 61.2 min (not significantly different from that calculated in non-tumor bearing mice where the same dose of Pter was administered i.v., not shown), and of 29.3 min in the B16-F1 tumors. Under in vitro conditions 15 μM Pter×60 min every 24 h starting 24 h after seeding (as in FIG. 1C) did not affect B16-F1 cell growth or viability (not shown). All data are mean values±SD of 5-6 different animals. *Significantly different p<0.01 comparing Pter-treated mice vs controls.
Figure 14:
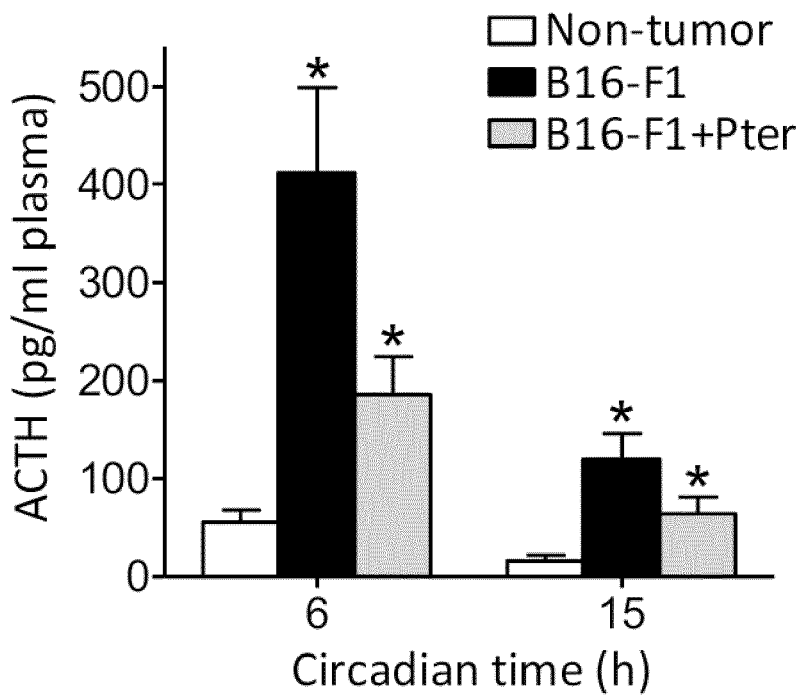

B16-F1 cells stably expressing the RFP (transfection was performed using the same methodology used for human melanoma cells) were inoculated, as in FIG. 1, and allowed to grow for 15 days. Treatment with Pter and corticosterone was performed as in FIG. 14 and Table 4, respectively. Treatment of tumor-bearing mice with vehicles (DMSO-ethanol for Pter as indicated under Methods; or polyethylene glycol 400 for corticosterone) did not significantly affect the rate of B16-F1 growth as compared to controls (not shown). The number of GR (expressed as binding sites/cell) was not significantly different when 72 h-cultured B16-F1-RFP cells were compared with their wild type B16-F1 cell counterparts (not shown). Data for GR number, tumor volume (Tumor vol.) and corticosterone (blood samples were obtained at 12 h circadian time) displayed in this table were obtained 15 days after tumor inoculation. All tumors had 50-70 mm$^3$ of volume on day 3 after inoculation. GR number on day 3 was not significantly different from GR number on day 15 (not shown). Data are mean values ± SD of 4-5 different animals.
*Significantly different $p < 0.01$ comparing all groups vs controls (untreated). Data obtained in B16-F1-bearing mice treated with vehicle were not significantly different from those calculated for the untreated group (not shown).

TABLE 13

Plasma levels of corticosterone (CRC) and ACTH, and GR number in cancer cells in cancer cells in human breast-, lung-, liver-, prostate-, ovarian-, or colorectal-bearing mice treated with Pter

| Cancer | Cell type | Treatment | Tumor vol. (mm³) | 10³ GR/cell | CRC (ng/mL plasma) | ACTH (pg/mL plasma) |
|---|---|---|---|---|---|---|
| Breast | MDA-MB-231 | None | 479 ± 117 | 16 ± 5 | 207 ± 57 | 127 ± 31 |
| | | Pter | 266 ± 89* | 18 ± 3 | 84 ± 24* | 65 ± 17* |
| | MCF-7 | None | 845 ± 204 | <1 | 135 ± 31 | 96 ± 22 |
| | | Pter | 689 ± 153 | <1 | 75 ± 20* | 44 ± 9* |
| Lung | A549 | None | 547 ± 156 | 37 ± 7 | 179 ± 45 | 154 ± 44 |
| | | Pter | 223 ± 88* | 41 ± 10 | 61 ± 17* | 79 ± 19* |
| Liver parenchyma | HepG2 | None | 702 ± 145 | 52 ± 12 | 312 ± 62 | 255 ± 59 |
| | | Pter | 375 ± 106* | 45 ± 11 | 187 ± 50* | 116 ± 25* |
| Prostate | LNCaP | None | 830 ± 206 | 2 ± 1 | 174 ± 38 | 108 ± 26 |
| | | Pter | 757 ± 194 | 3 ± 1 | 77 ± 15* | 49 ± 15* |
| | PC-3 | None | 525 ± 155 | 20 ± 5 | 307 ± 79 | 214 ± 66 |
| | | Pter | 276 ± 74* | 21 ± 6 | 145 ± 30* | 102 ± 30* |
| Ovarian | SK-OV-3 | None | 615 ± 176 | 27 ± 4 | 252 ± 64 | 131 ± 35 |
| | | Pter | 214 ± 83* | 25 ± 7 | 64 ± 18* | 63 ± 19* |
| Colorectal | HT-29 | None | 1079 ± 367 | 15 ± 4 | 255 ± 49 | 109 ± 26 |
| | | Pter | 758 ± 214 | 14 ± 3 | 126 ± 36* | 44 ± 16* |
| | Caco-2 | None | 950 ± 247 | 6 ± 2 | 189 ± 55 | 97 ± 29 |
| | | Pter | 795 ± 285 | 7 ± 2 | 106 ± 23* | 35 ± 15* |

Figure 3:
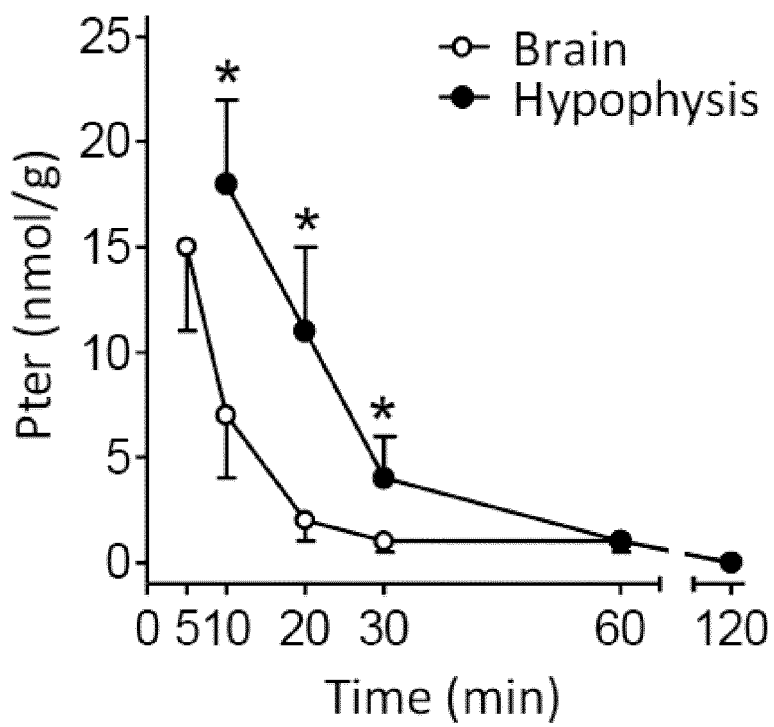
FIG. 3. Pterostilbene bioavailability in brain and the pituitary gland, and its effect on ACTH synthesis and POMC expression in AtT-20 cells. (A) Whole brain and pituitary gland levels of pterostilbene after its i.v. administration (30 mg/kg) (n=6-7 mice; *Significantly different $p<0.01$ comparing hypophysis vs whole brain levels). Data in FIG. 3A correspond to tissues obtained from non-tumor-bearing mice (results obtained in A2058 or MeWo melanoma-bearing mice were not significantly different, not shown). (B) Effect of pterostilbene on ACTH production by AtT-20 cells in a 24 h-period (measured between 24-48 h or between 48-72 h). (C) Effect of pterostilbene on POMC expression and (D) POMC protein levels (72 h of culture time) in AtT-20 cells (n=6 for B, C, and D; *Significantly different $p<0.01$ comparing +pterostilbene vs control). For the in vitro experiments (B, C, and D) pterostilbene (15 mM, see under Results) and CRH (100 nM) were added at time 0 and every 24 h along the culture time and were present, after each addition, for only 30 min. After the 30 min period, culture flasks were washed out (three times with PBS) and the medium was renewed (controls received identical treatment).
Figure 3:
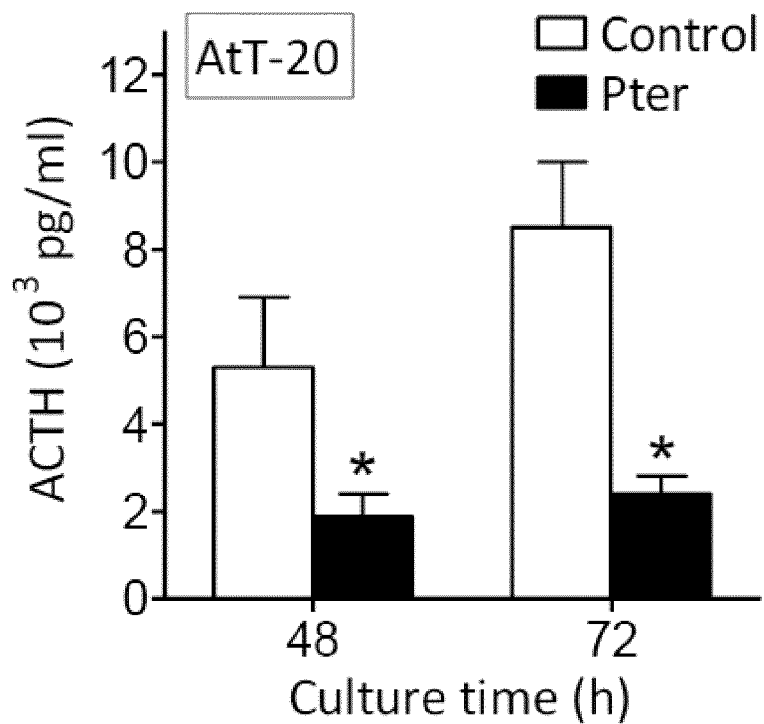
Figure 3:
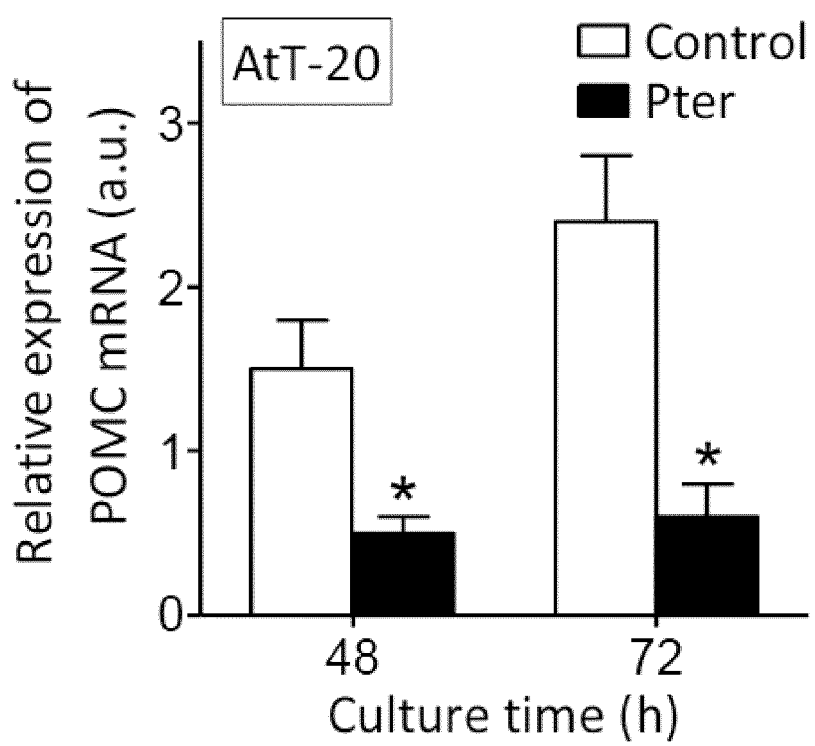
Figure 3:
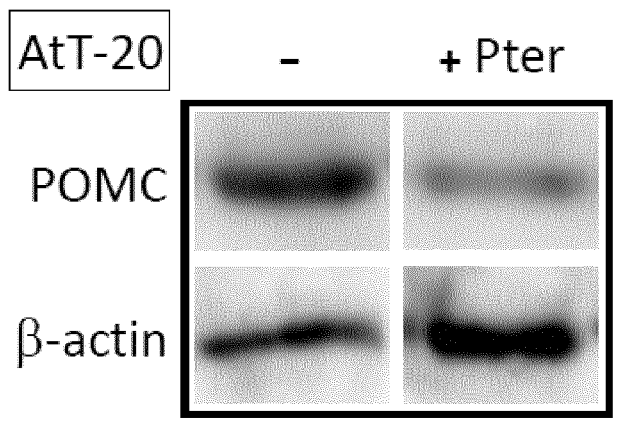

Cancer cells were inoculated, as in FIG. 3 and allowed to grow for 35 (MDA-MB-231), 28 (MCF-7), 35 (A549), 35 (HepG2), 49 (LNCaP), 21 (PC-3), 49 (SK-OV-3), 21 (HT-29), or 28 (Caco-2) days. Treatment with Pter (as in Supplementary FIG. S2) was performed as in Table 1. Treatment of tumor-bearing mice with vehicles (DMSO-ethanol for Pter as indicated under the Methods section) did not significantly affect the rate of cancer growth compared with controls (not shown). The number of GRs (expressed as binding sites/cell) was not significantly different when 72 h cultured cancer cells were compared with their wild-type cell counterparts (not shown). Data for GR number, tumor volume (Tumor vol.), and CRC (blood samples were obtained at 12 h circadian time) displayed in this table were obtained for days after tumor inoculation indicated above for each cancer type. Data for ACTH levels were obtained at 6 h circadian time. All tumors had 50-70 mm³ of volume on day 7 after inoculation. GR number on day 7 was not significantly different from GR number on days 21-49 (not shown). Data are mean values ± SD of 5-6 different animals.
*Significantly different $p < 0.01$ comparing all groups versus controls (untreated). Data obtained in cancer-bearing mice treated with vehicle were not significantly different from those calculated for the untreated group (not shown).
ACTH, adrenocorticotropin hormone;
CRC, corticosterone;
GR, glucocorticoid receptors.

TABLE 14

GSH levels and glutathione- and oxidative stress-related enzyme activities in cancer cells in human breast-, lung-, liver-, prostate-, ovarian-, or colorectal-bearing mice treated with Pter

| Cancer | Cell type | Treatment | GSH (nmol/10⁶ cells) | GSSG (nmol/10⁶ cells) | GCL (mU/10⁶ cells) | GSS (mU/10⁶ cells) | SOD1 (U/10⁶ cells) | SOD2 (U/10⁶ cells) | CAT (mU/10⁶ cells) |
|---|---|---|---|---|---|---|---|---|---|
| Breast | MDA-MB-231 | None | 23.8 ± 3.5 | 0.3 ± 0.01 | 145 ± 27 | 16.5 ± 4.9 | 0.6 ± 0.2 | 0.05 ± 0.02 | 1.1 ± 0.3 |
| | | Pter | 11.5 ± 2.0† | 0.2 ± 0.05* | 66 ± 18† | 7.7 ± 1.2† | 0.3 ± 0.08* | 0.03 ± 0.01* | 0.6 ± 0.2* |
| | MCF-7 | None | 32.4 ± 5.4 | 0.4 ± 0.1 | 184 ± 46 | 23.1 ± 3.8 | 1.1 ± 0.3 | 0.15 ± 0.04 | 0.5 ± 0.1 |
| | | Pter | 30.6 ± 4.2 | 0.3 ± 0.1 | 166 ± 34 | 25.2 ± 5.6 | 1.0 ± 0.08 | 0.12 ± 0.05 | 0.5 ± 0.2 |
| Lung | A549 | None | 8.3 ± 1.7 | 0.2 ± 0.05 | 77 ± 25 | 8.6 ± 2.5 | 0.9 ± 0.3 | 0.09 ± 0.02 | 0.7 ± 0.3 |
| | | Pter | 4.7 ± 1.5† | 0.2 ± 0.07 | 39 ± 16 | 3.9 ± 1.0† | 0.5 ± 0.1* | 0.04 ± 0.01† | 0.3 ± 0.01* |
| Liver parenchyma | HepG2 | None | 18.2 ± 3.5 | 0.2 ± 0.09 | 112 ± 38 | 9.7 ± 2.3 | 0.3 ± 0.06 | 0.04 ± 0.02 | 2.6 ± 0.6 |
| | | Pter | 8.5 ± 2.6† | 0.3 ± 0.1 | 50 ± 15† | 4.8 ± 0.9† | 0.1 ± 0.02† | 0.02 ± 0.01 | 1.1 ± 0.3† |
| Prostate | LNCaP | None | 3.5 ± 1.7 | 0.05 ± 0.02 | 33 ± 12 | 4.1 ± 1.1 | 0.4 ± 0.1 | 0.05 ± 0.02 | 1.8 ± 0.4 |
| | | Pter | 3.7 ± 1.5 | 0.12 ± 0.05* | 45 ± 14 | 4.0 ± 1.2 | 0.5 ± 0.1 | 0.01 ± 0.005† | 1.9 ± 0.5 |
| | PC-3 | None | 5.7 ± 1.6 | 0.1 ± 0.02 | 50 ± 11 | 4.7 ± 1.3 | 0.2 ± 0.05 | 0.03 ± 0.01 | 0.6 ± 0.2 |
| | | Pter | 2.4 ± 1.1* | 0.05 ± 0.02 | 27 ± 9† | 2.7 ± 0.7† | 0.05 ± 0.01† | 0.01 ± 0.005† | 0.3 ± 0.1* |
| Ovarian | SK-OV-3 | None | 4.3 ± 1.0 | 0.1 ± 0.03 | 42 ± 13 | 4.4 ± 1.0 | 0.2 ± 0.1 | 0.02 ± 0.01 | 3.4 ± 0.8 |
| | | Pter | 1.5 ± 0.7† | 0.2 ± 0.05 | 18 ± 6† | 1.6 ± 0.4† | 0.1 ± 0.03 | 0.01 ± 0.005 | 1.8 ± 0.4† |
| Colorectal | HT-29 | None | 14 ± 3 | 0.1 ± 0.04 | 103 ± 34 | 7.2 ± 2.4 | 0.4 ± 0.2 | 0.06 ± 0.03 | 0.6 ± 0.2 |
| | | Pter | 8 ± 2† | 0.05 ± 0.02† | 57 ± 17† | 6.5 ± 1.7 | 0.2 ± 0.1 | 0.02 ± 0.01† | 0.3 ± 0.1† |
| | Caco-2 | None | 9 ± 3 | 0.05 ± 0.02 | 49 ± 20 | 5.7 ± 2.0 | 0.8 ± 0.2 | 0.05 ± 0.02 | 0.7 ± 0.2 |
| | | Pter | 8 ± 3 | 0.2 ± 0.1† | 45 ± 14 | 5.5 ± 1.9 | 0.8 ± 0.3 | 0.04 ± 0.01 | 0.7 ± 0.2 |

Figure 15:
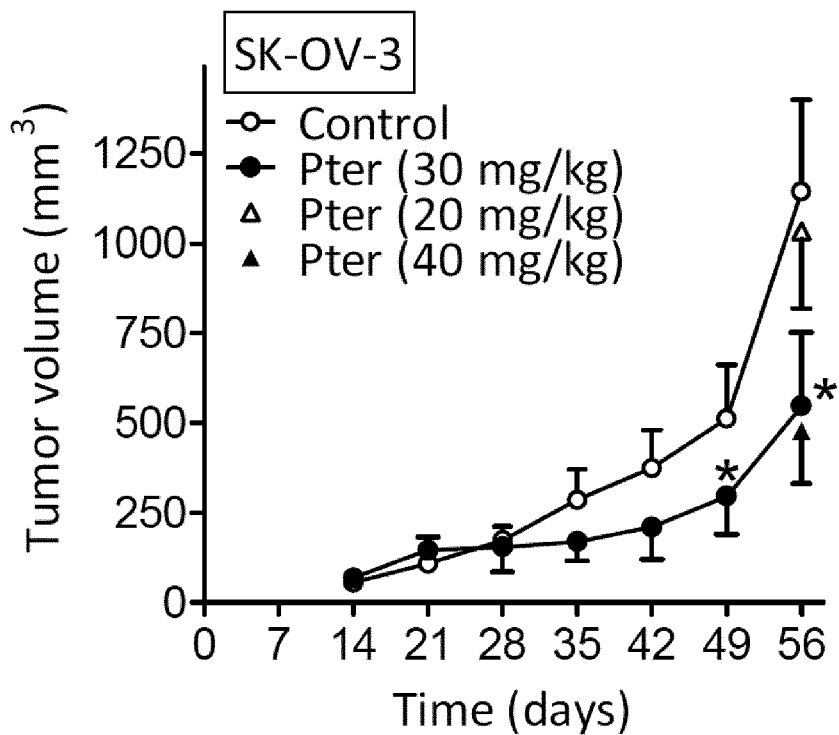
FIG. 15. In vivo effect of Pter on human breast, lung, liver, prostate, ovarian, and colorectal cancer growth. Pter was administered i.v. every 48 h for a period of 3-6 weeks, starting 1 week after tumor inoculation. For the lower and maximum Pter dose used, in each case, only the endpoint of the treatment period is shown. Plasma vs tumor levels of Pter after its i.v. administration (30 mg/kg) were not significantly different from those calculated for melanoma-bearing mice (not shown). Under in vitro conditions 15 μM Pter×60 min every 24 h starting 24 h after seeding (as in FIG. 1C) did not affect cell growth or viability in any of the tumor cell lines used (not shown). All data displayed All data are mean values±SD of 7-8 different animals. *Significantly different p<0.01 comparing Pter-treated mice vs controls.
Figure 15:
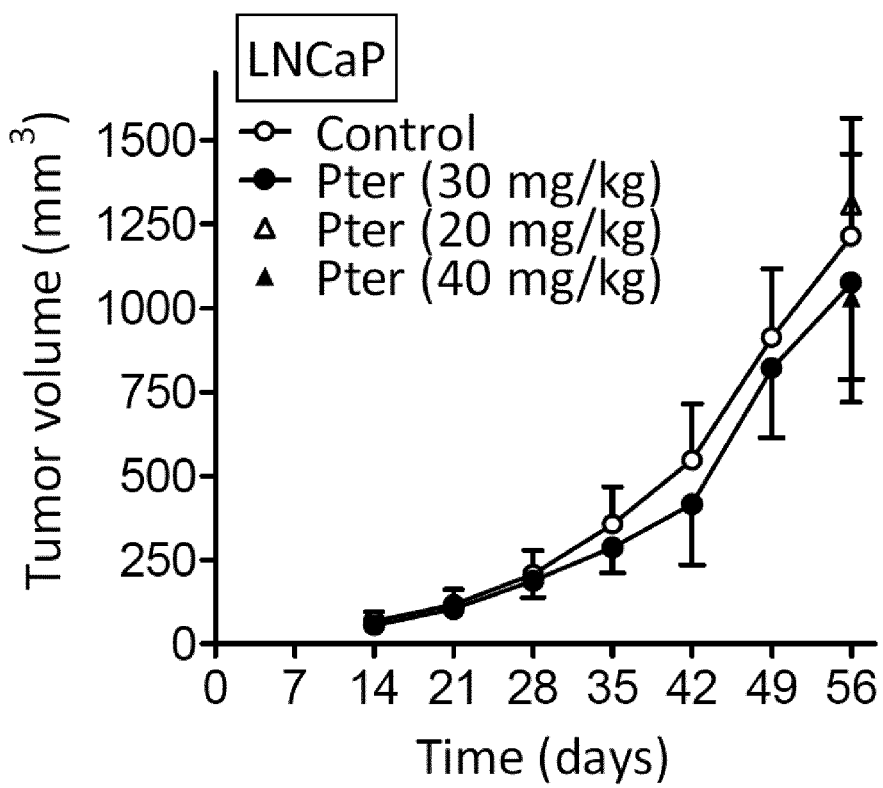
Figure 15:
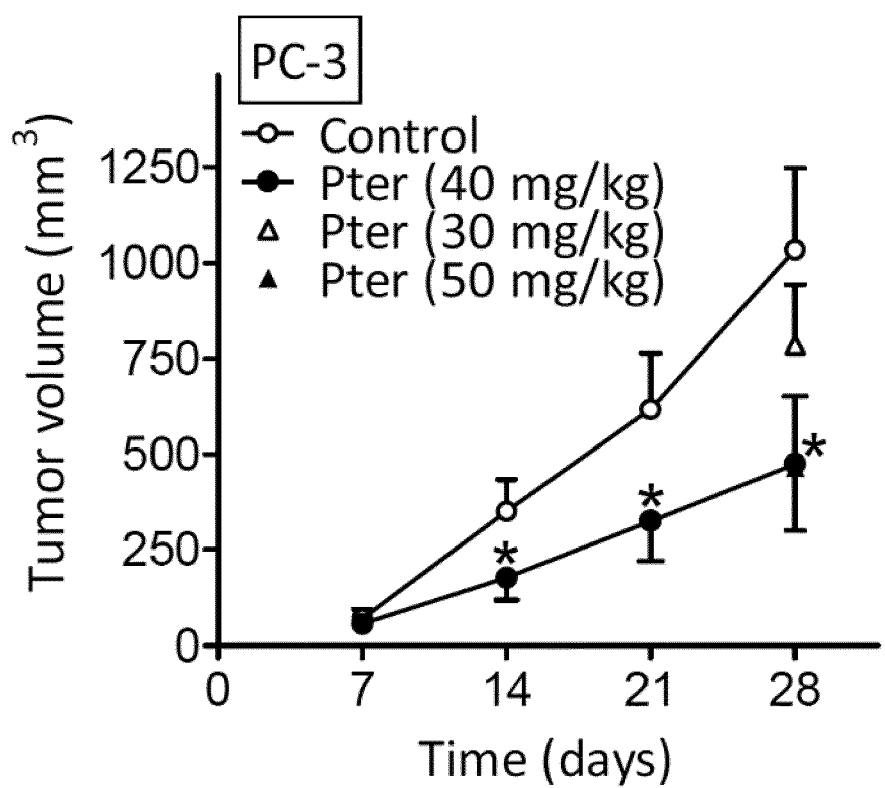
Figure 15:
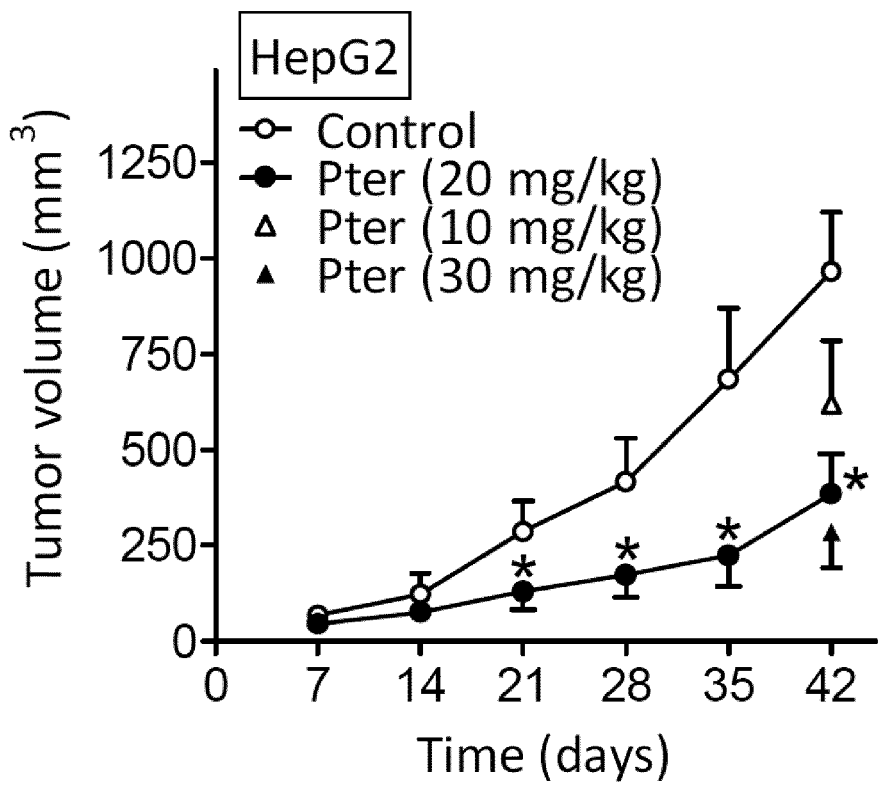
Figure 15:
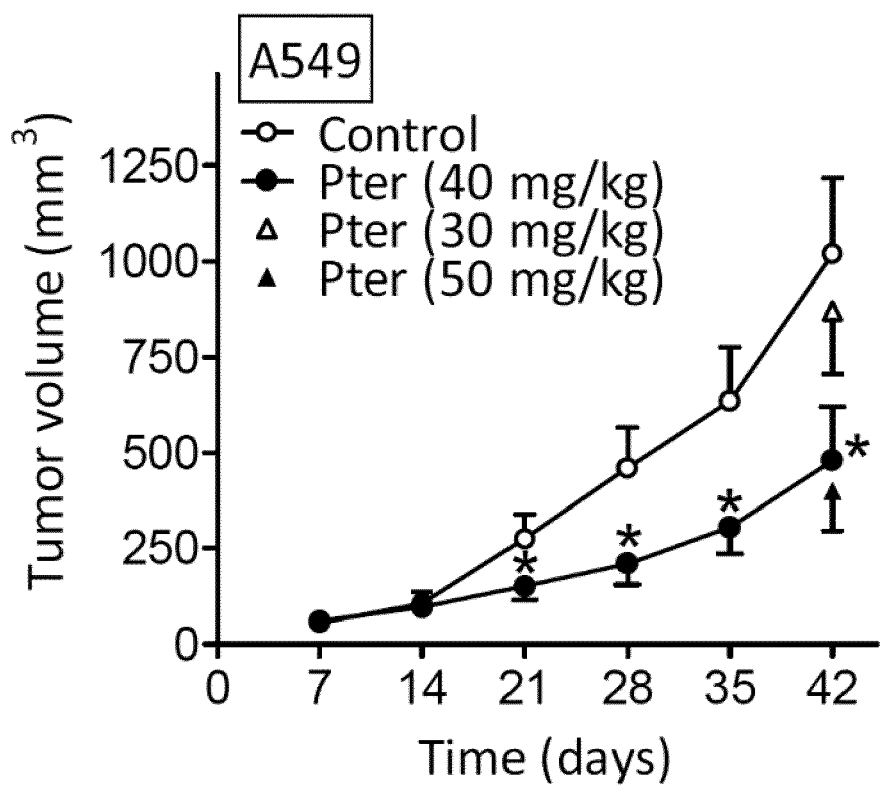
Figure 15:
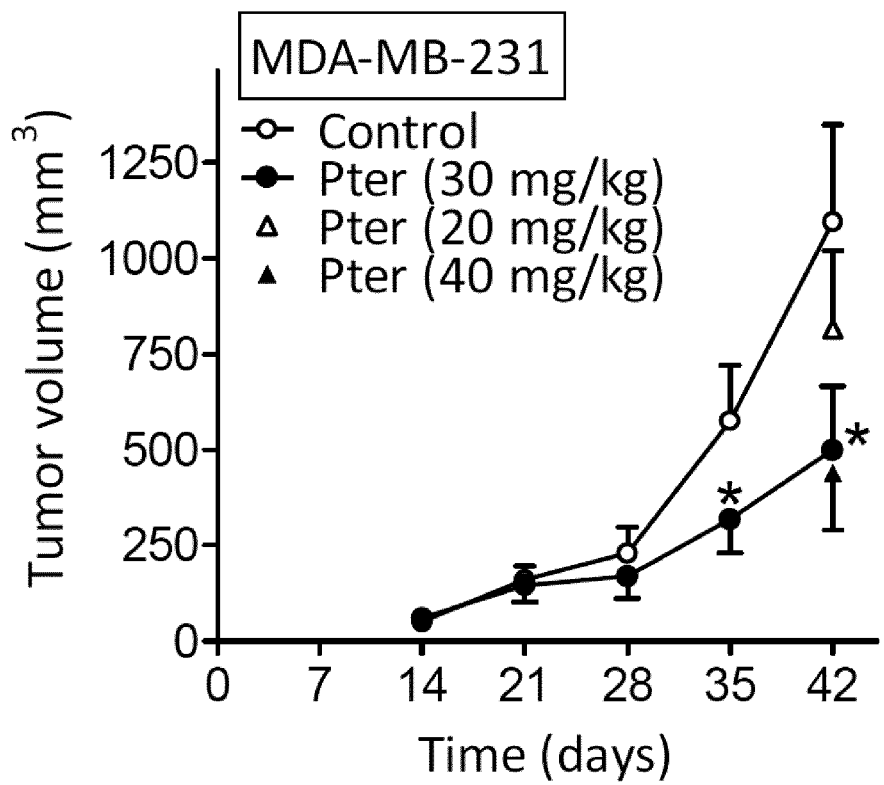
Figure 15:
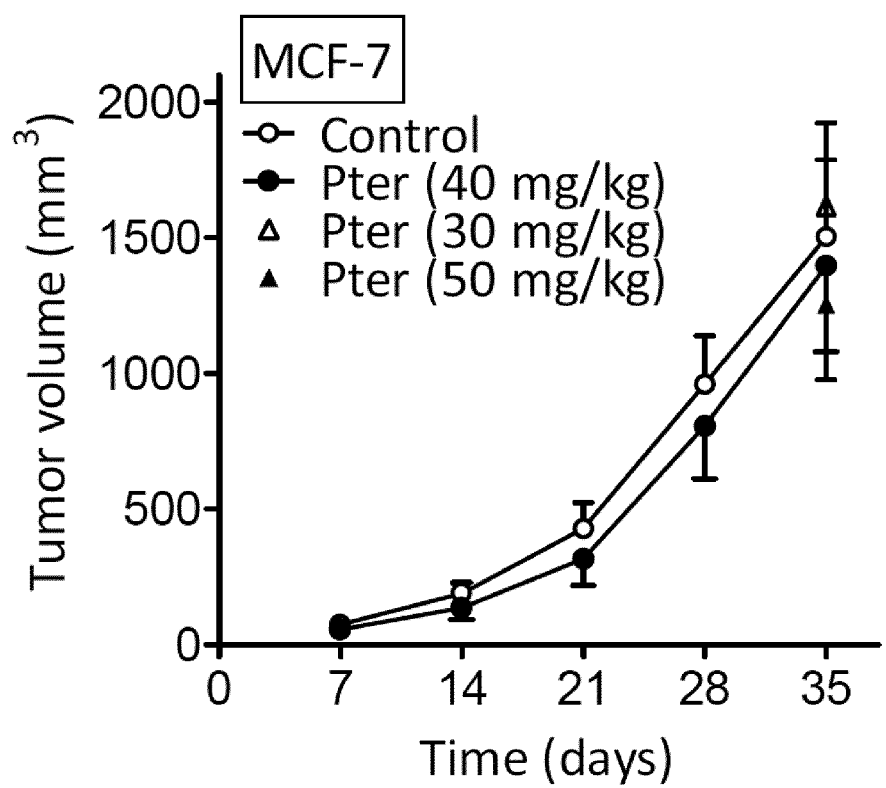
Figure 15:
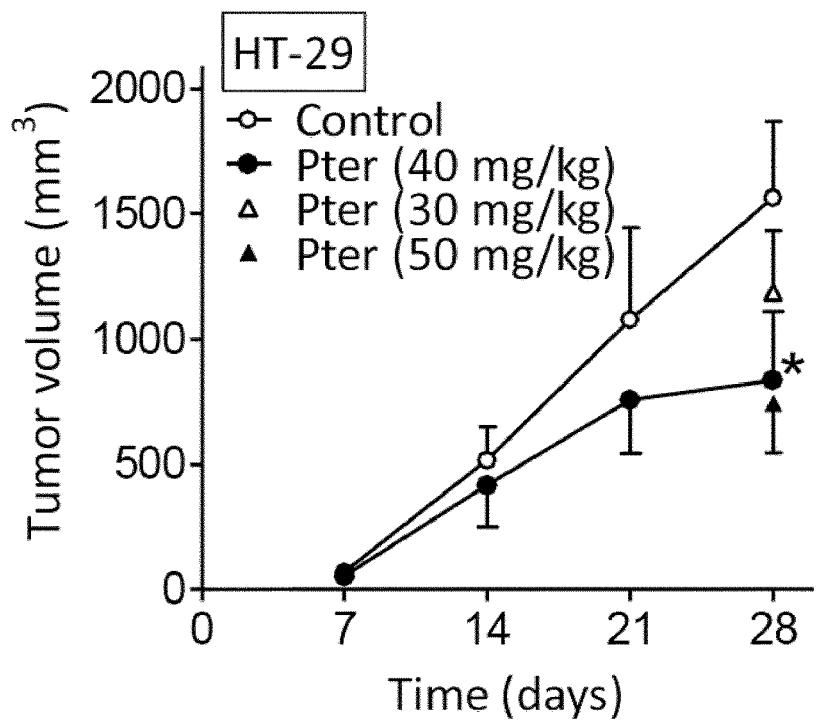
Figure 15:
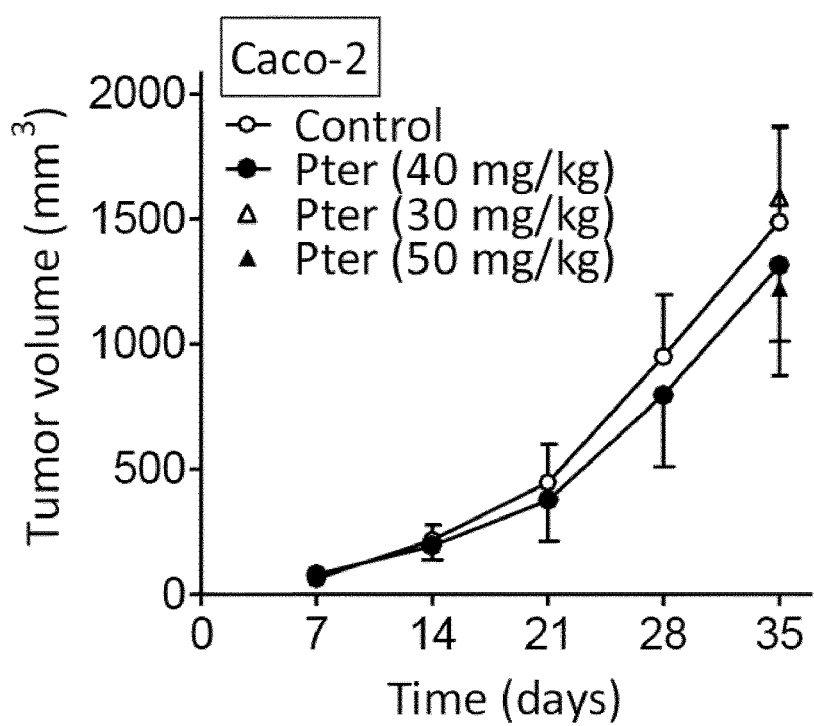
Figure 16:
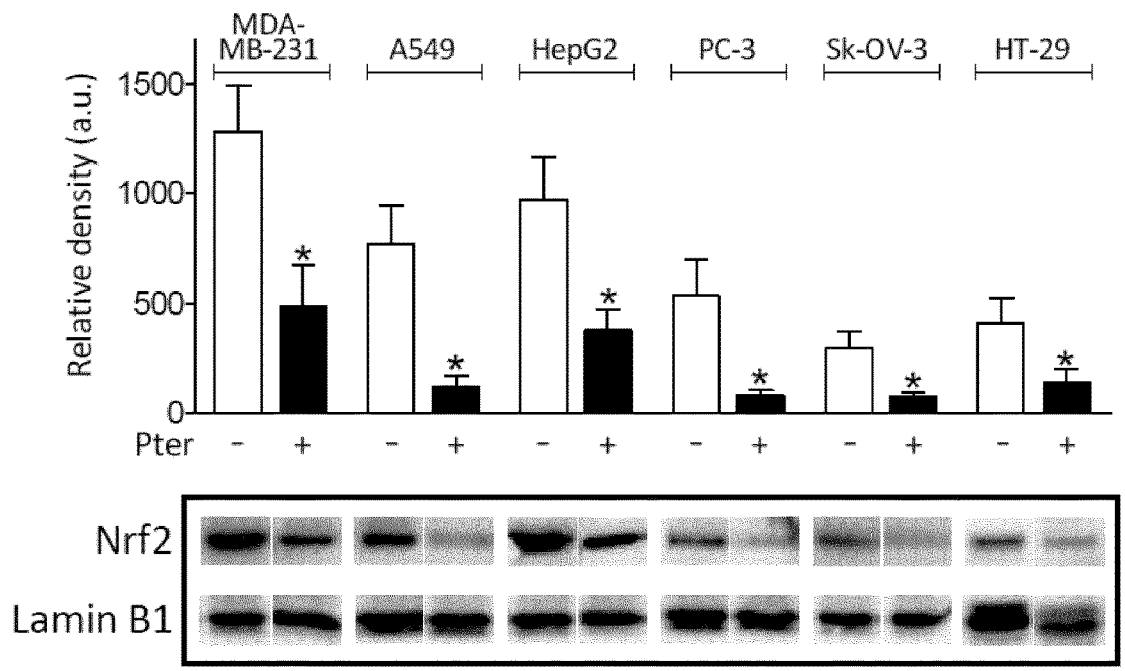
FIG. 16. In vivo effect of Pter on nuclear Nrf2 in growing human breast, lung, liver, prostate and ovarian cancer. Nuclear accumulation of Nrf2 from in vivo growing MDA-MB-231, A549, HepG2, PC-3, SK-OV-3, and HT-29 cells (as in Table 13) was measured by Western blotting (mean values±SD for four different experiments, *Significantly different p<0.01, comparing Pter treatment versus controls).

Tumor-bearing mice were treated as in FIG. 15. All parameters (see under the Methods section) were measured in the different cancer cells at the time point indicated in the caption of Table 13. Data are mean values ± SD for 5-6 different tumors per parameter and experimental condition.
*Significantly different $p < 0.05$.
†$p < 0.01$.

TABLE 15

Effect of piperlongumine (PL) and chemotherapy (Chemo) on 72 h- cultured cell viability in cancer cells isolated from control and pterostilbene (Pter)-treated tumor-bearing mice.

| | Viable cells (×10$^6$) In vitro ... | | | |
|---|---|---|---|---|
| | Control | | PL + Chemo | |
| | In vivo pretreatment ... | | | |
| Cell type | None | +Pter | None | +Pter |
| A2058 | 1124 ± 214 | 1015 ± 144 | 412 ± 78* | 35 ± 15*† |
| AsPC-1 | 1516 ± 306 | 1249 ± 206 | 557 ± 117* | 21 ± 12*† |
| MDA-MB-231 | 1045 ± 176 | 966 ± 177 | 512 ± 126* | 147 ± 38*† |
| A549 | 1458 ± 244 | 1317 ± 255 | 565 ± 133* | 33 ± 10*† |
| HepG2 | 1730 ± 319 | 1580 ± 318 | 633 ± 168* | 35 ± 16*† |
| PC-3 | 945 ± 201 | 826 ± 194 | 296 ± 105* | 65 ± 21*† |
| SK-OV-3 | 712 ± 145 | 558 ± 106 | 241 ± 64* | 77 ± 17*† |
| HT-29 | 1774 ± 266 | 1543 ± 278 | 617 ± 196* | 23 ± 9*† |

Figure 5:
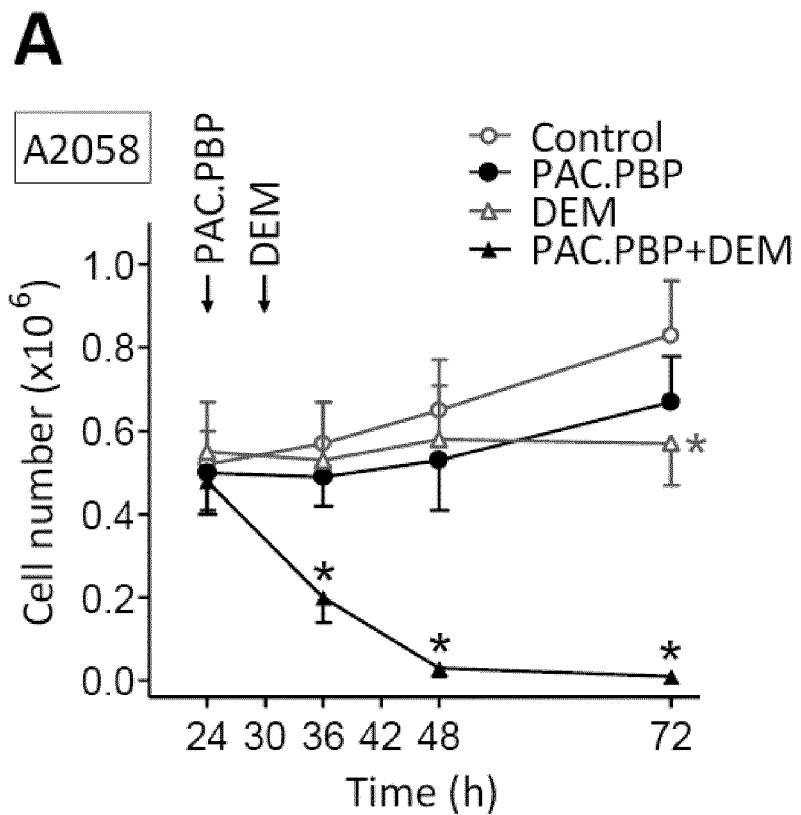
FIG. 5. Chemosensitization effect of GSH depletion (A) or sod1-AS (B) in melanoma cells isolated from Pter-treated mice. Melanoma cells were cultured as in FIG. 1C. PAC.PBP (100 ng/ml) was added to the culture flasks 24 h after seeding. DEM (0.1 mM) was added 6 h later, whereas sod1-AS (10 mM) were added 12 h after seeding [complexation with lipofectamine 2000 (Invitrogen) was used to facilitate sod1-AS uptake by the cells]. Data are mean values±SD for 5-6 different experiments (*p<0.01, comparing all experimental conditions vs controls).
Figure 5:
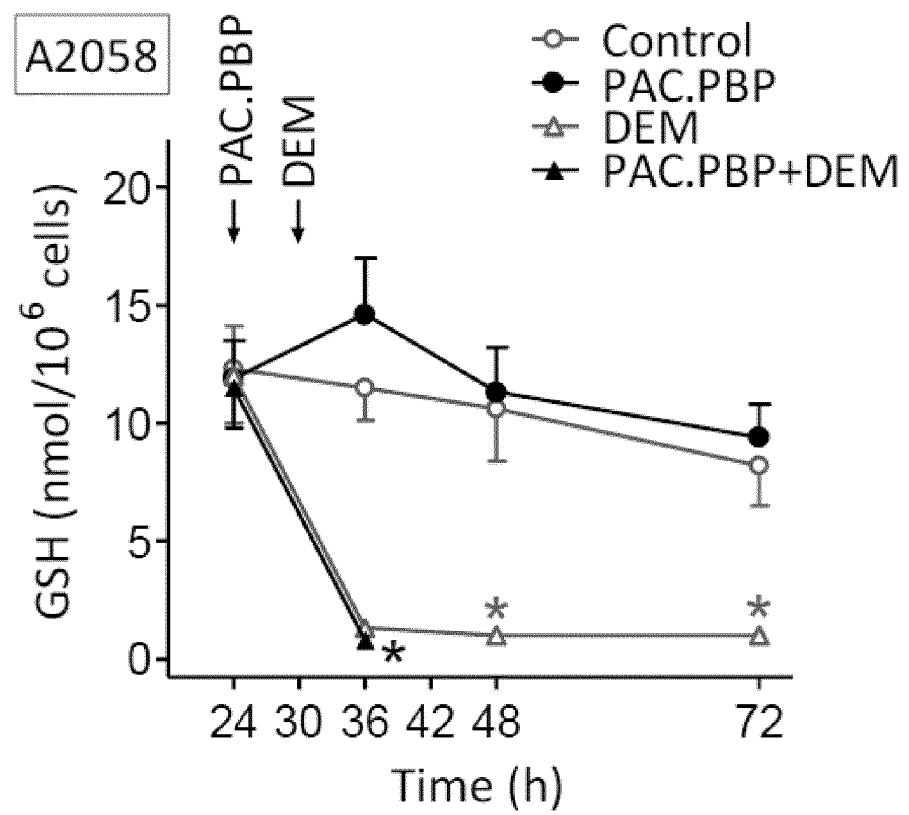
Figure 5:
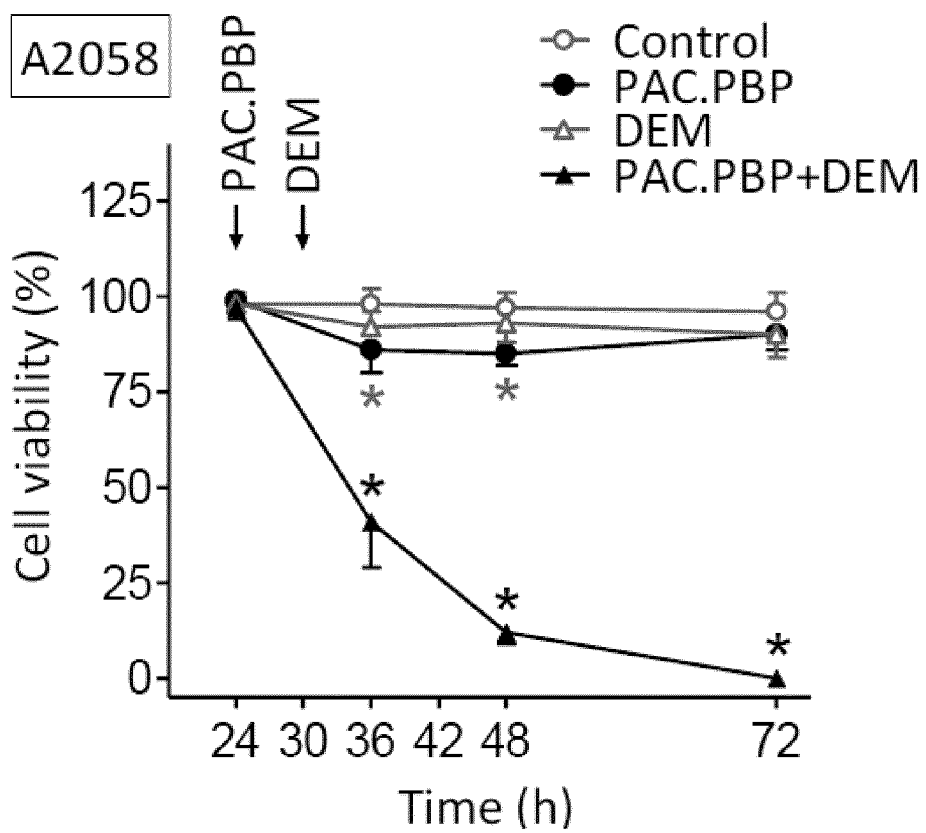
Figure 5:
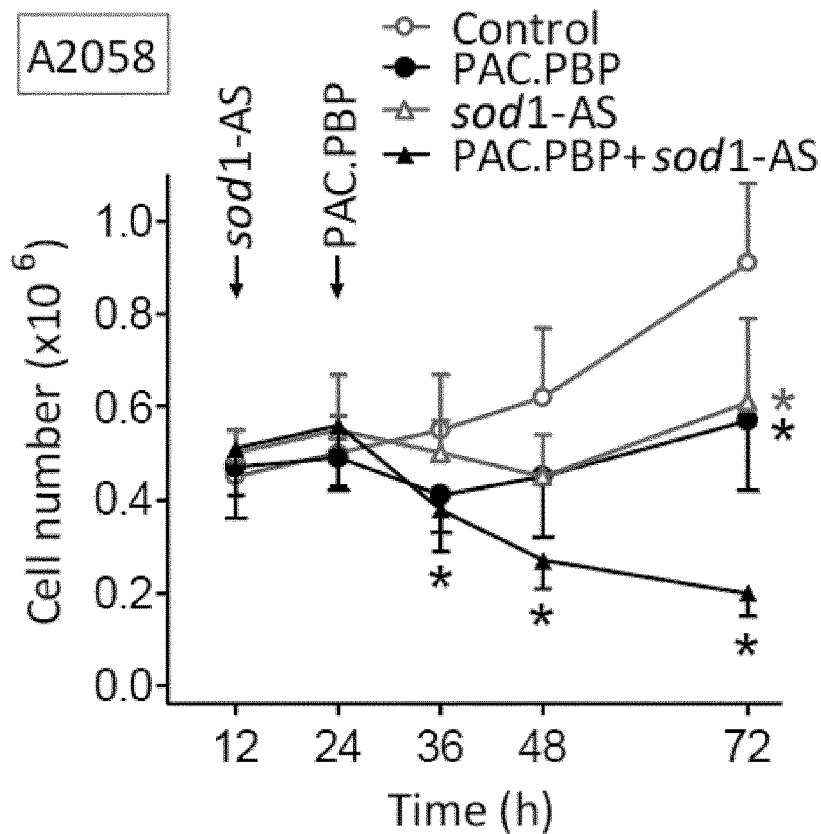
Figure 5:
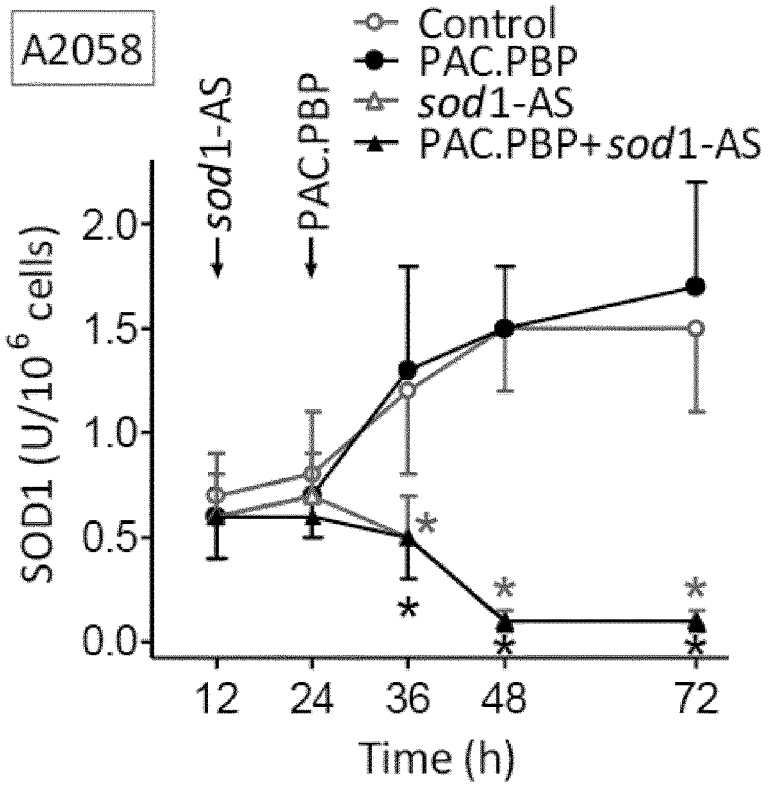
Figure 5:
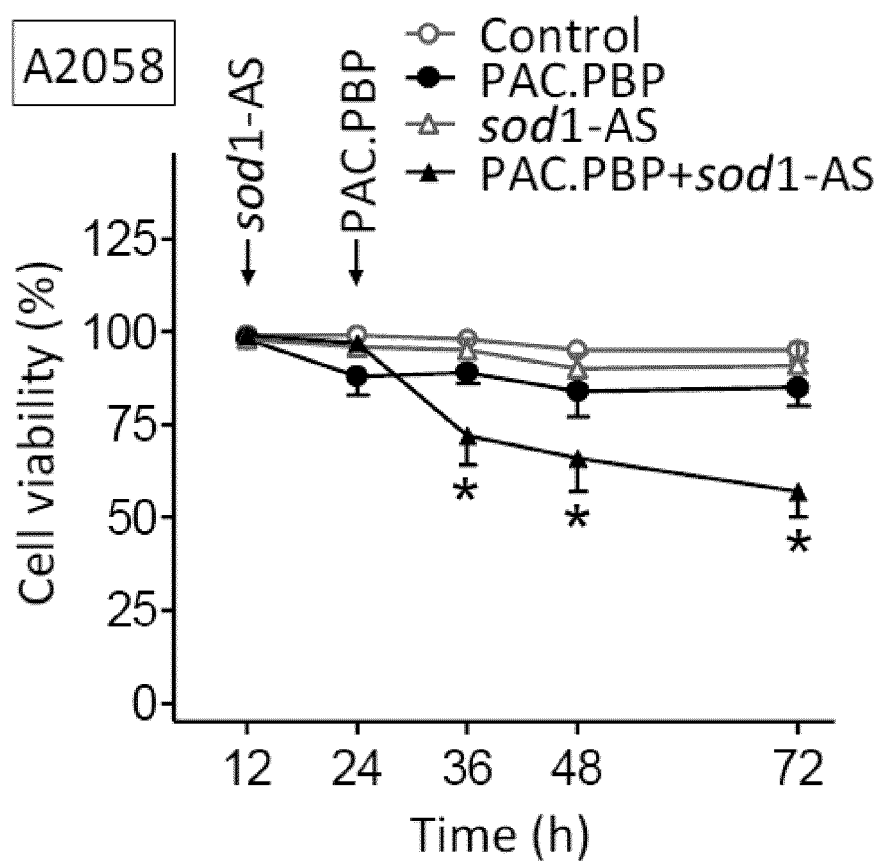

Pterostilbene was administered to tumor bearing mice as in FIGS. 5 (A2058), 11 (AsPC-1), and 15 (all the other cancer models). Tumor cells were isolated from xenografts and cultured as described under Methods. Piperlongumine and tumor type-specific chemotherapy were incubated at the concentrations and timing used in FIGS. 18-25.
*$p < 0.01$ comparing conditions under PL + Chemo versus their respective controls;
†$p < 0.01$ comparing +Pter versus −Pter (n = 5 in all conditions).

The invention claimed is:

1. A method for the treatment of human melanoma, pancreatic, breast, lung, liver, prostate, ovarian, and colorectal cancers, comprising administering a combination of (i) pterostilbene, pterostilbene phosphate or a pharmaceutically acceptable salt thereof, (ii) a glutathione depleting agent selected from the group consisting of diethyl maleate, piperlongumine and I-BET762 (GSK525762A), and (iii) a cancer chemotherapeutic agent, to a patient, wherein the pterostilbene, pterostilbene phosphate or a pharmaceutically acceptable salt thereof is administered at least 12 hours before the administration of the glutathione depleting agent and the cancer chemotherapeutic agent, and wherein the administration of the glutathione depleting agent starts before the administration of the cancer chemotherapeutic agent.

2. The method of claim 1, wherein pterostilbene, pterostilbene phosphate or a pharmaceutically acceptable salt thereof is administered at least 1 day, preferably at least 1 week, before the administration of the glutathione depleting agent.

3. The method of claim 1, wherein the glutathione depleting agent is piperlongumine.

4. The method of claim 1, wherein the glutathione depleting agent is I-BET762 (GSK525762A).

5. The method of claim 1, wherein the glutathione depleting agent is diethylmaleate.

6. The method of claim 1, wherein the cancer is melanoma.

7. The method of claim 1, wherein the cancer is lung cancer.

8. The method of claim 1, wherein the cancer is pancreatic cancer.

9. The method of claim 1, wherein the cancer is colorectal cancer.

10. The method of claim 1, wherein the cancer is selected from the list consisting of prostate, ovarian and breast cancer.

11. The method of claim 1, wherein said combination is administered by the intravenous, oral or intraperitoneal route.

* * * * *

SEQUENCE LISTING

<160> NUMBER OF SEQ ID NOS: 12

<210> SEQ ID NO 1
<211> LENGTH: 48
<212> TYPE: DNA
<213> ORGANISM: Artificial Sequence
<220> FEATURE:
<223> OTHER INFORMATION: 35S-labeled oligonucleotide probes for murine
<220> FEATURE:
<221> NAME/KEY: misc_feature
<222> LOCATION: (1)..(48)

<400> SEQUENCE: 1
ggcccgcggc gctccagaga cggatcccct gctcagcagg gccctgca        48

<210> SEQ ID NO 2
<211> LENGTH: 23
<212> TYPE: DNA
<213> ORGANISM: Artificial Sequence
<220> FEATURE:
<223> OTHER INFORMATION: GSH transferase A1 (GSTA1) sense
<220> FEATURE:
<221> NAME/KEY: misc_feature
<222> LOCATION: (1)..(23)

<400> SEQUENCE: 2
ttccttactg gtcctcacat ctc        23

<210> SEQ ID NO 3
<211> LENGTH: 20
<212> TYPE: DNA
<213> ORGANISM: Artificial Sequence
<220> FEATURE:
<223> OTHER INFORMATION: GSH transferase A1 (GSTA1), antisense
<220> FEATURE:
<221> NAME/KEY: misc_feature
<222> LOCATION: (1)..(20)

<400> SEQUENCE: 3
tcaccggatc atggccagca        20

<210> SEQ ID NO 4
<211> LENGTH: 20
<212> TYPE: DNA
<213> ORGANISM: Artificial Sequence
<220> FEATURE:
<223> OTHER INFORMATION: thioredoxin reductase 1 (TXNRD1), sense
<220> FEATURE:

```
<221> NAME/KEY: misc_feature
<222> LOCATION: (1)..(20)

<400> SEQUENCE: 4
gtgttgtggg ctttcacgta                                                     20

<210> SEQ ID NO 5
<211> LENGTH: 18
<212> TYPE: DNA
<213> ORGANISM: Artificial Sequence
<220> FEATURE:
<223> OTHER INFORMATION: thioredoxin reductase 1 (TXNRD1), antisense
<220> FEATURE:
<221> NAME/KEY: misc_feature
<222> LOCATION: (1)..(18)

<400> SEQUENCE: 5
cagcctggag gatgcttg                                                       18

<210> SEQ ID NO 6
<211> LENGTH: 20
<212> TYPE: DNA
<213> ORGANISM: Artificial Sequence
<220> FEATURE:
<223> OTHER INFORMATION: malic enzyme 1 (ME1), sense
<220> FEATURE:
<221> NAME/KEY: misc_feature
<222> LOCATION: (1)..(20)

<400> SEQUENCE: 6
agtgcctacc tgtgatgttg                                                     20

<210> SEQ ID NO 7
<211> LENGTH: 20
<212> TYPE: DNA
<213> ORGANISM: Artificial Sequence
<220> FEATURE:
<223> OTHER INFORMATION: malic enzyme 1 (ME1), antisense
<220> FEATURE:
<221> NAME/KEY: misc_feature
<222> LOCATION: (1)..(20)

<400> SEQUENCE: 7
ggcttgacct ctgattctct                                                     20

<210> SEQ ID NO 8
<211> LENGTH: 19
<212> TYPE: DNA
<213> ORGANISM: Artificial Sequence
<220> FEATURE:
<223> OTHER INFORMATION: isocitrate dehydrogenase 1 (IDH1), sense
<220> FEATURE:
<221> NAME/KEY: misc_feature
<222> LOCATION: (1)..(19)

<400> SEQUENCE: 8
accaaatggc accatacga                                                      19

<210> SEQ ID NO 9
<211> LENGTH: 23
<212> TYPE: DNA
<213> ORGANISM: Artificial Sequence
<220> FEATURE:
<223> OTHER INFORMATION: isocitrate dehydrogenase 1 (IDH1), antisense
<220> FEATURE:
<221> NAME/KEY: misc_feature
<222> LOCATION: (1)..(23)

<400> SEQUENCE: 9
```

```
ttcatacctt gcttaatggg tgt                                             23

<210> SEQ ID NO 10
<211> LENGTH: 25
<212> TYPE: DNA
<213> ORGANISM: Artificial Sequence
<220> FEATURE:
<223> OTHER INFORMATION: primer sequences (5' to 3') used for POMC,
      sense
<220> FEATURE:
<221> NAME/KEY: misc_feature
<222> LOCATION: (1)..(25)

<400> SEQUENCE: 10
agtgtcgtca gaaagaacga acggc                                           25

<210> SEQ ID NO 11
<211> LENGTH: 21
<212> TYPE: DNA
<213> ORGANISM: Artificial Sequence
<220> FEATURE:
<223> OTHER INFORMATION: primer sequences (5' to 3') used for POMC,
      antisense
<220> FEATURE:
<221> NAME/KEY: misc_feature
<222> LOCATION: (1)..(21)

<400> SEQUENCE: 11
ctcaactggt gtcgtggagt c                                               21

<210> SEQ ID NO 12
<211> LENGTH: 20
<212> TYPE: DNA
<213> ORGANISM: Artificial Sequence
<220> FEATURE:
<223> OTHER INFORMATION: Fully phosphorothioate-modified chimeric 20-mer
      human sod1 antisense oligonucleotide
<220> FEATURE:
<221> NAME/KEY: misc_feature
<222> LOCATION: (1)..(20)

<400> SEQUENCE: 12
gtcgcccttc agcacgcaca                                                 20
```